United States Patent [19]

Ausich et al.

[11] Patent Number: 5,545,816

[45] Date of Patent: Aug. 13, 1996

[54] PHYTOENE BIOSYNTHESIS IN GENETICALLY ENGINEERED HOSTS

[75] Inventors: Rodney L. Ausich, Glen Ellyn; Friedhelm L. Brinkhaus, Lisle; Indrani Mukharji, Evanston; John Proffitt, Oak Park; James Yarger, St. Charles; Huei-Che B. Yen, Naperville, all of Ill.

[73] Assignee: Amoco Corporation, Chicago, Ill.

[21] Appl. No.: 93,577

[22] Filed: Jul. 19, 1993

Related U.S. Application Data

[63] Continuation of Ser. No. 785,569, Oct. 30, 1991, abandoned, and a continuation-in-part of Ser. No. 662,921, Feb. 28, 1991, abandoned, which is a continuation-in-part of Ser. No. 562,674, Aug. 3, 1990, abandoned, which is a continuation-in-part of Ser. No. 525,551, May 18, 1990, abandoned, which is a continuation-in-part of Ser. No. 487,613, Mar. 2, 1990, abandoned.

[51] Int. Cl.$^6$ .............................. A01H 4/00; C12N 15/31; C12N 15/82
[52] U.S. Cl. ..................... 800/205; 435/320.1; 536/23.2; 600/DIG 24; 600/ DIG 43
[58] Field of Search ...................... 536/23.2; 435/320.1, 435/69.1, 67, 240.4; 800/205, DIG 43, DIG 24

[56] References Cited

U.S. PATENT DOCUMENTS

| | | | |
|---|---|---|---|
| 3,637,767 | 1/1972 | Alvarez | 268/343 R |
| 3,833,350 | 9/1974 | Cooke et al. | 426/268 |
| 4,769,061 | 9/1988 | Comai | 435/172.3 |
| 5,034,323 | 7/1991 | Jorgensen et al. | 435/172.3 |
| 5,349,126 | 9/1994 | Chappell et al. | 800/205 |
| 5,429,939 | 7/1995 | Misawa et al. | 435/67 |

OTHER PUBLICATIONS

Napoli et al., *Plant Cell*, 2:279–289 (Apr. 1990).
van der Krol et al., Plant Cell , 2:291–299 (Apr. 1990).
Smith et al., Mol. Gen. Genet , 224:477–481 (1990).
Mol et al., Plant Molecular Biology , —:287–294 (1989).
Jorgensen, Trends in Biotechnol., 8:340–344 (1990).
Otto Straub, *Key to Carotenoids*, 2nd Ed. 1987, edited by H. Pfander et al, Birhkauser Verlag, Basel. Synopsis.
Nelson, et al (Mar. 1989) Mol. and Cell. Biol 9(3): 1271–1276.
Tuveson, et al (1988) Journal of Bacteriology 170(10):4675–4680.
Perry, et al (1986) Journal of Bacteriology 168(2):607–612.
Romer et al (1993) Biochem Biophys Res. Commun. 169(3):1414–1421.
Cunningham, et al (1993) FEBS Lett 328 :130–138.

Primary Examiner—Che S. Chereskin
Attorney, Agent, or Firm—Frank J. Sroka

[57] ABSTRACT

DNA segments encoding the *Erwinia herbicola* enzymes geranylgeranyl pyrophosphate (GGPP) synthase and phytoene synthase, vectors containing those DNA segments, host cells containing the vectors and methods for producing those enzymes and phytoene by recombinant DNA technology in transformed host organisms are disclosed.

15 Claims, 21 Drawing Sheets

Carotenoid Biosynthesis Scheme

```
Bgl II
AGATCTAAAGGCACAGGTCTCATGCTTCGCACAATGTAAAACTGCTTCAGAACCTGGCG    60

Hpa I
AGAGCTATCCGCGGTCTACGGTTAACTGATACTAAAAGACAATTCAGCGGGTAACCTT    120

Nru I
GCAATGGTGAGTGGCAGTAAAGCGGGGCGTTCGCCTCATCGCGAAATAGAGGTAATGAGA    180
     MetValSerGlySerLysAlaGlyValSerProHisArgGluIleGluValMetArg

CAATCCATTGACGATCACCTGGCCTGTTACCTGAAACCGACAGCCAGGATATCGTC       240
GlnSerIleAspAspHisLeuAlaGlyLeuLeuProGluThrAspSerGlnAspIleVal

Bam HI
AGCCTTGCGATGCGTGAAGGCGTCATGGCACCCGGTAAACGGATCCGTCCGCTGCTGATG   300
SerLeuAlaMetArgGluGlyValMetAlaProGlyLysArgIleArgProLeuLeuMet

CTGCTGGCCGCGGACCTCCGCTACCAGGGCAGTATGCCTAGCGCTGCTCGATCTCGCC    360
LeuLeuAlaAlaArgAspLeuArgTyrGlnGlySerMetProThrLeuLeuAspLeuAla

TGCGCCGTTGAACTGACCCATACCGCGTCGCTGATGCTCGACGACATGCCCTGCATGGAC   420
CysAlaValGluLeuThrHisThrAlaSerLeuMetLeuAspAspMetProCysMetAsp
```

FIGURE 2-1

```
ACCGCCGAGCTGCCGCCGGGTCAGCCCACTACCCACAAAAATTGGTGAGAGCGTGGCG      480
AsnAlaGluLeuArgGlyArgGlyGlnProThrThrHisLysLysPheGlyGluSerValAla

ATCCTTGCCTCCGTTGGCTGCTCTCTAAAGCCTTTGGTCTGATCGCCCACCGGCGAT       540
IleLeuAlaSerValGlyLeuLeuSerLysAlaPheGlyLeuIleAlaAlaThrGlyAsp

CTGCCGGGGGAGAGGCTGCCCAGGCGGTCAACGAGCTCTACCGCCGTGGGCTGCAG        600
LeuProGlyGluArgArgArgAlaGlnAlaValAlaAsnGluLeuSerThrAlaValGlyLeuGln

GGCCTGGTACTGGGGCAGTTTCGGCGATCTTAACGATGCCGCCCTCGACCGTACCCCTGAC   660
GlyLeuValLeuGlyGlnPheArgAspLeuAsnAspAlaAlaLeuAspArgThrProAsp

GCTATCCTCAGCACCAACCACCTCAAGACCGGCATTCTGTTCAGCGCGATGCTGCAGATC    720
AlaIleLeuSerThrAsnHisLeuLysThrGlyIleLeuPheSerAlaMetLeuGlnIle

GTCGCCATTGCTTCCGCCTCCGCCCTCGTGCCGAGCACGGCGAGAGACGCTGACGCTTCGCCCTC  780
ValAlaIleAlaSerAlaSerProSerThrArgGluThrLeuHisAlaPheAlaLeu

GACTTCGGCCAGGCGTTCAACTGCTGGACGATCTGCTGACGATCACCCGAAACCGGT       840
AspPheGlyGlnAlaPheGlnLeuLeuAspAspLeuArgAspHisProGluThrGly
```

FIGURE 2-2

```
AAAGATCGCAATAAGGACGCGGGAAAATCGACGCTGGTCAACCGGCTGGGCGCAGACGCG      900
LysAspArgAsnLysAspAlaGlyLyLysSerThrLeuValAsnArgLeuGlyAlaAspAla

GCCCGGCAAAAGCTGCGCGAGCATATTGATTCCGCCGACAAACACCTCACTTTTGCCTGT      960
AlaArgGlnLysLeuArgGluHisIleAspSerAlaAspLysHisLeuThrPheAlaCys
                                 Bal I
CCGCAGGGCGGCGCCATCCGACAGTTTATGCATCTGTGGTTTGGCCATCACCTTGCCCGAC   1020
ProGlnGlyGlyAlaIleArgGlnPheMetHisLeuTrpPheGlyHisHisLeuAlaAsp

TGGTCACCGGTCATGAAAATCGCCCTGATACCCGCCCTTTTGGGTTCAAGCAGTACATAACG  1080
TrpSerProValMetLysIleAla

ATGGAACCACCATTACAGGAGTAGTGATGAATGAAGGACGAGCCCTGTTCAGCCGTAAGA    1140

Eco RV
ACGATCATCTGGATATC
```

FIGURE 2-3

Bgl II
AGATCTAAAGGCACAGGCGTCTCATGCTTCGCACAATGTAAACTGCTTCAGAACCTGGCG    60

Hpa I
AGAGCTATCCGCGGGTCTACGGTTAACTGATACTAAAAGACAATTCAGCGGGTAACCTT   120

Nco I       Nru I
GCAATGGTGAGTGGCAGTAAAGCGGGCGTCATGGCCGAATTCGAAATAGAGGTAATGAGA   180
                          MetAlaGluPheGluIleGluValMetArg

CAATCCATTGACGATCACCTGG?CTGTTACCTGAAACCGACAGCCAGGATATCGTC   240
GlnSerIleAspAspHisLeuAlaGlyLeuLeuProGluThrAspSerGlnAspIleVal

Bam HI
AGCCTTGCGATGCGTGAAGGCGTCATGGCCACCCGGTAAACGGATCCGCTCCGTGATG    300
SerLeuAlaMetArgGluGlyValMetAlaProGlyLysArgIleArgProLeuLeuMet

CTGCTGGCCCGCGACCTCCGCTACCAGGCCAGTATGCCAGTATGCCTCGATCTCGCC   360
LeuLeuAlaAlaArgAspLeuArgTyrGlnGlySerMetProThrLeuLeuAspLeuAla

TGCGCCGTTGAACTGACCCATACCGCCGTCGCTGATGCTCGACGACATGCCCTGCATGGAC   420
CysAlaValGluLeuThrHisThrAlaSerLeuMetLeuAspMetProCysMetAsp

FIGURE 3-1

```
ACCGCCGAGCTGCGCGGTCAGCCCACTACCCACAAAAATTGGTGAGAGCGTGGCG        480
AsnAlaGluLeuArgArgGlyGlnProThrThrHisLysLysPheGlyGluSerValAla

ATCCTTGCCTCCGTTGGCCTGCTCTAAAGCCCTTGGTCTGATCGCCACCGGCGAT        540
IleLeuAlaSerValGlyLeuLeuLysAlaLeuGlyLeuIleAlaAlaThrGlyAsp

CTGCCGGGGAGAGGCGTGCCCAGGCGTCAACGAGCTCTACCGCGTGGGCTGCAG        600
LeuProGlyGlyArgArgAlaGlnAlaValAsnGluLeuTyrArgValGlyLeuGln

GGCCTGGTACTGGGCAGTTTCGGATCTTAACGATGCCCCTCGACCCTGTACCCCCTGAC    660
GlyLeuValLeuGlyGlnPheArgAspLeuAsnAspAlaAlaLeuAspArgThrProAsp

GCTATCCTCAGCACCAACCACCTCAAGACCGGCATTCTGTTCAGCGCGATGCTGCAGATC  720
AlaIleLeuSerThrAsnHisLeuLysThrGlyIleLeuPheSerAlaMetLeuGlnIle

GTCGCCATTGCTTCGCCTTCCGCCTCGTGCCGAGCGCGAGAGACGCTGCACGCCTTCGCCCTC 780
ValAlaIleAlaSerAlaSerProSerThrArgGluThrLeuHisAlaPheAlaLeu

GACTTCGGCCAGGGCGTTTCAACTGCTGGACGATCGCGGTGACGATCACCCGGAAACCGGT 840
AspPheGlyGlnGlyPheGlnAlaPheGlnLeuLeuAspLeuAspArgAspHisProGluThrGly
```

FIGURE 3-2

```
AAAGATCGCAATAAGGACGCGGGAAAATCGACGCTGGTCAACCGGCTGGGCGCAGACGCG    900
LysAspArgAsnLysAspAlaGlyAlaGlyLysSerThrLeuValAsnArgLeuGlyAlaAspAla

GCCCGGCAAAAGCTGCGCGAGCATATTGATTCCGCCAAACACCTCACTTTGCCTGT       960
AlaArgGlnLysLeuArgGluHisIleAspSerAlaAspLysHisLeuThrPheAlaCys

Bal I
CCGCAGGGCGGCGCCATCCGACAGTTTATGCATCTGTGGTTGGCCATCACCTTGCCGAC    1020
ProGlnGlyGlyAlaIleArgGlnPheMetHisLeuTrpPheGlyHisHisLeuAlaAsp

TGGTCACCGGTCATGAAAATCGCCCTGATACCGCCCTTTGGGTTCAAGCAGTACATAACG   1080
TrpSerProValMetLysIleAla

ATGGAACCACATTACAGGAGTAGTGATGAATGAAGGACGAGCCCTTGTTCAGGGTAAGA    1140

Eco RV
ACGATCATCTGGATATC
```

FIGURE 3-3

```
                                              Bgl II                              Nco I
GATTGAGGATCTGCAATGAGCCAACCGCCGCTGCTTGACCAGCCACCGCCAGACCATGGCC        60
                       MetSerGlnProProLeuLeuAspHisAlaThrGlnThrMetAla

AACGGCTCGAAAAGTTTTGCCACCGCTGCGAAGCTGTTCGACCCGGCCACCCGCCGTAGC       120
AsnGlySerLysSerPheAlaThrAlaAlaLysLeuPheAspProAlaThrArgArgSer

GTGCTGATGCTCTACACCCTGGTGCCGCCACTGCGATGACGTCATTGACGACCAGACCCAC      180
ValLeuMetLeuTyrThrLeuValProArgHisCysAspAspValIleAspAspGlnThrHis

GGCTTCGCCAGCGAGCCCGGAGGAGGCCACCCAGCCTGGCTGGAAGCTGGAACGCTGGCGC     240
GlyPheAlaSerGluAlaAlaAlaGluGlyAlaThrGlnArgLeuAlaArgLeuArg

Bam HI
ACGCTGACCCTGGCCGTTTGAAGGGCCGAGATGCAGGATCCGGCCCTTCGCCTGCCTTT       300
ThrLeuThrLeuAlaAlaPheGluGlyAlaGlyAlaGluMetGlnAspProAlaAlaAlaPhe

CAGGAGGTGGCGCTGACCCTGCTATTACGCCCCGGTATTACCCTCGATCACCTCGACGGC     360
GlnGluValAlaLeuThrHisGlyIleThrProArgMetAlaLeuAspHisLeuAspGly

TTTGCGATGGACGTGGCTCAGACCCGGTATGTCACCTTTGAGGATACGCTGCTACTGC       420
PheAlaMetAspValAlaGlnThrArgTyrValThrPheGluAspThrLeuArgTyrCys

FIGURE 4-1
```

```
TATCACGTGGCGGGCTGGTGGTCTGATGATGGCCAGGGTGATGGGCGTGCGGGATGAG          480
TyrHisValAlaGlyValValGlyLeuMetMetAlaArgValMetGlyValArgAspGlu

Sma I
CGGGTGCTGGATCGCGCCTGCGATCTGGGCTGGCCCTTCCAGCTGACGAATATGGCCCGG        540
ArgValLeuAspArgAlaCysAspLeuGlyLeuAlaPheGlnLeuThrAsnMetAlaArg

Pst I
GATATTATTGACGATGCGGCTATTGACCGCTGCTATCTGCCCGAGTGGCTGCAGGAT           600
AspIleIleAspAspAlaAlaIleAspArgCysTyrLeuProAlaGluTrpLeuGlnAsp

GCCGGGCTGGCCCCGGAGAACTATGCGGCGGAGAATCGCCCGGCTCTGGCGGTGG             660
AlaGlyLeuAlaProGluAsnTyrAlaAlaArgGluAsnArgProAlaLeuAlaArgTrp

CGGAGGCTTATTGATGCCGCAGAGCCGTACTACATCTCCTCCCAGGCCCGGCTACACGAT        720
ArgArgLeuIleAspAlaAlaGluProTyrTyrIleSerSerGlnAlaGlyLeuHisAsp

CTGCGGGGGCTCCGGCGTGGCGATGCGGCCACCGCCGCTCTACCGGGAGATCGGT             780
LeuArgArgArgSerAlaTrpAlaIleAlaThrAlaArgSerValTyrArgGluIleGly

ATTAAGGTAAAAGGCGCGGAGGCAGCGCCAGCACCAGCAAAGGT                        840
IleLysValLysAlaAlaGlyGlySerAlaTrpAspArgGlnHisThrSerLysGly
```

FIGURE 4-2

```
GAAAAATTGCCATGCTGATGGCTGCACCGGGGGCAGGTTATTCGGGCGAAGACGACGAGG      900
GluLysIleAlaMetLeuMetAlaAlaProGlyGlnValIleArgAlaAlaLysThrThrArg

GTGACGCCGCCGGCCGTCCGGCCGGTCTTTGGCAGGCGTCCCGTTTAGGCGGGCGGCCATGACGTT  960
ValThrProArgProAlaGlyLeuTrpGlnArgProVal

CACGCAGGATCGCCCTGTAGGTCGGCAGGCTTGCGGGCGTAAATAAACCGAAGGAGACGC      1020

AGCCCTCCCGGCCACCGCGTGGTGGGACGGTAGAGCCGCTTCAGGT                    1080
        Bam HI
AGCCCCGGGCGGGATCCAGTGAAGGGCCAGGCTGATGCACCAGACCGTCGTGCACCA        1140
                                           Pst I
GGAAGTAGAGCAGGCCATAGACCGTCAATGCCGCAGCCAATCCACTGCAGGGGCCAAAC      1200
```

FIGURE 4-3

```
Nco I
TAAACCATGAAAAACCGTTGTGATTGGCGCTTGGTGGCCTGGCGCTGGCGATT       60
     MetLysLysThrValValIleGlyAlaGlyPheGlyGlyLeuAlaLeuAlaIle

Pst I       Bam HI
CGCCTGCAGGCGGCAGGGATCCCAACCGTACTGCTGGAGCAGCGGGACAAGCCCGGGT    120
ArgLeuGlnAlaAlaGlyIleProThrValLeuLeuGluGlnArgAspLysProGlyGly

CGGGCCTACGTCTCTGGCATGACCAGGGCTTTACCTTTGACGGCCGACGGTGATCACC    180
ArgAlaTyrValTrpHisAspGlnGlyPheThrPheAspAlaGlyProThrValIleThr

GATCCTACCGCGCTGTTCACCCTGCCGCAGGCGCATGGAGGATTACGTC            240
AspProThrAlaLeuPheThrLeuAlaLeuAlaGlyArgArgMetGluAspTyrVal

AGGCTGCTGCCGGTAAAACCCTTCTACCGACTCTGCTGGGAGTCCGGAAGACCCTCGAC   300
ArgLeuLeuProValLysProPheTyrArgLeuCysTrpGluSerGlyLysThrLeuAsp

TATGCTAACGACAGCTTCGAGGCGCAGATTACCCAGTTCAACCCCCGCGACGTC       360
TyrAlaAsnAspSerPheGluAlaGlnIleThrGlnPheAsnProArgAspVal

GAGGGCTACGGCTTTCTGGCTTACTCCCAGGCGGTATTCCAGGAGGATATTTGCGC     420
GluGlyTyrArgArgPheLeuAlaTyrSerGlnAlaValPheGlnGluGlyTyrLeuArg
```

FIGURE 11-1

```
                Nru I
CTCGGGCAGCGTGCCGTTCCTCTCTCTTTCGGACATGCTGCGGCCCGGCCAGCTGCTT      480
LeuGlySerValProPheLeuSerPheArgAspMetLeuArgAlaGlyProGlnLeuLeu

AAGCTCCAGGCGTGGCAGAGCGTCTACCAGTCGGTTCGCTTTATTGAGGATGAGCAT      540
LysLeuGlnAlaTrpGlnSerValTyrGlnSerValSerArgPheIleGluAspGluHis

CTGCGGGCAGGCCTTCTCGTTCCACTCCCTGCTGGTAGGCGGCAACCCCTTCACCACCTCG  600
LeuArgGlnAlaPheSerPheHisSerLeuLeuValGlyAsnProPheThrThrSer

TCCATCTACACCCTGATCCACGCCCTTGAGCGGGAGTGGGGTCTGGTTCCCTGAGGGC     660
SerIleTyrThrLeuIleHisAlaLeuGluArgGluTrpGlyValTrpPheProGluGly

GGCACCGGGGCGCTGGTGAACGGCATGGTGAAGCTGTTTACCGATCTGGGCGGGGAGATC   720
GlyThrGlyAlaLeuValAsnGlyMetValLysLeuPheThrAspLeuGlyGlyGluIle

Sma I
GAACTCAACGCCCGGGTCGAAGAGCTGGTGGCCGATAACCGTAAGCCAGGTCCGG        780
GluLeuAsnAlaArgValGluLeuLeuValAlaAspAsnArgValSerGlnValArg

CTCGCGGATGTCGGATCTTTGACACCGACGCCTAGCCTGACTGGTGAAC              840
LeuAlaAspGlyArgIlePheAspThrAspThrAlaSerAsnAlaAspValValAsn
```

FIGURE 11-2

```
ACCTATAAAAAGCTGCTCGGCACCATACCGGTGGGCAGAAGCGGGCGGCACGGCTGGAG    900
ThrTyrLysLysLeuLeuGlyThrIleProValGlyLysGlnLysArgAlaAlaArgLeuGlu

CGCAAGAGCATGAGCAACTCGCTGTTTGTGCTCTACTTCGGCCTGAACCAGCCTCATTCC    960
ArgLysSerMetSerAsnSerLeuPheValLeuTyrPheGlyLeuAsnGlnProHisSer

Bgl II
CAGCTGGCGCCACCATACCATCTGTTTGTCCCGCTACCGGGAGCTGATGACGAGATC     1020
GlnLeuAlaHisHisThrIleCysPheGlyProArgTyrArgGluLeuIleAspGluIle

TTTACCGGCAGCGCGCTGGCGATGACTTCTCGCTCTACCTGCACTCGCCCTGCGTGACC    1080
PheThrGlySerAlaLeuAlaAspAspPheSerLeuTyrLeuHisSerProCysValThr

GATCCCTCGCTCGCGCCTCCCCCGTGCGCCAGCTTCTACGTGCTGGCCCCGGTGCCGCAT    1140
AspProSerLeuAlaProProProCysAlaSerPheTyrValLeuAlaProValProHis

CTTGGCAACGCGCCTGGACTGGGCCAGGAGGGCCGAAGCTGCGACCGGCATCTTT        1200
LeuGlyAsnAlaProLeuAspTrpAlaGlnGluGlyProLysLeuArgAspArgIlePhe

GACTACCTTGAAGAGCGCTATATGCCCGGCCTGGTGACCCAGCGGATC              1260
AspTyrLeuGluGluArgTyrMetProGlyLeuArgSerGlnLeuValThrGlnArgIle
```

FIGURE 11-3

```
TTTACCCGGCAGACTTCACGACACGCTTGGATCGCTTGGATCGCTTTTCATCGAG    1320
PheThrArgGlnThrSerArgHisAlaTrpIleAlaIleLeuGlySerLeuPheIleGlu

CCGCCTTCGTTGACCCAAGGCTTGTTCGCCGCAAACGGACACGACATTCAAACCTCTAC    1380
ProProSerLeuThrGlnGlyLeuPheAlaAlaAsnAlaThrArgHisSerAsnLeuTyr

CTGGTGGCCGCAGGTACTCACCCTGGCGGGGCATTCCTGGCGTAGTGGGCCTCGCCGAA    1440
LeuValAlaAlaGlyThrHisProGlyAlaGlyIleProGlyValValGlyLeuAlaGlu

AGCACCGCCAGCCTGATGATTGAGGATCTGCAATGAGCCAACCGCCGCTGCTTGACCACG    1500
SerThrAlaSerLeuMetIleGluAspLeuGln

Nco I   Bal I
CCACGCAGACCATGGCCA
```

FIGURE 11-4

PHYTOENE BIOSYNTHESIS IN GENETICALLY ENGINEERED HOSTS

CROSS-REFERENCE TO RELATED APPLICATIONS

This is a continuation of U.S. Ser. No. 07/785,569; filed Oct. 30, 1991, now abandoned, and a continuation-in-part of application Ser. No. 07/662,921, filed Feb. 28, 1991, now abandoned, which is a continuation-in-part of application Ser. No. 07/562,674, filed Aug. 3, 1990, now abandoned, which is a continuation-in-part of application Ser. No. 07/525,551, filed May 18, 1990, now abandoned, which is a continuation-in-part of application Ser. No. 07/487,613, filed Mar. 2, 1990 now abandoned.

TECHNICAL FIELD

The present invention relates to carotenoid biosynthesis. More specifically, this invention relates to the isolation, characterization and expression of *Erwinia herbicola* (Erwinia) genes encoding the enzymes geranylgeranyl pyrophosphate (GGPP) synthase (E.C.2.5.1.29) and phytoene synthase that catalyze the formation of the carotenoid, phytoene. The invention also relates to methods for expression of these *Erwinia herbicola* enzyme genes in prokaryote hosts such as *Escherichia coli* (*E. coli*) and *Agrobacterium tumefaciens* (*A. tumefaciens*), in eukaryote hosts such as yeasts like *Saccharomyces cerevisiae* (*S. cerevisiae*) and higher plants such as alfalfa and tobacco, as well as to methods for preparation of the carotenoid, phytoene.

BACKGROUND ART

Carotenoids are 40-carbon ($C_{40}$) terpenoids consisting generally of eight isoprene ($C_5$) units joined together. Linking of the units is reversed at the center of the molecule. Trivial names and abbreviations will be used throughout this disclosure, with IUPAC-recommended semisystematic names given in parentheses after first mention of each name.

Carotenoids are pigments with a variety of applications. For example, beta-carotene (β,β-carotene) is widely known and used as provitamin A and margarine colorant.

Phytoene (7,8,11,12,7',8',11',12'-octahydro-ψ,ψ-carotene) is the first carotenoid in the carotenoid biosynthesis pathway and is produced by the dimerization of a 20-carbon atom precursor, geranylgeranyl pyrophosphate (GGPP). Phytoene has useful applications in treating skin disorders (U.S. Pat. No. 4,642,318) and is itself a precursor for colored carotenoids. Aside from certain mutant organisms, such as *Phycomyces blakesleeanus* carB, no current methods are available for producing phytoene via any biological process.

Current methods for commercial production of carotenoids include chemical synthesis, e.g. beta-carotene, and extraction from biomass, e.g. zeaxanthin.

Carotenoids are synthesized in a variety of bacteria, fungi, algae, and higher plants. At the present time only a few plants are widely used for commercial carotenoid production. However, the productivity of carotenoid synthesis in these plants is relatively low and the resulting carotenoids are expensively produced.

One way to increase the productive capacity of biosynthesis would be to apply recombinant DNA technology. Thus, it would be desireable to produce carotenoids generally and phytoene specifically by recombinant DNA technology. This would permit control over quality, quantity and selection of the most suitable and efficient producer organisms. The latter is especially important for commercial production economics and therefore availability to consumers. For example, yeast, such as *S. cerevisiae* in large fermentors and higher plants, such as alfalfa or tobacco, can be mobilized for carotenoid production as described hereinafter.

An organism capable of carotenoid synthesis and a potential source of genes for such an endeavor is *Erwinia herbicola*, which is believed to carry putative genes for carotenoid production on a plasmid (Thiry, *J. Gen. Microbiol.*, 130:1623 (1984)) or chromosomally (Perry et al., *J. Bacteriol*, 168:607 (1986)). *Erwinia herbicola* is a genus of Gram-negative bacteria of the ENTEROBACTERIACEAE family, which are facultative anaerobes. Indeed, recently published European Patent Application 0 393 690 A1 (published Apr. 20, 1990; sometimes referred to herein as "EP 0 393 690") reports use of DNA from another Erwinia species, *Erwinia uredovora* 20D3 (ATCC 19321), for preparing carotenoid molecules.

As is discussed in detail hereinafter, the present invention utilizes DNA from *Erwinia herbicola* EHO-10 (ATCC 39368) for preparation of carotenoid molecules and the enzymes used in their synthesis. *Erwinia herbicola* EHO-10 used herein is also referred to as *Escherichia vulneris*.

The genus is commonly divided into three groups. Of the three, the Herbicola group includes species (e.g. *Erwinia herbicola*) which typically form yellow pigments that have now been found to be carotenoids.

These bacteria exist as saprotrophs on plant surfaces and as secondary organisms in lesions caused by many plant pathogens. They can also be found in soil, water and as opportunistic pathogens in animals, including man.

A precise organismic function has yet to be ascribed to the pigment(s) produced by *Erwinia herbicola*. Perry et al., *J. Bacteriol.*, 168:607 (1986), showed that the genes coding for the production of an unknown yellow pigment lie within an approximately 13-kilobase (kb) sequence coding for at least seven polypeptides, and that the expression of the yellow pigment is cyclic AMP mediated. Tuveson, *J. Bacteriol.*, 170:4675 (1988), demonstrated that these genes, cloned from Erwinia and expressed in an *E. coli* strain, offered the host some protection against inactivation by near-UV light and specific phototoxic molecules.

*E. coli* and *S. cerevisiae* are commonly used for expressing foreign genes, but to optimize yields and minimize technical maintenance procedures, it would be preferable to utilize a higher plant species.

BRIEF SUMMARY OF THE INVENTION

Because of phytoene's utility in treating skin disorders, its utility as a carotenoid precursor, and the difficulty in producing it by chemical synthesis and extraction from biomass, the ability to produce phytoene in commercially viable amounts from transgenic biological sources with the aid of recombinant DNA technology is a major benefit flowing from this invention. In addition, GGPP and phytoene are in the pathway for biological synthesis of all $C_{40}$ carotenoids such as beta-carotene and zeaxanthin so that the genes that encode enzymes for preparing GGPP and phytoene, and GGPP and phytoene themselves, are also useful in the synthesis of all carotenoids, including beta-carotene and zeaxanthin. To realize these benefits, several aspects and embodiments are contemplated by this invention.

One aspect contemplated by this invention is an isolated DNA segment comprising a nucleotide sequence that contains at least 850 base pairs that define a structural gene for expressing the *Erwinia herbicola* enzyme geranylgeranyl pyrophosphate (GGPP) synthase (E.C. 25.1.29), as well as a DNA variant or analog that code for an enzyme having substantially the same biological activity. GGPP synthase is an enzyme in the pathway for phytoene synthesis.

One preferred sequence includes an engineered Nco I site at the initial Met residue and is present in the approximately 1029 base pair (bp) Nco I-Eco RV restriction fragment of plasmid pARC417BH. A more preferred DNA segment contains the heterologous sequence that is present in the approximately 1150 bp Nco I-Pvu II restriction fragment sequence in the plasmid pARC489B. Most preferred is the heterologous sequence that is present in the approximately 1000 bp Nco I-Pvu II restriction fragment of the plasmid pARC489D, the most productive plasmid.

Another aspect contemplated by this invention is a recombinant DNA molecule comprising a vector operatively linked to an exogenous DNA segment discussed above, and a promoter suitable for driving the expression of the enzyme in a compatible host organism.

Still another aspect contemplated by this invention is a method for preparing the enzyme GGPP synthase. This method comprises initiating a culture, in a nutrient medium, of prokaryotic or eukaryotic host cells transformed with a recombinant DNA molecule containing an expression vector compatible with the cells. This vector is operatively linked to an isolated exogenous *Erwinia herbicola* DNA segment discussed above. The culture is maintained for a time period sufficient for the cells to express the GGPP synthase protein.

Further contemplated by this invention is an isolated DNA segment comprising a nucleotide sequence that contains at least 927 base pairs that defines the structural gene for the *Erwinia herbicola* enzyme phytoene synthase, as well as a DNA variant or analog thereof that encode an enzyme having substantially the same biological activity.

A preferred phytoene synthase structural gene is within the about 1112 bp Nco I-Eco RI fragment present in plasmid pARC285. More preferred is the phytoene synthase structural gene contained in a chimeric DNA segment that is present in plasmids pARC140R and pARC140N. The segment in plasmid pARC140N is excisable as an about 1176 bp fragment.

Yet another aspect contemplated by this invention is a recombinant DNA molecule comprising a vector operatively linked to an exogenous *Erwinia herbicola* DNA segment defining a structural gene capable of expressing the *Erwinia herbicola* enzyme phytoene synthase, DNA variants and analogs thereof as discussed above, and a promoter suitable for driving the expression of the enzyme in a compatible host organism.

Plasmid pARC145G that contains an approximately 1010 bp Nco I-Nco I fragment that includes the approximately 1000 bp Nco I-Pvu II GGPP synthase structural gene-containing sequence of plasmid pARC489D under the control of the GAL 10 promoter, as well as the approximately 1160 bp Bgl II-Eco RI fragment that contains the phytoene synthase structural gene of plasmid pARC140R under the control of the GAL 1 promoter is a particularly preferred recombinant DNA molecule. The same phytoene synthase gene is present in plasmid pARC140N as an about 1176 bp Hpa I-Eco RI fragment.

A still further contemplated aspect of this invention is a method for preparing the enzyme phytoene synthase. This method comprises the steps of initiating a culture, in a nutrient medium, of prokaryotic or eukaryotic host cells transformed with an exogenous recombinant DNA molecule. This molecule contains an expression vector compatible with the cells, operatively linked to a DNA segment defining the structural gene for phytoene synthase, DNA variants and analogs thereof as discussed before. The culture is maintained for a time period sufficient for the cells to express the phytoene synthase protein molecule.

Still another aspect contemplated by this invention is a method for producing phytoene, comprising initiating a culture, in a nutrient medium, of prokaryotic or eukaryotic host cells transformed with one or two recombinant DNA molecule(s). The recombinant DNA contains an expression vector compatible with the host cells operatively linked to an exogenous *Erwinia herbicola* DNA segment comprising (i) a nucleotide base sequence corresponding to a before-discussed sequence defining a structural gene for geranylgeranyl pyrophosphate synthase, its DNA analogs and variants and (ii) a before-discussed nucleotide base sequence corresponding to a sequence defining a structural gene for phytoene synthase and its DNA variants and analogs. The culture is maintained for a time period sufficient for the cells to express phytoene.

A still further embodiment of this invention contemplates the method of preparation of phytoene described above including the further step of recovering the phytoene from the maintained culture. A still further preferred embodiment contemplated by this invention is the method of preparation of phytoene described above, wherein both exogenous *Erwinia herbicola* DNA segments (i) and (ii) are contained in the same expression vector.

Another preferred embodiment of this invention contemplates the method of preparation of phytoene as described above wherein the DNA segment contains a previously-discussed nucleotide base sequence defining a structural gene for geranylgeranyl pyrophosphate synthase, and a previously-discussed nucleotide base sequence that defines a structural gene for phytoene synthase. This preferred embodiment thus includes the heterologous gene located in the plasmid pARC489D construct and the heterologous gene of the plasmid pARC140N construct.

Another preferred embodiment of this invention is a recombinant DNA molecule as described above, wherein the promoter is Rec 7 for *E. coli*, GAL 10 and GAL 1 for yeasts such as *S. cerevisiae*, and CaMV35S for higher plants.

Other preferred embodiments contemplate the methods of preparation described above, wherein the host transformed is either a prokaryote, such as *E. coli*, a eukaryote, for example yeast or a fungus, such as *S. cerevisiae* and *A. nidulans*, respectively, or a higher plant, such as alfalfa or tobacco.

Also contemplated is a method for increasing the production of lutein in higher plants. Here, a higher plant is transformed with a recombinant molecule that encodes a structural gene for the *Erwinia herbicola* enzyme phytoene synthase, a DNA variant or analog thereof that encodes an enzyme exhibiting substantially the same biological activity. The transformed plant is maintained (e.g. grown) for a time period sufficient for the amount of phytoene synthase to be increased above the amount present in a native (normal), non-transformed plant of the same type. The increase in phytoene synthase production leads to an increase in phytoene production, which leads to an increase in lutein in the transformed plant.

Preferably, an about 177 bp sequence that encodes a chloroplast transit peptide of the tobacco ribulose bis-phosphate carboxylase-oxygenase gene is operatively linked in frame to the 5' end of the phytoene synthase structural gene. This construct leads to increased production of lutein in the chloroplast of the transformed plant as compared to a native, non-transformed plant of the same type.

Still further embodiments and advantages of the invention will become apparent to those skilled in the art upon reading the entire disclosure contained herein.

BRIEF DESCRIPTION OF THE DRAWINGS

FIG. 2 in three sheets as FIG. 2-1, FIG. 2-2, and FIG. 2-3 illustrates the nucleotide base sequences of certain preferred DNA segments of the structural gene for geranylgeranyl pyrophosphate (GGPP) synthase (SEQ ID NO:1). The base sequences are shown conventionally from left to right and in the direction of 5' terminus to 3' terminus, using the single letter nucleotide base code.

The reading frame of the 5' end of the structural gene illustrated herein is indicated by placement of the deduced, amino acid residue sequence (SEQ ID NO:2) of the protein for which it codes below the nucleotide sequence, such that the triple letter code for each amino acid residue is located directly below the three-base codon for each amino acid residue. Numerals to the right of the DNA sequence indicate nucleotide base positions within the DNA sequence shown. All of the structural genes shown in the figures herein are similarly illustrated, with amino acid initiation position beginning here with the initial methionine residue (Met) at DNA position about 124 as shown.

Several restriction enzyme sites of importance are indicated above the DNA sequence. These represent points of manipulation in engineering the gene construct encoding the enzyme.

Figure 1:
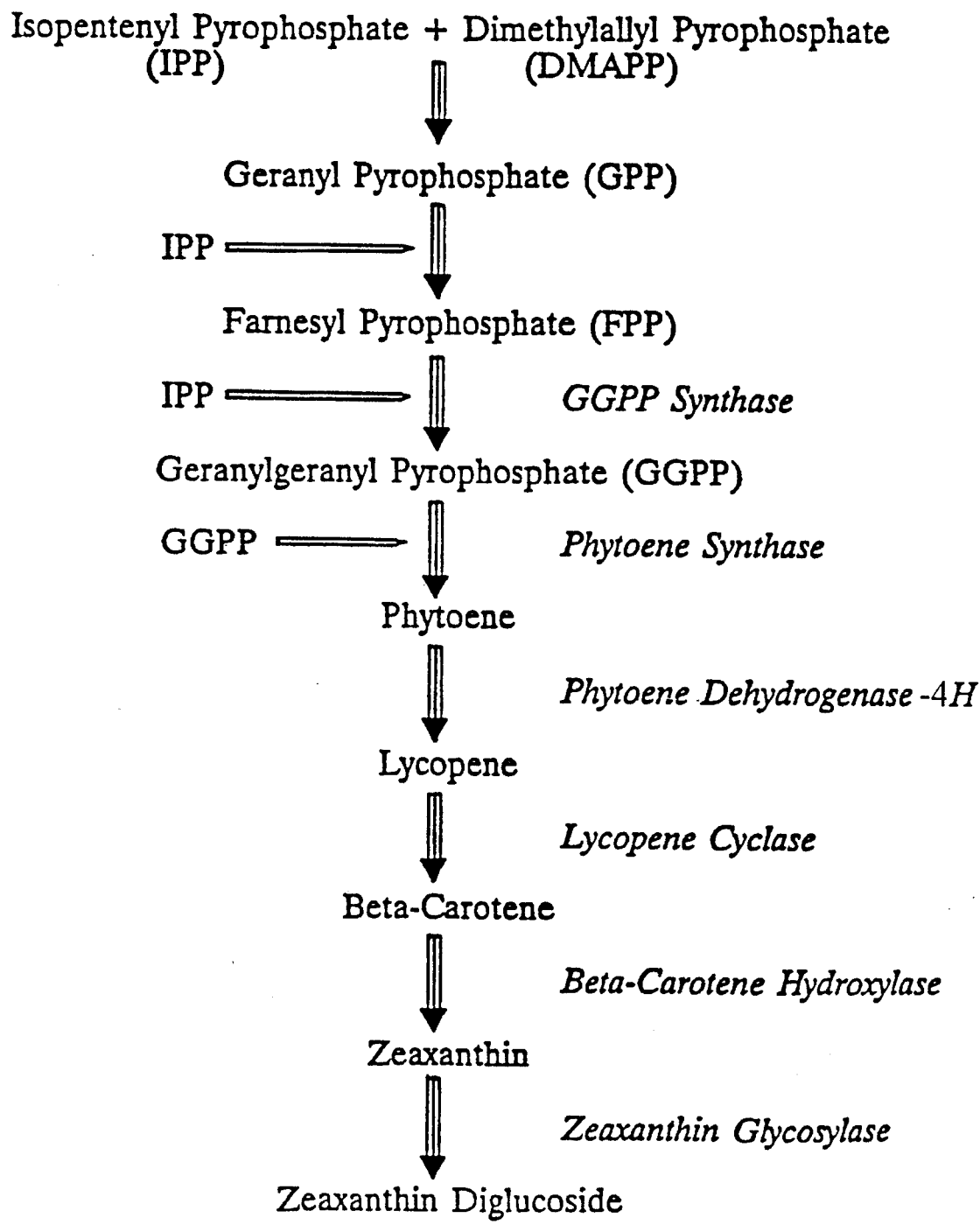
FIG. 1 is a flow diagram of the carotenoid biosynthesis pathway utilizing the *Erwinia herbicola* gene complement located in the plasmid pARC376.

FIG. 3 shown in three sheets as FIG. 3-1, FIG. 3-2 and FIG. 3-3 illustrates the DNA (SEQ ID NO:3) and deduced amino acid residue (SEQ ID NO:4) sequences of more preferred, heterologous structural genes of *Erwinia herbicola* GGPP synthase. Here, the expressed protein begins with the Met residue at about position 150 as shown and terminates within the Eco RV site (about 1153) in the DNA construct present in plasmid pARC489B, whereas the gene terminates at the Bal I site (about 1002) in the DNA construct present in plasmid pARC489D. The short amino-terminal sequence MetAlaGluPhe (about 150–161) is a heterologous sequence from plasmid pARC306A, and is substituted for the native sequence from DNA position 124 to 150 shown in FIG. 2.

FIG. 4 shown in three sheets as FIG. 4-1, FIG. 4-2 and FIG. 4-3 illustrates the nucleotide (SEQ ID NO:5) and amino acid (SEQ ID NO:6) sequences of the structural gene for phytoene synthase.

Figure 5:
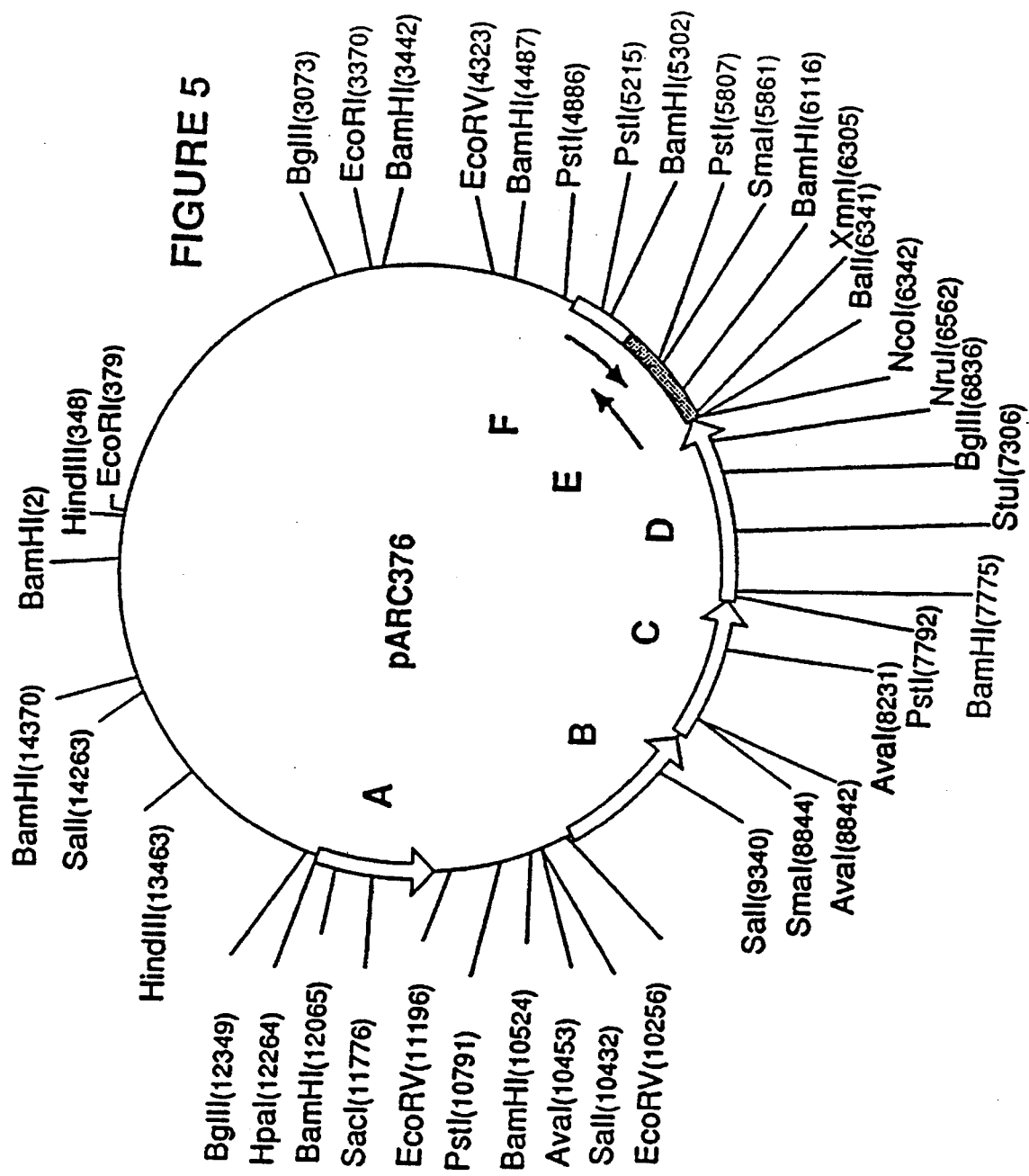

The Met initiation codon (about position 16 as shown) corresponds to about position 6383 on plasmid pARC376 in FIG. 5. The Bam HI restriction site at about 1093 in FIG. 4 corresponds to the Bam HI site at about position 5302 on plasmid pARC376 in FIG. 5. The illustrated Bgl II restriction site shown at about position 8 is not present in the native DNA sequence and was added as is discussed hereinafter.

FIG. 5 schematically illustrates the plasmid pARC376 containing the full complement of enzyme genes, represented by capital letters, required for the synthesis of carotenoids from farnesyl pyrophosphate, as indicated in the schematic of FIG. 1. Note that the direction of transcription (arrows) is uniform for all enzyme structural genes except beta-carotene hydroxylase (F), which is transcribed in an opposite direction. Important restriction enzyme sites are also identified. The synthesis of phytoene is catalyzed by the enzymes GGPP synthase (A) and phytoene synthase (E). The gene labeled D encodes the enzyme phytoene dehydrogenase-4H. Genes labeled B, C and F encode the enzymes zeaxanthin glycosylase, lycopene cyclase, and beta-carotene hydroxylase, respectively. The overlap of genes E and F is shown by hatching.

Figure 6:
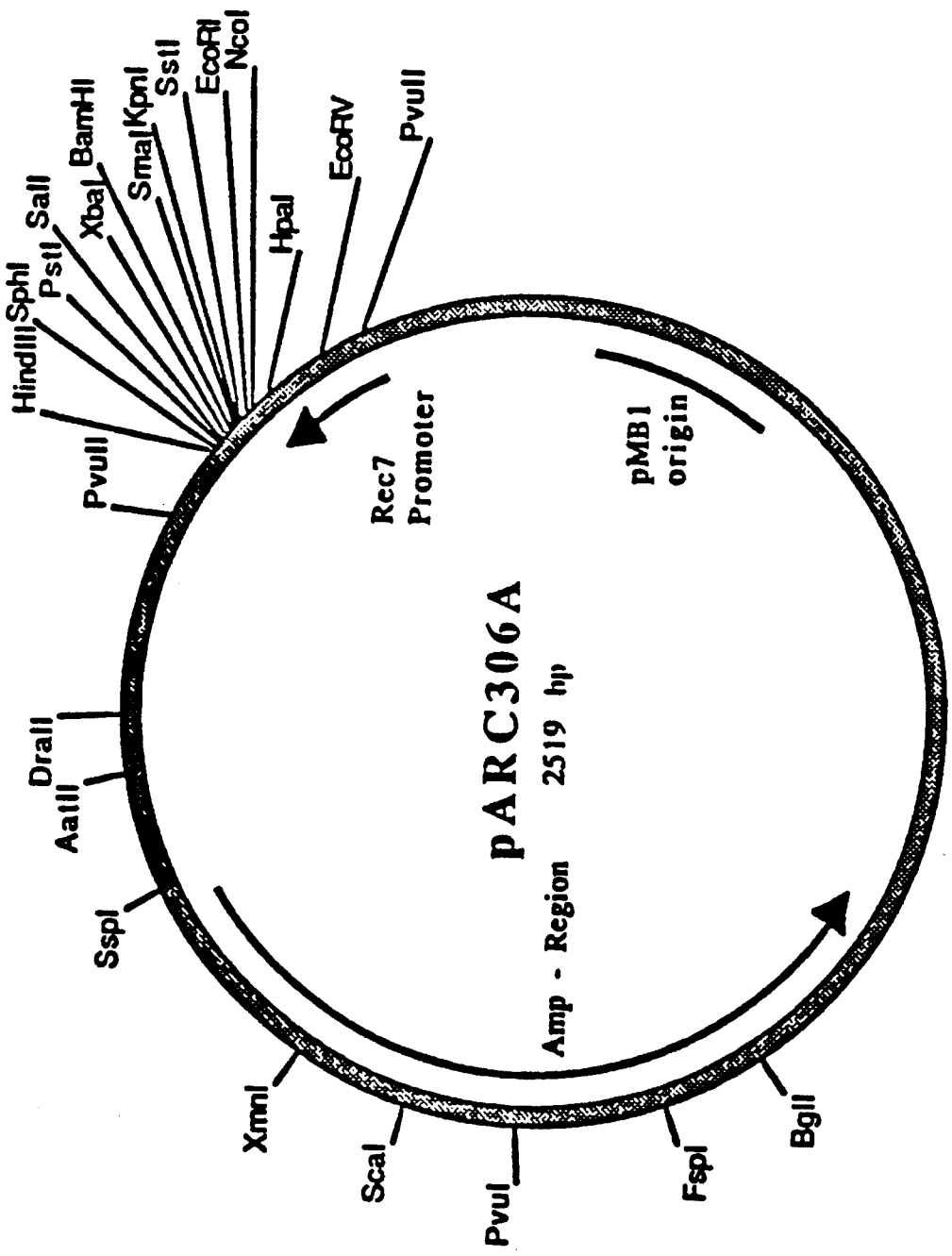

FIG. 6 is a schematic representation of the plasmid pARC306A, which contains the Rec 7 promoter. This plasmid also has a multiple cloning site adjacent to the Rec 7 promoter and 5' and 3' transcription termination loops. Approximate positions of restriction enzyme sites are shown.

Figure 7:
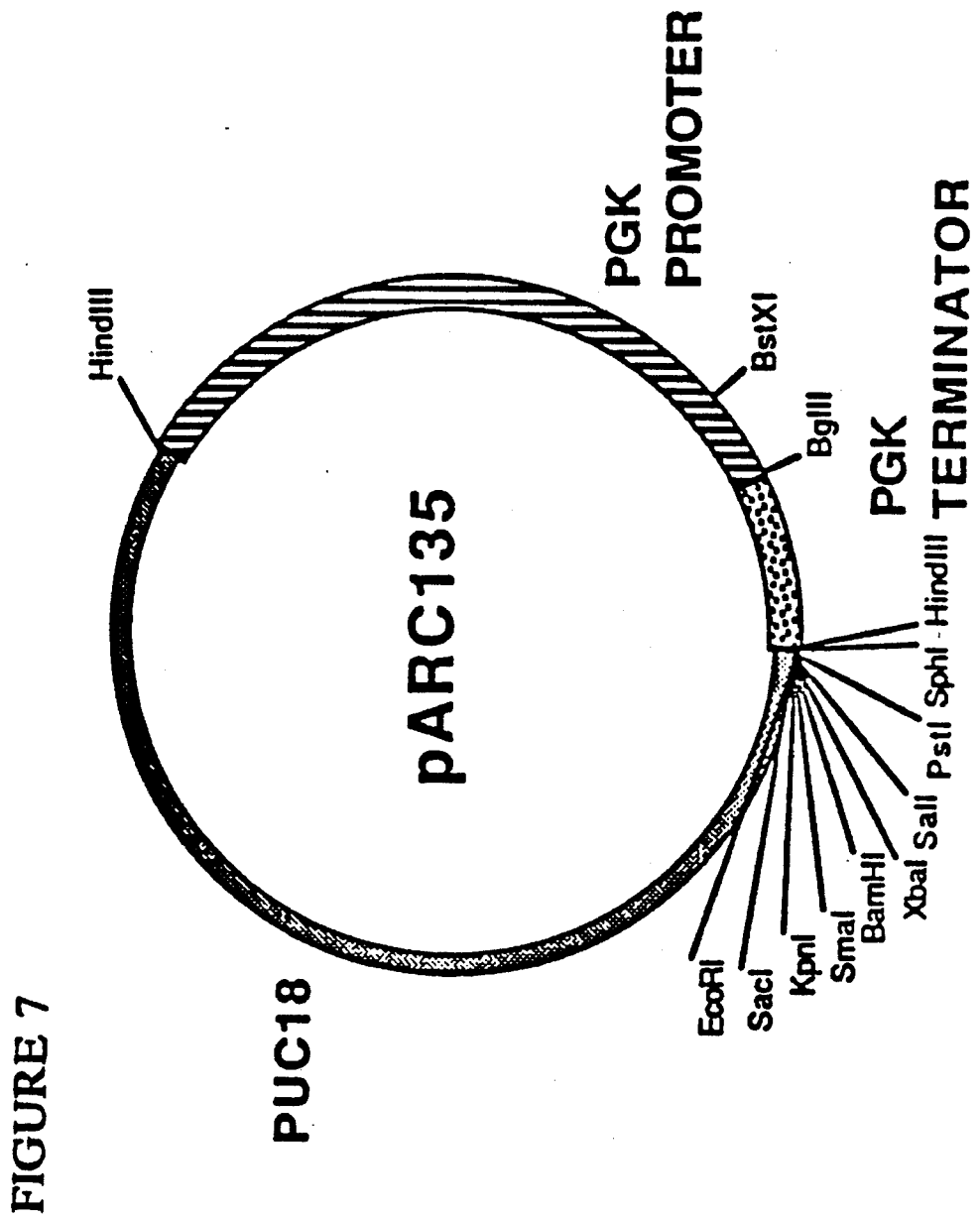

FIG. 7 illustrates schematically the plasmid pARC135, which contains the *S. cerevisiae* phosphoglyceric acid kinase (PGK) promoter operatively linked at the Bgl II site. Various additional features of the plasmid are also illustrated.

Figure 8:
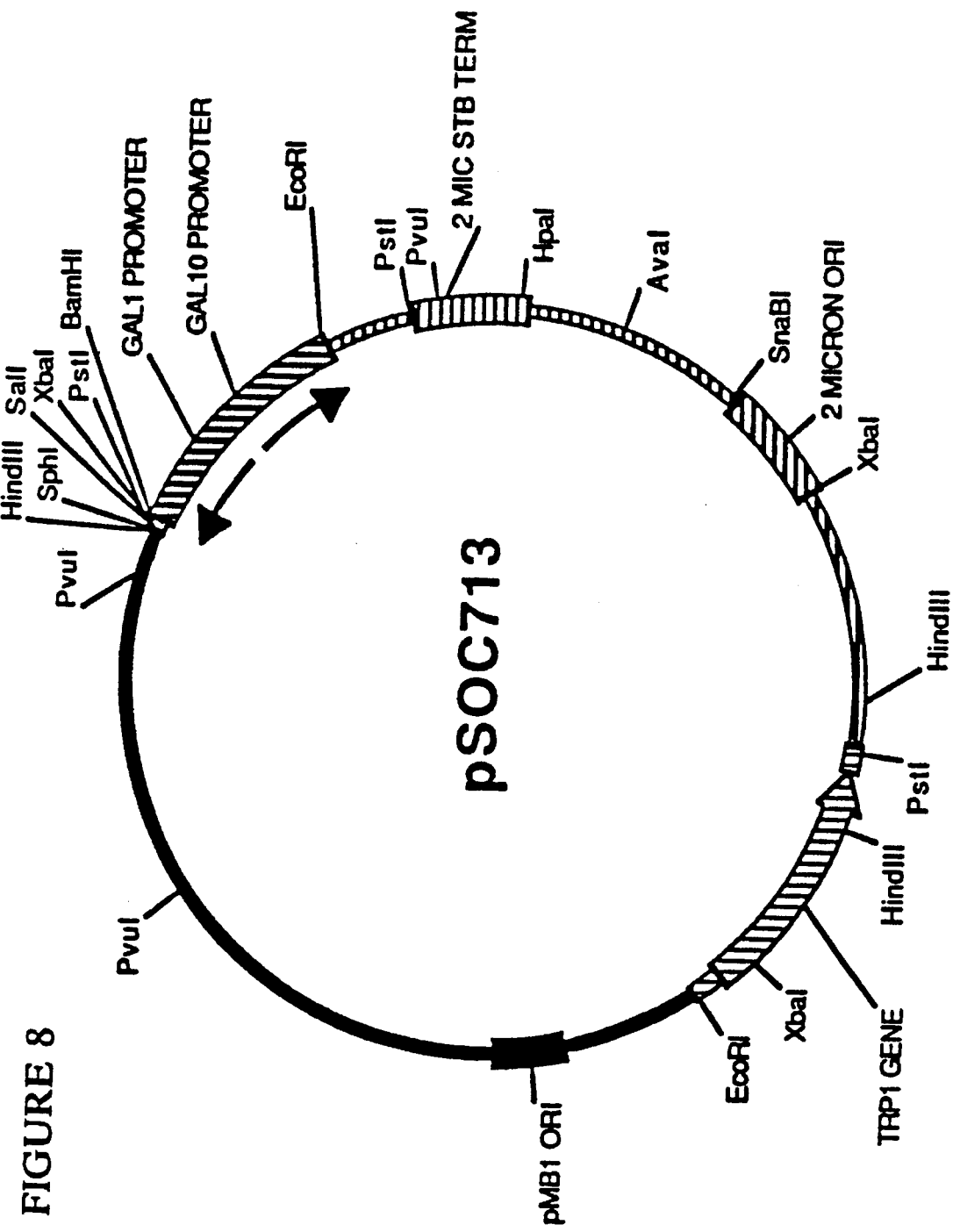

FIG. 8 shows a schematic representation of the vector pSOC713, including a partial restriction enyzme map.

Figure 9:
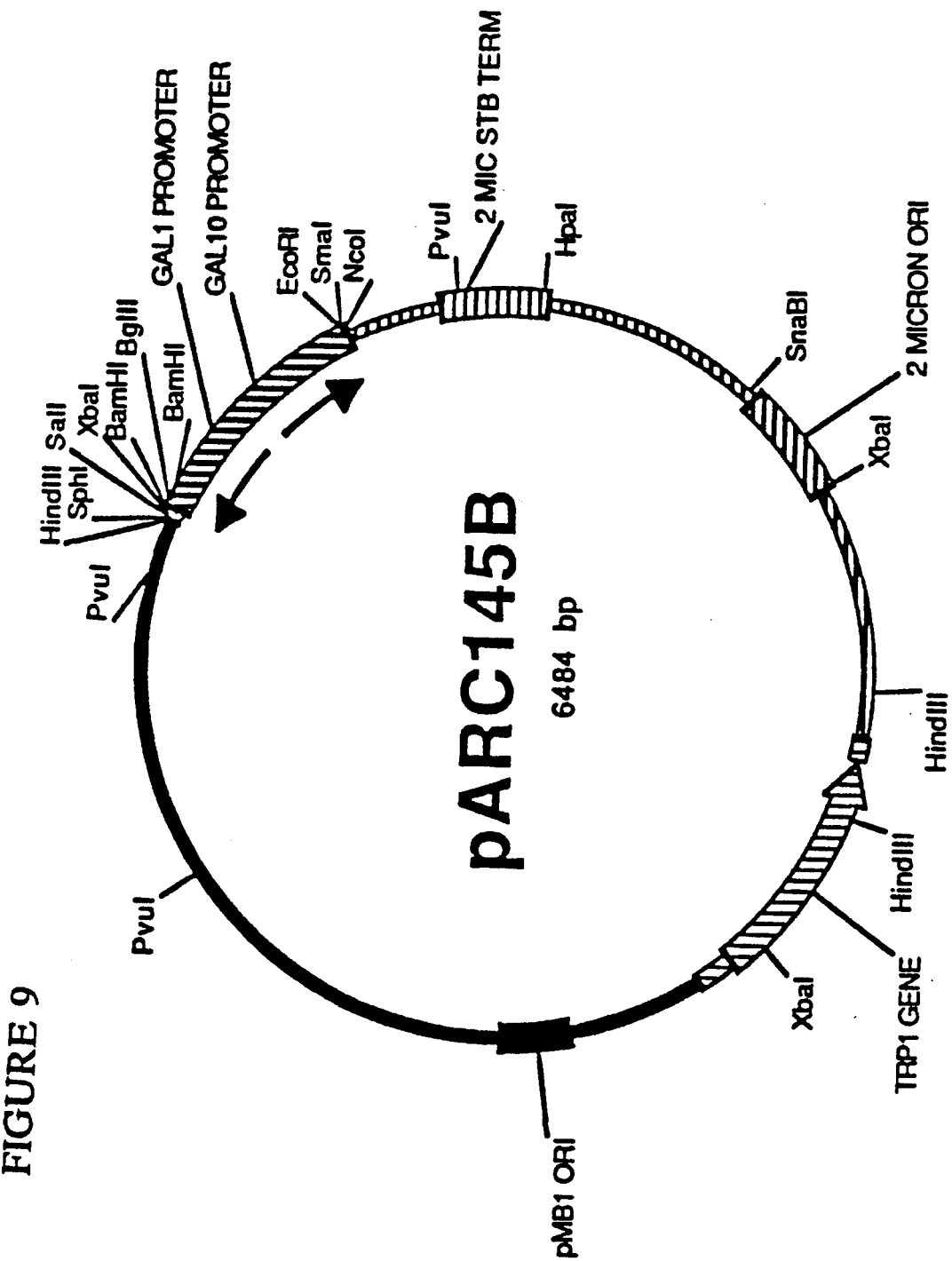

FIG. 9 is a schematic representation of plasmid pARC145B, which is a yeast/*E. coli* shuttle vector for expression of introduced genes in yeast, including a partial restriction enzyme map.

Figure 10:
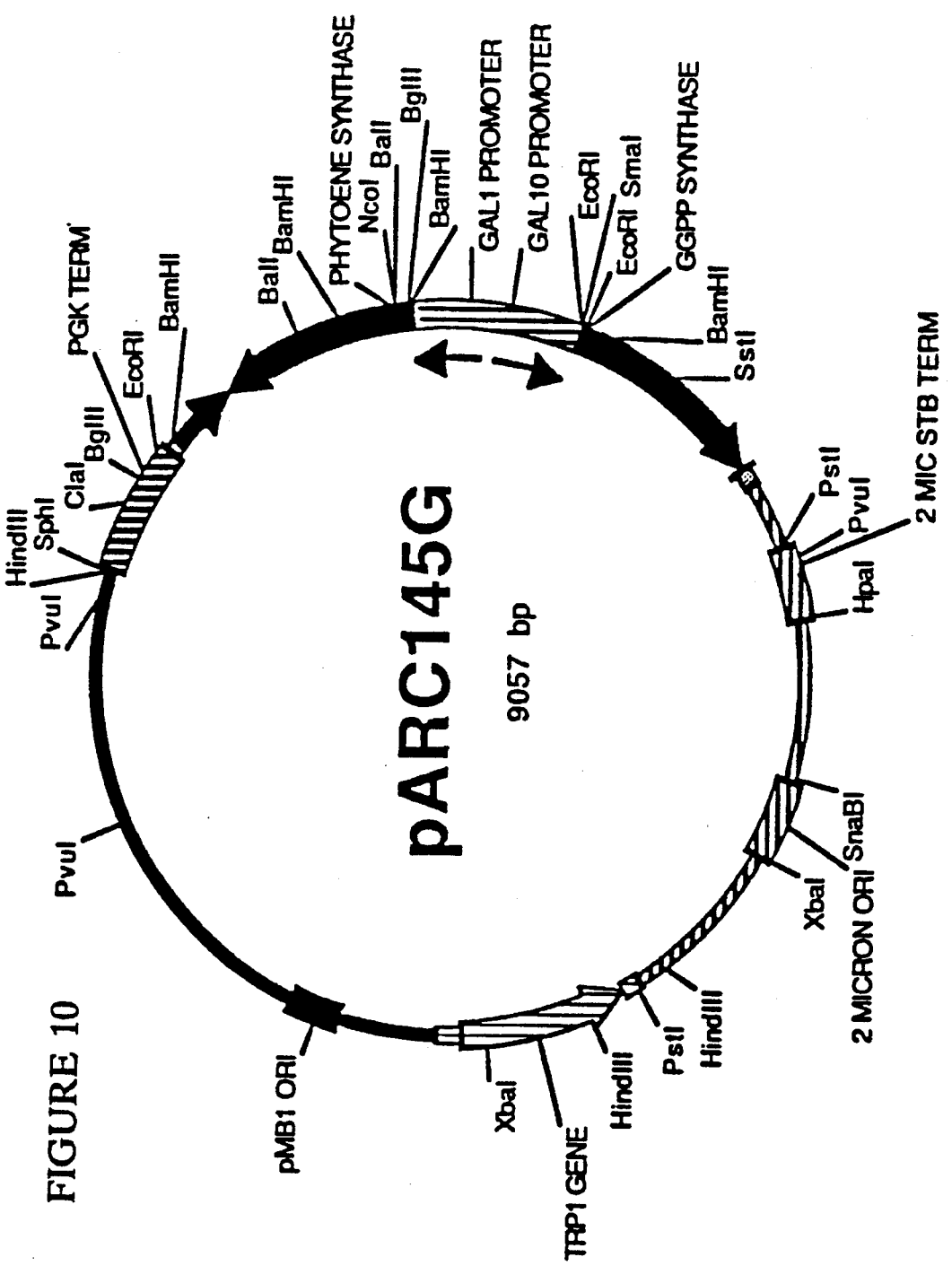

FIG. 10 shows the plasmid vector pARC145G, which is basically plasmid pARC145B above that contains the two preferred genes; i.e., GGPP synthase and phytoene synthase, each operatively linked at their 5' ends to the divergent promoters GAL 10 and GAL 1 . Phytoene synthase also has a PGK terminator at the 3' end.

FIG. 11 illustrates encoded transit peptide sequence (SEQ ID NO:7) and the DNA coding sequence (SEQ ID NO:8) linked to the 5' end of a GGPP synthase or phytoene synthase structural gene for transport of either or both enzymes into tobacco chloroplasts as well as other plant chloroplasts. Stars over nucleotide positions 69 and 72 in this sequence indicate G for T and G for A replacements utilized to introduce an Nar I site.

Figure 12:
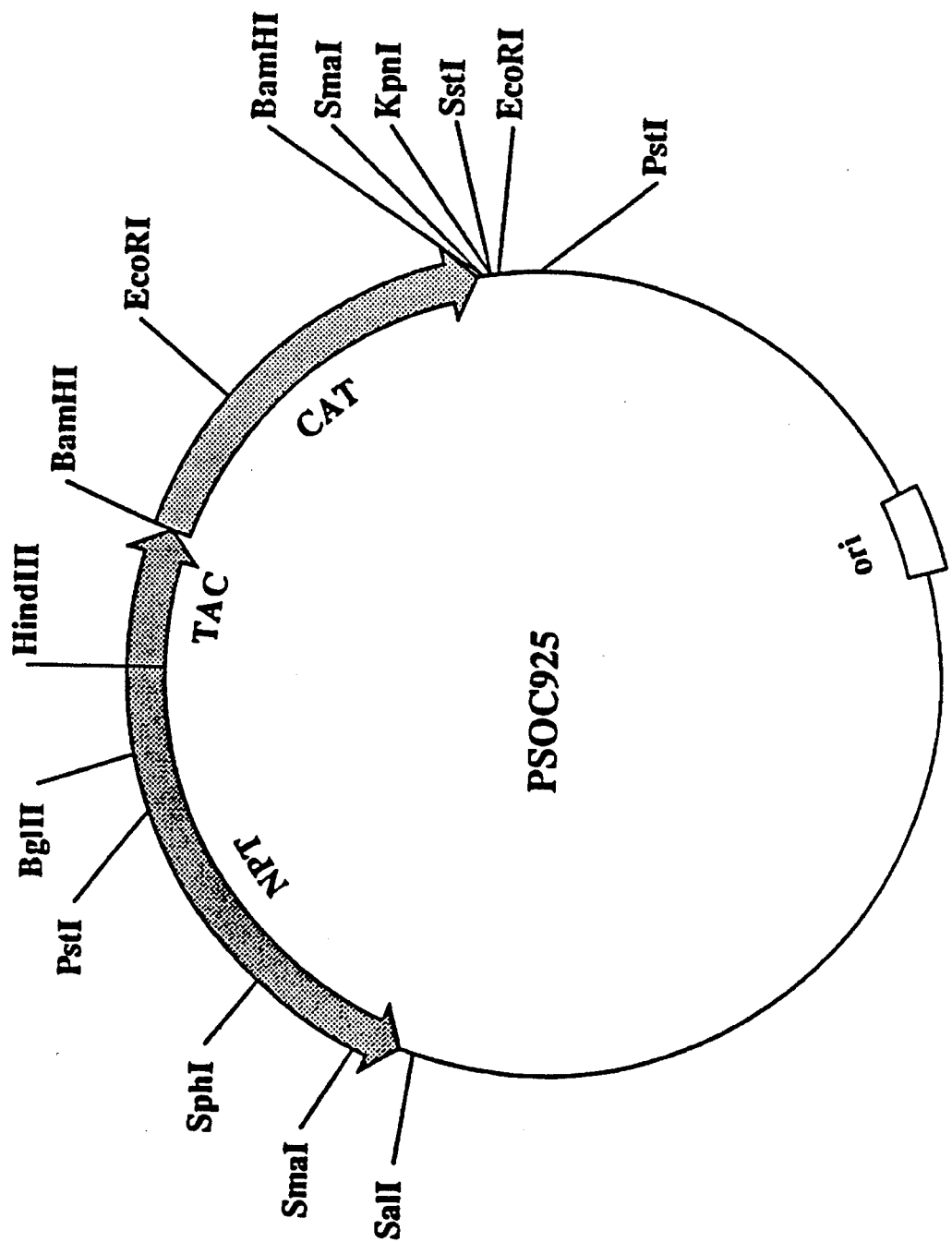

FIG. 12 is a schematic representation of the vector pSOC925, including a partial restriction enzyme map.

DETAILED DESCRIPTION OF THE INVENTION

A. Definition of Terms

Amino acid: All amino acid residues identified herein are in the natural L-configuration. Abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |

-continued

TABLE OF CORRESPONDENCE

| SYMBOL | | |
|---|---|---|
| 1-Letter | 3-Letter | AMINO ACID |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid residue sequences are represented herein by formulae whose left to right orientation is in the conventional direction of amino-terminus to carboxy-terminus.

Expression: The combination of intracellular processes, including transcription and translation undergone by a structural gene to produce a polypeptide.

Expression vector: A DNA sequence that forms control elements that regulate expression of a structural gene when operatively linked to that gene.

Operatively linked or inserted: A structural gene is covalently bonded (ligated) in correct reading frame (where appropriate) to another DNA (or RNA as appropriate) segment, such as to an expression vector so that the structural gene is under the control elements of the expression vector.

Promoter: A recognition site on a DNA sequence or group of DNA sequences that provide an expression control element for a gene and to which RNA polymerase specifically binds and initiates RNA synthesis (transcription) of that gene.

Recombinant DNA molecule: A hybrid DNA sequence comprising at least two nucleotide sequences not normally found together in nature.

Structural gene: A DNA sequence that is expressed as a polypeptide, i.e., an amino acid residue sequence.

Vector: A DNA molecule capable of replication in a cell and/or to which another DNA segment can be operatively linked so as to bring about replication of the attached segment. A plasmid is an exemplary vector.

B. Introduction

Constituting the most widespread group of pigments, carotenoids are present in all photosynthetic organisms, where they are an essential part of the photosynthetic apparatus.

Mevalonic acid, the first specific precursor of all the terpenoids is formed from acetyl-CoA via HMG-CoA (3-hydroxy-3-methylglutaryl-CoA), and is itself converted to isopentenyl pyrophosphate (IPP), the universal isoprene unit. After isomerization of IPP to dimethylallyl pyrophosphate and a series of condensation reactions adding IPP, catalyzed by prenyltransferases, geranylgeranyl pyrophosphate (GGPP) is formed according to the scheme in FIG. 1. The formation of GGPP is the first step in carotenoid biosynthesis.

In the bacterium *Erwinia herbicola*, phytoene has now been found to be formed biosynthetically in a two-step process as shown in FIG. 1. The initial step is the condensation of farnesyl pyrophosphate (FPP) and isopentenyl pyrophosphate (IPP) to form geranylgeranyl pyrophosphate (GGPP). This reaction is catalyzed by the enzyme geranylgeranyl pyrophosphate synthase (GGPP synthase). This first step is immediately followed by a tail-to-tail dimerization of GGPP, catalyzed by the enzyme phytoene synthase, to form phytoene. This pathway thus differs from the pathway reported in published European Application 0 393 690 wherein GGPP is said to form prephytoene pyrophosphate (a cyclopropylene-containing molecule) that thereafter is said to form phytoene.

The present invention relates to these two steps in the carotenoid pathway, and to the adaptation of this pathway by recombinant DNA technology to achieve heretofore unavailable methods and capabilities of phytoene production, particularly in host organisms that do not otherwise synthesize phytoene or that do synthesize phytoene, but do so in relatively small amounts or in specialized locations. The disclosure below provides a detailed description of the isolation of carotenoid synthesis genes from *Erwinia herbicola*, modification of these genes by genetic engineering, and their insertion into compatible plasmids suitable for cloning and expression in *E. coli*, yeasts, fungi and higher plants. Also disclosed are methods for preparation of the appropriate enzymes and the methods for phytoene production in these various hosts.

Plasmid constructs are exemplified for several host systems. However, similar constructs utilizing the genes of this invention are available for virtually any host system without undue experimentation.

A structural gene or isolated purified DNA segment of this invention is often referred to as a restriction fragment bounded by two restriction endonuclease sites and containing a recited number of base pairs. A structural gene of this invention is also defined to include a sequence shown in a figure plus variants and analogs of such genes (described hereinafter), that hybridize non-randomly with a gene shown in the figure under stringency conditions as described hereinafter. Each contemplated gene includes a recited non-randomly-hybridizable variant or analog DNA sequence, encodes GGPP synthase or phytoene synthase and also produces biologically active molecules of the encoded enzymes when suitably transfected into and expressed in an appropriate host.

Polynucleotide hybridization is a function of sequence identity (homology), G+C content of the sequence, buffer salt content, sequence length and duplex melt temperature ($T_m$) among other variables. See, Maniatis et al., *Molecular Cloning*, Cold Spring Harbor Laboratory, Cold Spring Harbor, N.Y. (1982), page 388.

With similar sequence lengths, the buffer salt concentration and temperature provide useful variables for assessing sequence identity (homology) by hybridization techniques. For example, where there is at least 90 percent homology, hybridization is carried out at 68° C. in a buffer salt such as 6XSCC diluted from 20XSSC [Maniatis et al., above, at page 447]. The buffer salt utilized for final Southern blot washes can be used at a low concentration, e.g., 0.1XSSC and at a relatively high temperature, e.g. 68° C., and two sequences will form a hybrid duplex (hybridize). Use of the above hybridization and washing conditions together are defined as conditions of high stringency or highly stringent conditions.

Moderately high stringency conditions can be utilized for hybridization where two sequences share at least about 80 percent homology. Here, hybridization is carried out using 6XSSC at a temperature of about 50°–55° C. A final wash salt concentration of about 1–3XSSC and at a temperature of about 60°–68° C. are used. These hybridization and washing conditions define moderately high stringency conditions.

Low stringency conditions can be utilized for hybridization where two sequences share at least 40 percent homology. Here, hybridization is carried out using 6XSSC at a temperature of about 40°–50° C., with a final wash buffer salt concentration of about 6XSSC at a temperature of about 40°–60° C. These hybridization and washing conditions define low stringency conditions.

An isolated DNA or RNA segment that contains a nucleotide sequence that is at least 80 percent, and more preferably at least 90 percent identical to a DNA sequence for GGPP synthase shown in FIG. 2 (SEQ ID NO:1) or 3 (SEQ ID NO:3) is contemplated by this invention. Such a nucleotide sequence, when present in a host cell as part of a plasmid or integrated into the host genome as described herein, that also hybridizes non-randomly under at least moderately high stringency conditions and expresses biologically active GGPP synthase is contemplated herein as a variant of an illustrated sequence that exhibits substantially the same biological activity.

An isolated DNA or RNA segment that contains a nucleotide sequence that is at least 80 percent, and more preferably at least 90 percent identical to a DNA sequence for phytoene synthase shown in FIG. 4 (SEQ ID NO:5) is also contemplated by this invention. Such a nucleotide sequence, when present in a host cell as part of a plasmid or integrated into the host genome as described herein, that also hybridizes non-randomly under at least moderately high stringency conditions and expresses biologically active phytoene synthase is contemplated herein as a DNA variant of an illustrated sequence that exhibits substantially the same biological activity.

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence; i.e., protein or polypeptide, for which it codes.

Thus, through the well-known redundancy of the genetic code, additional DNA and corresponding RNA sequences can be prepared that encode the same amino acid residue sequences, but that are sufficiently different from a before-discussed gene sequence that the two sequences do not hybridize at high stringency, but do hybridize at moderately high stringency. Furthermore, allelic variants of a structural gene can exist in other *Erwinia herbicola* strains that are also useful, but form hybrid duplex molecules only at moderately high stringency.

A DNA or RNA sequence that (1) encodes an enzyme molecule exhibiting substantially the same biological activity as a GGPP synthase molecule expressed by a DNA sequence of FIG. 2 or 3, (2) hybridizes with a DNA sequence of one of those figures at least at moderately high stringency and (3) shares at least 80 percent, and more preferably at least 90 percent, identity with a DNA sequence of those figures is defined as a DNA variant sequence.

Similarly, a DNA or RNA sequence that (1) encodes a molecule exhibiting substantially the same biological activity as a phytoene synthase molecule expressed by a sequence of FIG. 4, (2) hybridizes with a DNA sequence of that figure at least at moderately high stringency and (3) shares at least 80 percent, and more preferably at least 90 percent, identity with a sequence of those figures is defined as a DNA variant sequence.

Thus, a DNA variant or variant DNA is defined as including an RNA sequence.

Analog or analogous DNA and RNA sequences that encode the above enzyme proteins are also contemplated as part of this invention. A DNA and RNA sequence that encodes an amino acid residue sequence that is at least 40 percent, and more preferably at least 80 percent, and most preferably at least 90 percent, identical to that of an *Erwinia herbicola* GGPP synthase shown in FIGS. 2 or 3 or phytoene synthase shown in FIG. 4 that hybridizes with the structural gene illustrated in FIG. 2 or 3 or FIG. 4, respectively, herein under low stringency hybridization conditions but not at moderately high stringency are also contemplated, and are referred to herein as an "analog of" or "analogous to" a DNA sequence shown in a figure. A polynucleotide that encodes an analogous sequence must also produce functional or biologically active GGPP synthase or phytoene synthase; i.e., an enzyme that converts farnesyl pyrophosphate to GGPP, or GGPP to phytoene, respectively, upon suitable transfection and expression. An analog or analogous DNA sequence is thus also defined as including an RNA sequence.

In comparing DNA sequences of *Erwinia herbicola* and *Erwinia uredovora*, the published European Application 0 393 690 reported no hybridization of DNA from *Erwinia uredovora* with DNA from *Erwinia herbicola* using highly stringent hybridization conditions. Present studies indicate a range of sequence identities of about 60 to about 65 percent between the sequences of that published European application and the sequences disclosed herein. More specifically, identities have been found of about a 59 percent between the two genes for GGPP synthase, and about 64 percent for phytoene synthase (or the same for the enzyme that forms prephytoene pyrophosphate). In spite of the 35 to 40 percent of mismatched base pairs, and the reported non-hybridization at high stringency of the *Erwinia herbicola* and *Erwinia uredovora* DNAs, the reported *Erwinia uredovora* DNA sequences and the *Erwinia herbicola* DNAs discussed herein, and particularly the DNA sequences encoding GGPP synthase and phytoene synthase, are different, but are DNA analogs of each other as the word "analog" is used herein, and as are well known.

Analogous DNA molecules that encode GGPP synthase or phytoene synthase can be obtained from other organisms using hybridization and functionality selection criteria discussed herein.

For example, a microorganism, fungus, alga, or higher plant that is known or can be shown to produce phytoene is utilized as a DNA source. The total DNA of the selected organism is obtained and a genomic library is constructed in a λ phage such as λgt11 using the protocols discussed in Maniatis et al., *Molecular Cloning*, Cold Spring Harbor Laboratory, Cold Spring Harbor, N.Y. (1982) at pages 270–294.

The phage library is then screened under standard protocols using a radiolabeled, nick-translated DNA probe having a sequence of the *Erwinia herbicola* DNA of FIG. 2 or 3, or FIG. 4 and the before-discussed low stringency hybridization conditions. Once the hybridization studies locate the appropriate structural gene, that structural gene DNA segment can be obtained, sequenced, engineered for expression in an appropriate recombinant molecule and shown to produce biologically active GGPP synthase or phytoene synthase as is discussed elsewhere herein.

The above techniques and protocols are well known to workers skilled in molecular biology and need not be discussed further. It is noted, however, that the above procedure can also be used to obtain a variant DNA molecule that encodes GGPP synthase or phytoene synthase inasmuch as DNA molecules that hybridize under conditions of low stringency also include those DNA molecules that hybridize under conditions of high and moderately high stringency.

That a DNA sequence variant or analog encodes a "biologically active" enzyme or an enzyme having "substantially the same biological activity" is determined by whether the variant or analog DNA sequence produces GGPP synthase or phytoene synthase as discussed herein. Thus, a DNA analog or variant sequence that expresses a GGPP synthase or phytoene synthase molecule that converts provided farnesyl phosphate into GGPP or converts GGPP to phytoene is defined as biologically active. Expression of biologically active GGPP synthase or phytoene synthase from a variant or analog DNA sequence can be assayed by the production of GGPP or phytoene, respectively.

A DNA segment of the invention thus includes a DNA sequence that encodes *Erwinia herbicola* GGPP synthase or phytoene synthase of a figure, a DNA variant or an analog thereof. In a preferred embodiment, that DNA segment includes a DNA sequence that encodes the GGPP synthase or phytoene synthase in a DNA segment separate from any other carotenoid-forming enzyme encoding sequences. More preferably, a DNA segment contains the *Erwinia herbicola* GGPP synthase or phytoene synthase structural gene, and is free from a functional phytoene synthase gene (where GGPP alone is to be produced), or phytoene dehydrogenase gene (where phytoene is to be prepared), or another gene whose expression product consumes GGPP or phytoene, or otherwise inhibits GGPP production or production of phytoene. A host transformed with such a DNA segment is also free from a functional gene whose product consumes GGPP or phytoene, or inhibits production of GGPP or phytoene.

C. Genes Encoding Enzymes for Phytoene Biosynthesis

1. Isolation of the carotenoid gene cluster

The plasmid pARC376 contains an approximately 13 kb chromosomal DNA fragment isolated by Perry et al. *J. Bacteriol.*, 168:607 (1986) from the bacterium *Erwinia herbicola* EHO-10 (ATCC 39368) that when transferred into the bacterium *E. coli* causes the *E. coli* cells to produce a yellow pigment. Plasmid pARC376 was referred to by those authors as plasmid pPL376. A restriction map of the pARC376 plasmid showing appropriate restriction sites is shown in FIG. 5.

The structural genes in the plasmid responsible for pigment production are present on a DNA fragment of about 7900 base pairs (bp) that is bounded by the restriction sites Pst I (at about position 4886) and Bgl II (at about position 12349) shown in FIG. 5. There are a total of six relevant genes in this approximately 7900 bp region that cause the *E. coli* cells to produce the carotenoid zeaxanthin diglucoside, which is the final product identified in the carotenoid pathway contained in plasmid pARC376 defined herein.

A flow diagram for the biosynthetic pathway for the production of zeaxanthin diglucoside is shown in FIG. 1. *E. coli* cells, and all cells contemplated as hosts herein, naturally synthesize the isoprenoid intermediate farnesyl pyrophosphate (FPP). The genes for geranylgeranyl phyrophosphate (GGPP) synthase, phytoene synthase, phytoene dehydrogenase-4H, lycopene cyclase, beta-carotene hydroxylase, and zeaxanthin glycosylase are located in the approximately 7900 bp DNA fragment in plasmid pARC376. *E. coli* cells that are transformed with the plasmid pARC376 are able to convert some of the endogenous FPP into carotenoids by utilizing the enzymes encoded on the plasmid.

The following are descriptions of the individual structural genes of this invention responsible for the synthesis of the carotenoid, phytoene, and the recombinant DNA manipulations that have been performed to influence carotenoid biosynthesis in bacteria such as *E. coli*, yeast such as *S. cerevisiae* and higher plants.

2. GGPP Synthase Gene and Plasmid Constructs a. DNA segments

Contemplated by this invention is an isolated, purified DNA segment comprising a nucleotide sequence of at least 850 base pairs that define a structural gene for the *Erwinia herbicola* enzyme GGPP synthase. A typical, useful DNA segment contains about 850 to about 1150 base pairs, whereas a more preferred DNA segment contains about 850 to about 1000 base pairs. The native sequence includes about 924 bp. Larger DNA segments are also contemplated and are discussed hereinafter.

An approximately 1153 bp fragment that extends from the Bgl II (about 12349) site to the Eco RV (about 11196) site of plasmid pARC376 is shown in FIG. 5. A preferred structural gene for GGPP synthase is within the about 1153 bp Bgl II to Eco RV restriction fragment shown in FIG. 5 and contains the previously mentioned native structural gene of about 924 bp. This structural gene is within the approximately 1029 bp Nco I-Eco RV restriction fragment of plasmid pARC417BH.

Surprisingly it has been found that a recombinant structural gene that encodes an amino-terminal truncated version of this enzyme in which the amino-terminal thirteen residues of the native enzyme were deleted and were replaced by four extraneous amino acid residues from the plasmid pARC306A vector was more active (about two times) than was a recombinantly produced enzyme having the encoded, native thirteen amino-terminal residues. This more active enzyme is encoded by the structural GGPP synthase gene containing about 1000 bp shown in FIG. 3, and is within the approximately 1150 bp segment Nco I-Pvu II restriction fragment of plasmid pARC489B.

Still more surprisingly, it has also been found that truncation of the carboxy-terminus of the GGPP synthase molecule made the enzyme still more active. Thus, use of a GGPP synthase structural gene of FIG. 3 from which the 3' Bal I-Eco RV fragment was removed provided the most active GGPP synthase found. This structural gene of about 850 bp is within the approximately 1000 bp Nco I-Pvu II restriction fragment of plasmid pARC489D. This GGPP synthase gene is most preferred herein.

Details of the above work are described hereinafter.

The DNA sequence 1 from *Erwinia uredovora* in EP 0 393 690 is said there to encode the gene for converting prephytoene pyrophosphate to phytoene. The DNA sequence of that European application has about 59 percent identify with the GGPP synthase illustrated herein. That *Erwinia uredovora* DNA sequence 1 is an analog of the before-discussed GGPP synthase gene, and can also be used herein for preparing GGPP.

(b) Recombinant DNA molecules

Also useful in this invention are recombinant DNA molecules comprising a vector operatively linked to an exogenous DNA segment defining a structural gene capable of expressing the enzyme GGPP synthase, as described above, and a promoter suitable for driving the expression of the gene encoding the enzyme in a compatible host organism. The vector and promoter are as described elsewhere herein. Particularly preferred plasmid vectors include pARC417BH, pARC489B, pARC489D and pARC145G.

3. Phytoene Synthase Gene and Plasmid Construct (a) DNA segments

An isolated, purified DNA segment comprising a nucleotide sequence of at least about 927 base pairs that define a structural gene for the *Erwinia herbicola* enzyme phytoene synthase participates in this invention by providing phytoene (from GGPP) as an intermediate to production of zeaxanthin and its diglucoside, as well as to production of the plant carotenoids lutein and neoxanthin. This structural gene typically contains about 1000 to about 1250 bp including the 927 bp of the native sequence, but can also contain a greater number as discussed hereinafter. The structural gene for phytoene synthase lies between positions 6383 and 5457 of plasmid pARC376 (FIG. 5).

A phytoene synthase gene useful herein at least includes a sequence shown in FIG. 4. In preferred practice, the structural gene also includes an upstream sequence shown in FIG. 4 from about position 8 (Bgl II site) through about position 15.

A preferred phytoene synthase gene is within the about 1112 bp Nco I-Eco RI fragment of plasmid pARC285. Also included within that about 1112 bp segment is the approximately 1040 bp Nco I-Bam HI fragment that also encodes the desired structural gene.

The most preferred structural gene includes a nucleotide base sequence in FIG. 4 from about base 8 to about base 1040, and contains about 1030 bp. This most preferred gene is contained in the approximately 1176 base pair sequence of the Hpa I to Bam HI restriction sites and approximately 1238 bp Pvu II-Eco RI fragments present in the plasmid pARC140N, as well as in the approximately 1088 bp sequence of the Bgl II-Eco RI fragment of plasmid pARC140R.

A particularly preferred DNA segment is the approximately 2009 base pair Xba I-Xba I fragment present in plasmid pATC1615. This fragment contains an approximately 1242 base pair portion that encodes a chloroplast transit peptide of tobacco ribulose bis-phosphate carboxylase-oxygenase (hereinafter referred to as a chloroplast transit peptide) (about 177 bp) operatively linked in frame to the 5' end of the approximately 1065 bp Sph I-Sal I fragment, derived from plasmid pARC376 and modified as described in Example 9. That approximately 1242 bp fragment is flanked at its 5' end by an about 450 bp CaMV 35S promoter sequence and at its 3' end by an about 300 bp NOS polyadenylation sequence.

A further particularly preferred DNA segment is the approximately 3025 bp Hind III-Hind III fragment of plasmid pATC1620. This fragment contains an approximately 1242 bp portion that encodes the above chloroplast transit peptide operatively linked in frame to the 5' end of the approximately 1065 bp Sph I-Sal I fragment described in Example 9. That approximately 1242 bp fragment is flanked at its 5' end by an about 1483 bp NOS promoter sequence and at its 3' end by an about 300 bp NOS polyadenylation sequence.

The approximately 2009 bp Xba I-Xba I fragment present in plasmid pATC1615 and the approximately 3025 base pair Hind III-Hind III fragment present in plasmid pATC1620 can be used for expression of phytoene synthase in higher plants and transport of the expressed phytoene synthase into chloroplasts of higher plants such as tobacco. Infection of a higher plant such as tobacco with *A. tumefaciens* containing either plasmid pATC1615 or plasmid pATC1620 caused genomic incorporation of DNA for the promoter, transit peptide-phytoene synthase and NOS polyadenylation sequence. Such incorporation enables the resulting plants to produce increased amount of phytoene synthase and thereby phytoene, when the plants are maintained for a sufficient time period such as at least to the production of leaves. This maintenance period also permits enhanced lutein synthesis when compared to normal (native), non-transformed plants of the same type. The transformed plants also exhibit an increase in the amount of chlorophyll.

The approximately 2009 bp Xba I-Xba I fragment present in plasmid pATC1615 and the approximately 3025 bp Hind III-Hind III fragment present in plasmid pATC1620 can be further modified to remove the about 177 base pair chloroplast transit peptide. Transformation of higher plants with these modified gene segments incorporates DNA for the promoter, phytoene synthase and NOS polyadenylation sequence. Such incorporation enables the resulting plants to produce increased amounts of phytoene synthase and therefore phytoene in the plant cytoplasm, leading to an increase in the amount of lutein in these plants, when compared to normal (native), non-transformed plants of the same type.

The phrase "same type" is used herein to mean a plant of the same cross as or a clone of the transformed plant. Where alleic variations among siblings of a cross are small, as with extensively inbred plants, comparisons between siblings can be used or an average arrived at using several siblings. Otherwise, clones are preferred for the comparison.

EP 0 393 690 identifies its own *Erwinia uredovora* DNA sequence 5 as encoding an enzyme that converts GGPP into prephytoene pyrophosphate. Sequence 5 of that European application is about 64 percent identical to the before-discussed phytoene synthase gene, and that *Erwinia uredovora* gene or any phytoene synthase structural gene can be used herein for the synthesis of phytoene.

(b) Recombinant DNA molecules

A recombinant DNA molecule, comprising a vector operatively linked to an exogenous DNA segment defining a structural gene capable of expressing the enzyme phytoene synthase, as discussed above, and a promoter suitable for driving the expression of the gene in a compatible host organism, is also contemplated by this invention. The vector and promoter of this recombinant molecule are also as are discussed herein. Particularly preferred plasmid vectors include pARC285, pARC140N and pARC145G.

4. DNA Size

The previously described DNA segments are noted as having a minimal length, as well as total overall lengths. That minimal length defines the length of a DNA segment having a sequence that encodes a particular protein enzyme. Inasmuch as the coding sequences for each of the two genes disclosed herein are illustrated in the accompanying figures, isolated DNA segments, variants and analogs thereof can be prepared by in vitro mutagenesis, as described in the examples, that begin at the initial ATG codon for a gene and end at or just downstream of the stop codon for each gene. Thus, a desired restriction site can be engineered at or upstream of the initiation codon, and at or downstream of the stop codon so that shorter structural genes than most of those discussed above can be prepared, excised and isolated.

As is well known in the art, so long as the required DNA sequence is present, (including start and stop signals), additional base pairs can be present at either end of the segment and that segment can still be utilized to express the protein. This, of course, presumes the absence in the segment of an operatively linked DNA sequence that represses expression, expresses a further product that consumes the protein desired to be expressed, expresses a product that consumes a wanted reaction product produced by that desired protein, or otherwise interferes with the structural gene of the DNA segment.

Thus, so long as the DNA segment is free of such interfering DNA sequences, a DNA segment of the invention can be 2,000–15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

Example 5b illustrates that a DNA segment of several thousand base pairs that contains the structural genes for GGPP synthase and phytoene synthase can be used to produce phytoene. The DNA segments used contained structural genes for both GGPP synthase and phytoene synthase, as well as all of the other structural genes for zeaxanthin preparation, with the gene for phytoene dehydrogenase-4H, which consumes phytoene, impaired so as to produce an inactive phytoene dehydrogenase enzyme.

5. Construction of Plasmids a. DNA segments

DNA segments that encode the before-described enzyme proteins can be synthesized by chemical techniques, for example, the phosphotriester method of Matteucci et al., *J. Am. Chem. Soc.*, 103:3185 (1981). (The disclosures of the art cited herein are incorporated herein by reference.) Of course, by chemically synthesizing the coding sequence, any desired modifications can be made simply by substituting the appropriate bases for those encoding the native amino acid residue sequence. However, DNA segments including sequences discussed previously are preferred.

Furthermore, DNA segments containing structural genes encoding the enzyme proteins can be obtained from recombinant DNA molecules (plasmid vectors) containing those genes. For instance, the plasmid type recombinant DNA molecules pARC417BH, pARC489B, pARC489D, pARC285, and pARC140N each contain DNA sequences encoding different portions of the GGPP synthase and phytoene synthase proteins and together possess the entire sequence of DNA necessary for expression of either protein in biologically active form. Plasmid pARC145G contains DNA segments encoding both enzymes. Plasmids pARC417BH, pARC489B, pARC489D, pARC285, pARC140N and pARC145G have been deposited pursuant to Budapest Treaty requirements with the American Type Culture Collection, (ATCC) 12301 Parklawn Drive, Rockville, Md. 20852 on Feb. 26, 1990 and were assigned the following respective accession numbers 40755, 40758, 40757, 40756, 40759, and 40753.

A DNA segment that includes a DNA sequence encoding GGPP synthase or phytoene synthase can be prepared by excising and operatively linking appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules is preferred, although molecules having blunt termini are also contemplated.

Ribonucleic acid (RNA) equivalents of the above described DNA segments are also contemplated.

b. Recombinant DNA molecules

The recombinant DNA molecules of the present invention can be produced by operatively linking a vector to a DNA segment of the present invention to form a plasmid such as those discussed and deposited herein. Particularly preferred recombinant DNA molecules are discussed in detail in the examples, hereafter. Vectors capable of directing the expression of GGPP synthase and/or phytoene synthase genes are referred to herein as "expression vectors".

The expression vectors described above contain expression control elements including the promoter. The polypeptide coding genes are operatively linked to the expression vector to allow the promoter sequence to direct RNA polymerase binding and expression of the desired polypeptide coding gene. Useful in expressing the polypeptide coding gene are promoters which are inducible, vital, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chua et al., *Science*, 244:174–181 (1989).

The choice of which expression vector and ultimately to which promoter a polypeptide coding gene is operatively linked depends directly, as is well known in the art, on the functional properties desired, e.g. the location and timing of protein expression, and the host cell to be transformed, these being limitations inherent in the art of constructing recombinant DNA molecules. However, a vector useful in practicing the present invention is capable of directing the replication, and preferably also the expression (for an expression vector) of the polypeptide coding gene included in the DNA segment to which it is operatively linked.

In one preferred embodiment, a vector includes a prokaryotic replicon; i.e., a DNA sequence having the ability to direct autonomous replication and maintenance of the recombinant DNA molecule extrachromosomally in a prokaryotic host cell, such as a bacterial host cell, transformed therewith. Such replicons are well known in the art.

Those vectors that include a prokaryotic replicon can also include a prokaryotic promoter region capable of directing the expression (transcription and translation) of the GGPP synthase or phytoene synthase genes in a host cell, such as *E. coli*, transformed therewith. Promoter sequences compatible with bacterial hosts are typically provided in plasmid vectors containing one or more convenient restriction sites for insertion of a DNA segment of the present invention. Typical of such vector plasmids are pUC8, pUC9, and pBR329 available from Biorad Laboratories, (Richmond, Calif.) and pPL and pKK223-3 available from Pharmacia, Piscataway, N.J. A particularly preferred promoter for use in prokaryotic cells such as *E. coli* is the Rec 7 promoter that is present in plasmid vector pARC306A and is inducible by exogenously supplied nalidixic acid.

Expression vectors compatible with eukaryotic cells, preferably those compatible with yeast cells or more preferably those compatible with cells of higher plants, are also contemplated herein. Such expression vectors can also be used to form the recombinant DNA molecules of the present invention. Vectors for use in yeasts such as *S. cerevisiae* can be episomal or integrating, as is well known. Eukaryotic cell expression vectors are well known in the art and are available from several commercial sources.

Normally, such vectors contain one or more convenient restriction sites for insertion of the desired DNA segment and promoter sequences. Exemplary promoters for use in *S. cerevisiae* include the *S. cerevisiae* phosphoglyceric acid kinase (PGK) promoter and the divergent promoter GAL 10 and GAL 1 .

Typical expression vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other expression vector systems are known to function in plants including pCaMVCN transfer control vector described by Fromm et al., *Proc. Natl. Acad. Sci. USA*, 82:5824 (1985). Plasmid pCaMVCN (available from Pharmacia, Piscataway, N.J.) includes the cauliflower mosaic virus CaMV 35S promoter. The introduction of genes into higher plants is discussed in greater detail hereinafter.

The use of retroviral expression vectors to form the recombinant DNAs of the present invention is also contemplated. As used herein, the term "retroviral expression vector" refers to a DNA molecule that includes a promoter sequence derived from the long terminal repeat (LTR) region of a retrovirus genome.

Since some ultimate carotenoid products such as β-carotene can be associated with food production and coloration, the retroviral expression vector is preferably replication-incompetent in eukaryotic cells. The construction and use of retroviral vectors has been described by Verma, PCT Publication No. WO87/00551, and Cocking et al, *Science*, 236:1259–62 (1987).

In preferred embodiments, the expression vector used to express the polypeptide coding gene includes a selection marker that is effective in a plant cell, preferably a drug resistance selection marker. One preferred drug resistance marker is the gene whose expression results in kanamycin resistance, i.e., the chimetic gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (1988). Another preferred marker is the assayable chloramphenicol acetyltransferase (CAT) gene from the transposon Tn9.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

c. Introducing genes into higher plants

Methods for introducing polypeptide coding genes into higher, multicelled plants include Agrobacterium-mediated plant transformation, protoplast transformation, gone transfer into pollen, injection into reproductive organs and injection into immature embryos. Each of these methods has distinct advantages and disadvantages. Thus, one particular method of introducing genes into a particular plant species may not necessarily be the most effective for another plant species, but it is well known which methods are useful for a particular plant species.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated expression vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In those plant species where Agrobacterium-mediated transformation is efficient, it is the method of choice because of the facile and defined nature of the gene transfer. However, few monocots appear to be natural hosts for Agrobacterium, although transgenic plants have been produced in asparagus using Agrobacterium vectors as described by Bytebier et al., *Proc. Natl. Acad. Sci. U.S.A.*, 84:5345 (1987). Therefore, commercially important cereal grains such as rice, corn, and wheat must be transformed using alternative methods.

Higher plants have the ability to produce carotenoids such as lutein. The site of synthesis for all plant carotenoids is in the chloroplast. Carotenoid biosynthesis is highly regulated in plants. Masoner et al., *Planta* 105:267 (1972); Frosch et al., *Planta* 148:279 (1980); Mohr, *Photosynthesis V. Chloroplast Development*, pp. 869–883 (1981); Oelmueller et al., *Planta* 164:390 (1985); Harpster et al., *Physiol. plant.* 64:147 (1985); Steinmueller et al., *Molecular Form and Function of the Plant Genome*, pp. 277–290 (1986). Therefore, the ability to use recombinant DNA technology to increase endogenous carotenoid biosynthesis is questionable unless a novel approach is used. However, using the genes for GGPP synthase and phytoene synthase to catalyze phytoene synthesis in the cytoplasm is a viable approach, even though carotenoids are not naturally produced in the cytoplasm.

Agrobacterium-mediated transformation of leaf disks and other tissues appears to be limited to plant species that Agrobacterium naturally infects. Thus, Agrobacterium-mediated transformation is most efficient in dicotyledonous plants. However, as mentioned above, the transformation of asparagus using Agrobacterium can also be achieved. See, for example, Bytebier, et al., *Proc. Natl. Acad. Sci.,* 84:5345 (1987).

Transformation of plant protoplasts can be achieved using methods based on calcium phosphate precipitation, polyethylene glycol treatment, electroporation, and combinations of these treatments. See, for example, Potrykus et al., *Mol. Gen. Genet.,* 199:183 (1985); Lorz et al., *Mol. Gen. Genet.,* 199:178 (1985); Fromm et al., *Nature,* 319:791 (1986); Uchimiya et al., *Mol. Gen. Genet.,* 204:204 (1986); Callis et al., *Genes and Development,* 1:1183 (1987); and Marcotte et al., *Nature,* 335:454 (1988).

Application of these systems to different plant species depends upon the ability to regenerate that particular plant species from protoplasts. Illustrative methods for the regeneration of cereals from protoplasts are described in Fujimura et al., *Plant Tissue Culture Letters,* 2:74 (1985); Toriyama et al., *Theor Appl. Genet.,* 73:16 (1986); Yamada et al., *Plant Cell Rep.,* 4:85 (1986); Abdullah et al., *Biotechnology,* 4:1087 (1986).

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology,* 6:397 (1988). In addition, "particle gun" or high-velocity microprojectile technology can be utilized. Using such technology, DNA is carried through the cell wall and into the cytoplasm on the surface of small metal particles as described in Klein et al., *Nature,* 327:70 (1987); Klein et al., *Proc. Natl. Acad. Sci. U.S.A.,* 85:8502 (1988); and McCabe et al., *Biotechnology,* 6:923 (1988). The metal particles penetrate through several layers of cells and thus allow the transformation of cells within tissue explants.

Metal particles have been used to successfully transform corn cells and to produce fertile, stably transformed tobacco and soybean plants. Transformation of tissue explants eliminates the need for passage through a protoplast stage and thus speeds the production of transgenic plants.

DNA can also be introduced into plants by direct DNA transfer into pollen as described by Zhou et al., *Methods in Enzymology,* 101:433 (1983); D. Hess, *Intern Rev. Cytol.,* 107:367 (1987); Luo et al., *Plant Mol. Biol. Reporter,* 6:165 (1988). Expression of polypeptide coding genes can be obtained by injection of the DNA into reproductive organs of a plant as described by Pena et al., *Nature,* 325:274 (1987). DNA can also be injected directly into the cells of immature embryos and the rehydration of dessicated embryos as described by Neuhaus et al., *Theor. Apl. Genet.,* 75:30 (1987); and Benbrook et al., in *Proceedings Bio Expo 1986,* Butterworth, Stoneham, Mass., pp. 27–54 (1986).

The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by Agrobacterium from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.,* 80:4803 (1983).

This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil or other media to allow the production of roots. These procedures vary depending upon the particular plant species employed, such variations being well known in the art.

A plant of the present invention containing GGPP synthase and phytoene synthase, is cultivated using methods well known to one skilled in the art. Any of the transgenic plants of the present invention can be cultivated to isolate the desired carotenoid products they contain.

After cultivation, the transgenic plant is harvested to recover the carotenoid product. This harvesting step can consist of harvesting the entire plant, or only the leaves, or roots of the plant. This step can either kill the plant or if only a non-essential portion of the transgenic plant is harvested can permit the remainder of the plant to continue to grow.

In preferred embodiments this harvesting step further comprises the steps of:

(i) homogenizing at least a carotenoid-containing portion of the transgenic plant to produce a plant pulp and using the carotenoid-containing pulp directly, as in dried pellets or tablets as where an animal food is contemplated; or (ii) extracting the carotenoid from the plant pulp with an appropriate solvent such as an organic solvent or by supercritical extraction [Favati et al., *J. Food Sci.,* 53:1532 (1988) and the citations therein] to produce a carotenoid-containing liquid solution or suspension: and (iii) isolating the carotenoid from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of the carotenoid of interest, trace amounts of precursors, cellular particles and cytosol contents. This pulp can be dried and compressed into pellets or tablets and eaten or otherwise used to derive the benefits, or the pulp can be subjected to extraction procedures.

The carotenoid can be extracted from the plant pulp produced above to form a carotenoid-containing solution or suspension. Such extraction processes are common and well known to one skilled in this art. For example, the extracting step can consist of soaking or immersing the plant pulp in a suitable solvent. This suitable solvent is capable of dissolving or suspending the carotenoid present in the plant pulp to produce a carotenoid containing solution or suspension. Solvents useful for such an extraction process are well known to those skilled in the art and include water, several organic solvents and combinations thereof such as methanol, ethanol, isopropanol, acetone, acetonitrile, tetrahydrofuran (THF), hexane, and chloroform. A vegetable oil such as peanut, corn, soybean and similar oils can also be used for this extraction.

Isolation (harvesting) of phytoene from bacteria, yeasts, fungi and other lower organisms is illustrated hereinafter using *A. tumefaciens* and *E. coli.* Broadly, cells transfected with structural genes for GGPP synthase and phytoene synthase are grown under suitable conditions for a period of time sufficient for phytoene to be synthesized. The phytoene-containing cells, preferably in dried form, are then lysed chemically or mechanically, and the phytoene is extracted from the lysed cells using a liquid organic solvent, as described before, to form a phytoene-containing liquid solution or suspension. The phytoene is thereafter isolated from the liquid solution or suspension by usual means such as chromatography.

The carotenoid is isolated from the solution or suspension produced above using methods that are well known to those skilled in the art of carotenoid isolation. These methods include, but are not limited to, purification procedures based on solubility in various liquid media, chromatographic techniques such as column chromatography and the like.

D. Methods for Preparing Phytoene Synthesis Enzymes

1. Introduction a. Transformed cells and cultures

The present invention also relates to host cells transformed with recombinant DNA molecules of the present invention, preferably recombinant DNA capable of expressing GGPP synthase and membrane-bound (or soluble) phytoene synthase. The host cells can be either prokaryotic or eukaryotic. Bacterial cells are preferred prokaryotic host cells and typically are a strain of *E. coli* such as, for example the *E. coli* strain HB101, available from BRL Life Technologies, Inc., Gaithersburg, Md. Preferred eukaryotic host cells include yeast and plant cells, preferably cells from higher plants. Preferred eukaryotic host cells include *S. cerevisiae* cells such as YPH499 obtained from Dr. Phillips Hieter, Johns Hopkins University, Baltimore, Md., discussed in Example 6.

Transformation of appropriate cell hosts with a recombinant DNA molecule of the present invention is accomplished by well known methods that typically depend on the type of vector used. With regard to transformation of prokaryotic host cells, see, for example, Cohen et al., *Proc. Natl. Acad. Sci. USA*, 69:2110 (1972); and Maniatis et al., *Molecular Cloning, A Laboratory Manual,* Cold Spring Harbor Laboratory, Cold Spring Harbor, N.Y. (1982). With regard to transformation of plant cells with retroviral vectors containing recombinant DNAs, see, for example, Verma, PCT Publication WO 87/00551, 1987, who isolated protoplasts from plant tissue, and inserted the retroviral genome in proviral (double stranded) form into the genome of the protoplasts. The transformed protoplasts were developed into callus tissue and then regenerated into transgenic plants. Plants derived from the protoplasts and their progeny carry the genetic material of the recombinant retroviral vector in their genomes and express the protein product.

Successfully transformed cells, i.e., cells that contain a recombinant DNA molecule of the present invention, can be identified by well known techniques. For example, cells resulting from the introduction of a recombinant DNA of the present invention can be cloned to produce colonies. Cells from those colonies can be harvested, lysed and their DNA content examined for the presence of the recombinant DNA using a method such as that described by Southern, *J. Mol. Biol.*, 98:503 (1975) or Berent et al., *Biotech.*, 3:208 (1985).

In addition to directly assaying for the presence of recombinant DNA, successful transformation can be confirmed by well known immunological methods when the recombinant DNA is capable of directing the expression of specific protein antigens. For example, cells successfully transformed with an expression vector can produce proteins displaying GGPP synthase or phytoene synthase antigenicity.

Identifying successful transformation of *E. coli* in this invention is relatively easy for carotenoids, except phytoene. Carotenoid-containing colonies formed are usually characterized by colored pigment formation. Phytoene, however, is colorless. Identification of phytoene-containing colonies is discussed hereinafter.

b. Methods for producing enzymes

A method is contemplated by this invention for preparing the enzymes GGPP synthase and phytoene synthase. This method comprises initiating a culture, in a nutrient medium, of transformed prokaryotic or eukaryotic host cells. The host cells are transformed with a recombinant DNA molecule containing a compatible expression vector operatively linked to the before-described exogenous DNA segment defining the structural gene for GGPP synthase and phytoene synthase, as appropriate. This invention further comprises cultures maintained for a time period sufficient for the host cells to express the GGPP synthase and phytoene synthase protein molecules, which proteins can be recovered in purified form if desired.

Nutrient media useful for culturing transformed host cells are well known in the art and can be obtained from several commercial sources.

E. Methods for Preparing Phytoene

1. Introduction

Phytoene can be produced by a method that includes initiating a culture, in a nutrient medium, of prokaryotic or eukaryotic host cells transformed with a recombinant DNA molecule(s) for phytoene expression. In higher plants, the nutrient medium is supplied by the plant itself, and the initiated culture is the germinated seed, protoplast or even a grafted explant from a prior culture.

This recombinant DNA molecule contains an expression system that comprises one or more expression vectors compatible with host cells, operatively linked to an exogenous DNA segment, comprising (i) a nucleotide base sequence corresponding to a sequence defining a structural gene for GGPP synthase as discussed before, and (ii) a nucleotide base sequence corresponding to a sequence defining a structural gene for phytoene synthase as also discussed before, and maintaining the culture for a time period sufficient for the cells to express phytoene. The particularly preferred expression vector plasmid pARC145G contains structural genes for both GGPP synthase and phytoene synthase, and produces phytoene in *S. cerevisiae*.

In certain preferred embodiments, the structural genes for both GGPP synthase and phytoene synthase may or may not be contained operatively linked in a single expression vector, preferably under the control of the same promoter although a separate promoter for each gene can be used, as where yeast cells are the host cells. The order of expression of the two structural genes is not important so the structural gene for GGPP synthase can be located 5' (upstream) from the structural gene for phytoene synthase, or vice versa. Yeast and plants require a separate promoter for each gene, although they can be the same.

In higher plants, the transformed elements are so manipulated as to permit them to mature into soil-cultivated plants, as well as plants that are cultivated hydroponically or in other soil-free media such as lava rock, crushed coral, sphagnum moss and the like.

Methods not utilizing tissue culture procedures are also contemplated, for example, using Agrobacterium-mediated vectors to produce transgenic plants from seeds.

F. Examples

The following examples are intended to illustrate, but not limit, the scope of the invention.

All recombinant DNA techniques were performed according to standard protocols as described in Maniatis et al., (Maniatis) *Molecular Cloning, A Laboratory Manual,* Cold Spring Harbor Laboratory, Cold Spring Harbor, N.Y. (1982), except where noted. All restriction enzymes and other enzymes were used according to the supplier's instructions. DNA sequencing was performed on M13 single-stranded DNA using a modification of the basic dideoxy method of Sanger et al, *Proc. Natl. Acad. Sci. U.S.A.,* 74:5463–7 (1977). A sequencing kit from BRL Life Technologies, Inc., Gaithersburg, Md. was used. The DNA sequence was analyzed on the IG Suite software from Intelligenetics Corp.

Enzyme assays for GGPP synthase and phytoene synthase in *E. coli* or *Saccharomyces cerevisiae* were performed according to the protocol provided in Example 2j.

Carotenoids were extracted and analyzed by high performance liquid chromatography (HPLC) from both *E. coli* or *S. cerevisiae* according to the protocol provided in Example 5. The identity of zeaxanthin diglucoside was confirmed by mass spectroscopy performed according to the protocol provided in Example 5. The identity of zeaxanthin was confirmed by mass spectroscopy. The identification of the other carotenoids was confirmed by elution from HPLC, UV-Visible spectral analysis, and comparison with known standards of phytoene, lycopene, and beta-carotene.

The method for production in *E. coli* of the proteins in *E. coli* encoded by the different genes, using the inducible Rec 7 promoter system in the plasmid pARC306A, is described in Example 2i. These proteins were used in the enzyme assays described. This protocol was also used to produce sufficient amounts of the proteins from which the N-terminus of the protein was determined.

Two different approaches for inducing phytoene production in *E. coli* are described illustratively in Example 5. In the first, a plasmid is constructed that contains both the GGPP synthase gene and the phytoene synthase gene. Under the control of proper transcription and translation regulatory sequences, these genes produce active enzymes. In this method the genes for GGPP synthase and phytoene synthase need to be identified, engineered to place the transcription and translation regulatory sequences adjacent to the genes, and then introduced into a plasmid sequence.

In the second approach, phytoene is produced in cells transformed with the pARC376 plasmid if the gene for phytoene dehydrogenase is mutated, deleted, or in any other way made non-functional. This requires an altered pARC376 plasmid that accumulates phytoene.

Example 1. Confirmation of the Presence of the Carotenoid Biosynthesis Pathway Genes in *Erwinia herbicola* Plasmid pARC376 a. *E. coli*

*E. coli* cells, which by themselves are not capable of pigment formation, become intensely yellow in color when transformed with plasmid pARC376 (FIG. 5). The pigments responsible for the observed yellow color were extracted from the cells and shown to be zeaxanthin and zeaxanthin diglucosides from UV-VIS spectral and mass spectral data.

In the presence of diphenylamine in the growth medium, pigment formation is strongly inhibited resulting in colorless cells, which have been found to accumulate trace amounts of phytoene. Diphenylamine is known to inhibit the phytoene dehydrogenase-4H reaction. This was the first indication that the carotenoid pathway is functional in these transformed cells. Harvesting mid-log phase cells and extracting carotenoids from those cells indicated the presence of phytoene, phytofluene, and zeta-carotene, further confirming the presence of functional carotenoid pathway syntheses in the cells.

b. *A. tumefaciens*

Carotenoid production in *A. tumefaciens* containing the *Erwinia herbicola* carotenoid DNA was investigated. Three plasmids containing various portions of plasmid pARC376 were transformed into *A. tumefaciens* strain LBA4404. Four different carotenoids were produced, i.e., phytoene, lycopene, beta-carotene, and zeaxanthin.

The three plasmids used in this study were:

1. Plasmid pARC803 (about 17 kb), which contained the R1162 ori, the kanamycin resistance gene (NPTII) and the *Erwinia herbicola* DNA of plasmid pARC376-Ava 103 fragment (derived by deleting 2 Ava I restriction fragments, at about 8231-8842-10453, and cloning the Hind III (about 13463) to Eco RI (about 3370 FIG. 5) fragment into plasmid pSOC925 (FIG. 12);

2. Plasmid pARC274 (about 17 kb), which contained the R1162 ori, the kanamycin resistance gene, and the *Erwinia herbicola* DNA of plasmid pARC376-Bam 100 fragment (derived by deleting 2 Bam HI restriction fragments, at about 3442-4487-5302 and cloning the Hind III (about 13463) to Eco RI (about 3370, FIG. 5) fragment into plasmid pSOC925;

3. Plasmid pARC288 (about 18 kb) which contained the R1162 ori, the kanamycin resistance gene, the *Erwinia herbicola* DNA of plasmid pARC376-Sal 8 (Example 2a) and the GGPP synthase gene fragment from Hind III (about 13463) to Eco RV (about 11196, FIG. 5).

These plasmids were transformed into competent cells of Agrobacterium according to the protocol below.

1. An Agrobacterium colony was grown overnight (about 15 hours) in 2 to 3 ml YP medium (10 g/l Bactopeptone, 10 g/l yeast extracts, and 5 g/l NaCl, pH 7).

2. The overnight culture was transferred into 50 ml fresh YP medium in 250 ml flask at 250 rpm and 28° C., and grown until the culture reached 0.5 to 1.0 OD ($A_{600}$).

3. The culture was chilled on ice for 5 minutes, then the cells were harvested by centrifugation.

4. The cells were resuspended in 1 ml of 20 mM calcium chloride.

5. About 1 µg of plasmid DNA was added into 0.1 ml of the cell suspension and mixture was incubated on ice for 30 minutes.

6. The reaction mixture was frozen in liquid nitrogen for 1 to 2 minutes and then incubated at 37° C. for 5 minutes.

7. One ml of YP medium was added and the mixture was incubated at 28° C. for 2 to 4 hours.

8. The cells were plated in LB medium (5 g/l yeast extracts, 10 g/l tryptone, 5 g/l NaCl, and 2 g/l glucose, pH 7) containing 50 µg/ml kanamycin.

The transformed cells were selected on LB plates containing 50 µg/ml of kanamycin at 28° C. (LB plates= 10 g/l tryptone, 5 g/l yeast extracts, 5 g/l NaCl, 2 g/l glucose, and 15 g/l Bactoagar). The transformed cells were cultivated on the same rich medium for two days, harvested and dried for carotenoid extraction. For carotenoid extraction, 0.5 ml of water, 2.5 ml of acetone, and 2.5 ml of methanol were added to the dried cells. After 1 hour incubation with mixing at room temperature, the solvent containing carotenoids was filtered, and carotenoids isolated were analyzed by HPLC.

The carotenoids produced by both E. coli and Agrobacterium are listed in Table 1. The amounts of carotenoids produced by Agrobacterium were about 5 to 10 times lower than by E. coli cells carrying the same plasmids (by gross estimation).

TABLE 1

Carotenoids Produced by A. tumefaciens LBA4404

| Plasmids | E. coli | Major Carotenoids Agrobacterium |
|---|---|---|
| pARC803 | Lycopene | Lycopene, Phytoene |
| pARC274 | β-Carotene | β-Carotene, (Phytoene)* |
| pARC288 | Zeaxanthin | Zeaxanthin |

*Minor component.

The origin of replication from plasmid R1162, described by Meyer, R. et al., *J. Bacteriol*, 152:140 (1982), was introduced into plasmid pARC376, to construct a broad host-range plasmid capable of replication in other bacteria. The resulting plasmid was used to introduce *Erwinia herbicola* carotenoid DNA into *Rhodobacter sphaeroides* and its carotenoid mutants. The results demonstrated that the *Erwinia herbicola* carotenoid DNA was not expressed in Rhodobacter cells, presumably because there was no complementation of the Rhodobacter phytoene synthase, phytoene dehydrogenase-4H and neurosporene dehydrogenase mutants. A further study, described hereinafter, indicated that phytoene dehydrogenase-4H could be expressed in Rhodobacter cells as hosts.

Example 2. GGPP Synthase Gent

The GGPP synthase gene was obtained from the pARC376 plasmid utilizing the following methods.

a. Digestion of Plasmid pARC376 with Sal I

The plasmid pARC376-Sal 8 is a derivative of plasmid pARC376 from which two Sal I fragments were removed. One of those fragments is the approximately 1092 bp fragment bounded by the Sal I restriction sites at about 9340 and about 10432 shown in FIG. 5, whereas the other is the 3831 bp (approximate size) fragment bounded by the Sal I restriction sites at about 10432 and about 14263 also in FIG. 5. This was accomplished as follows.

Plasmid pARC376 DNA was prepared using the alkaline lysis method. 5 Micrograms of plasmid DNA were digested with Sal I (BRL) in a high salt buffer provided by the supplier and additionally containing 150 mM NaCl, for 1 hour at 37° C. and purified on a 0.8 percent agarose gel. The remaining plasmid, about 10.2 kilobases in length, was electroeluted from the gel, phenol extracted and ethanol precipitated. After elimination of the above Sal I fragments from about positions 9340 to 14263, the remaining DNA was religated to itself to form plasmid pARC376-Sal 8.

b. Construction of Plasmid pARC808

To determine if the gene for GGPP synthase was present on the deleted *Erwinia herbicola* DNA, plasmid pARC376-Sal 8 was cloned into plasmid pSOC925, an *E. coli* plasmid R1162 derivative, to generate plasmid pARC808. The plasmid pSOC925 contains the origin of replication from the R1162 plasmid, the NPT II gene from Tn5 that confers resistance to kanamycin, and unique Hind III and Eco RI restriction sites.

Briefly, the plasmid pSOC925 expression DNA vector was prepared for cloning by admixing 5 µg of plasmid DNA to a solution containing 5 units of each of the restriction endonucleases Hind III and Eco RI and the Medium Salt Buffer from Maniatis. This solution was maintained at 37° C. for 2 hours. The solution was heated at 65° C. to inactivate the restriction endonucleases. The DNA was purified by extracting the solution with a mixture of phenol and chloroform followed by ethanol precipitation.

Plasmid pARC376-Sal 8 was digested with Hind III and Eco RI in a similar way. The *Erwinia herbicola* DNA in plasmid pARC376-Sal 8 from the Hind III site at about position 348 to the Eco RI site at about position 3370 (FIG. 5) was then ligated into the plasmid vector pSOC925 that had already been digested with Hind III and Eco RI.

The ligation reaction contained about 0.1 µg of the plasmid pSOC925 and about 0.2 µg of the *Erwinia herbicola* Hind III to Eco RI fragment from plasmid pARC376-Sal 8 in a volume of 18 µl. Two µl of 10 X ligation buffer (IBI, Corp.) and 2 units of T4 ligase were added. The ligation reaction was incubated at 4° C. overnight (about 15 hours). The ligated DNA was transformed into *E. coli* HB 101 according to standard procedures (Maniatis). This generated the plasmid pARC808, which also codes for kanamycin resistance. The excised DNA fragment from plasmid pARC376-Sal 8 contains an endogenous promoter sequence upstream from the GGPP synthase gene.

Positive clones with inserts were identified by growing prospective positive clones, isolating plasmid DNA by the alkali lysis method (Maniatis), and performing restriction enzyme analysis on the isolated plasmid DNA's. *E. coli* cells transformed with this plasmid DNA did not produce colored carotenoids, as determined by visual inspection and HPLC and TLC analysis. Other studies discussed hereinafter demonstrated that plasmid pARC808 expresses *Erwinia herbicola* enzymes that can convert phytoene into colored carotenoid pigments.

c. Construction of Plasmid pARC282

A second plasmid was constructed by inserting a restriction fragment containing the approximately 1153 bp Bgl II (about position 12349, FIG. 5) to Eco RV (about position 11196, FIG. 5) fragment from plasmid pARC376 into the Bam HI and Hind III sites of plasmid pBR322 to produce plasmid pARC282. Briefly, the plasmid pARC273 contains the *Erwinia herbicola* DNA from the Bgl II site (at about position 12349) to the Eco RV site (at about position 11196).

About 100 non-coding bp downstream from the Eco RV site in plasmid pARC273 is a Hind III restriction site, which is a part of the plasmid pARC273 vector. Here, about 5 µg of the plasmid pARC273 were incubated with 5 units of each of the restriction enzymes Bgl II and Hind III in the Medium Salt Buffer (Maniatis) for 2 hours at 37° C. Five µg of the vector pBR322 were incubated with 5 units of each of the restriction enzymes Bam HI and Hind III in the Medium Salt Buffer (Maniatis) for 2 hours at 37° C.

The *Erwinia herbicola* Bgl II to Hind III DNA fragment (about 0.2 mg) from plasmid pARC273 was admixed with the Bam HI and Hind III digested plasmid pBR322 vector (about 0.1 µg) in 18 µl total volume. Two µl of 10 X Ligation Buffer (IBI, Corp.) and 2 units of $T_4$ Ligase were added, the reaction was incubated overnight (about 15 hours) at 4° C., and the ligated DNA was transformed into competent *E. coli* HB101 cells according to procedures in Maniatis. Positive clones were identified by growing the prospective transformants, isolating plasmid DNA by the alkali lysis method (Maniatis), and performing restriction enzyme analysis on the plasmid DNA.

This plasmid, pARC282, encodes ampicillin resistance in *E. coli* and includes a native *Erwinia herbicola* promoter between the Bgl II site and the initial Met codon of the GGPP synthase gene, but does not cause any carotenoids to be produced. However, when this plasmid was transferred into *E. coli* cells containing the plasmid pARC808, and the *E. coli* cells were grown in the presence of both kanamycin and ampicillin, carotenoids were synthesized as evidenced by production of the yellow pigment zeaxanthin. Thus, plasmid pARC282 contained the essential gene that was deleted from the pARC376-Sal 8 plasmid, and the presence of this gene in combination with other *Erwinia herbicola* carotenoid genes could restore carotenoid production in *E. coli*.

d. Other Plasmid Constructs

Enzyme assays were performed on similar plasmid constructs, including plasmid pARC491 which was constructed by cloning the approximately 1068 bp fragment from Hpa I (at about position 12264 of plasmid pARC376 or about position 84 of FIG. 2) to Eco RV (at about position 11196, FIG. 5) into a plasmid denominated pARC306A. Plasmid pARC306A, whose restriction map is illustrated in FIG. 6 contains approximately 2519 base pairs. This plasmid contains the polylinker region from pUC18, a unique Nco I site, the ampicillin selectable marker, the pMB1 origin of replication and the Rec 7 promoter. Cells containing this plasmid construct had a level of 7.91 nmol/min/mg protein activity of GGPP synthase.

e. DNA sequencing

The accuracy of some of the cloning steps was confirmed by sequencing the insert using the dideoxy method described by Sanger et al., *Proc. Natl. Acad. Sci.* USA, 74:5463–5467, (1977) and following the manufacturer's instructions included in a sequencing kit from BRL.

The DNA sequence was determined for the approximately 1153 base pair restriction fragment from the region between the Bgl II site at about 12349 of FIG. 5 and the Eco RV site at about 11196 of FIG. 5. The obtained DNA sequence and deduced partial amino acid residue sequences are shown in FIG. 2. The direction of transcription of the gene for GGPP synthase in pARC376 (FIG. 5) is counterclockwise and proceeds in the direction from the Bgl II site toward the Eco RV site.

f. In Vitro mutagenesis

The initiation codon for GGPP synthase begins at about nucleotide position 12226 of plasmid pARC376 with the ATG codon for methionine (about position 124 of FIG. 2). A Nco I restriction site was introduced at this position of the GGPP synthase gene using in vitro mutagenesis following the techniques described in *Current Protocols In Molecular Biology*, Ausabel et al. eds., John Wiley & Sons, New York, (1987) p. 8.1.1–8.1.6, with the exception that *E. coli* CJ 236 was grown (in step 3 at page 8.1.1) in further presence of 20 µg/µl chloramphenicol. The primer used was:

5'              3'
TCA GCG GGT AAC CTT GCC ATG GGG AGT GGC AGT AAA GCG
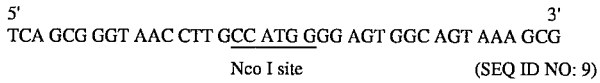

The mutations were confirmed either by DNA sequencing or by the presence of the newly introduced Nco I site. This manipulation changed the natural sequence TTG CAATGG TGA (SEQ ID NO:10) to

TTG CCATGG GGA (SEQ ID NO:11), wherein a bold-faced letter above and in the following examples indicates an altered base.

This modified version of the GGPP synthase gene from the newly introduced Nco I site to the Eco RV site (about 1029 bp) was then inserted into the plasmid pARC306A to generate plasmid pARC417BH. This plasmid, pARC417BH, contains the *E. coli* promoter Rec 7 adjacent to a multiple cloning site. Structural genes lacking a promoter region, when introduced adjacent to the Rec 7 promoter, are expressed in *E. coli*.

When plasmid pARC417BH was introduced into *E. coli* cells, GGPP synthase enzyme activity (measured as GGOH) was found at the level of 6.35 nmol/min/mg protein. In addition, when plasmid pARC417BH was introduced into *E. coli* cells containing plasmid pARC808, carotenoids were produced. This demonstrated that the gene for GGPP synthase had been identified and genetically engineered.

g. Fine tuning the GGPP synthase gene

Several constructs designed to express the GGPP synthase gene were made to optimize the expression of an active GGPP synthase enzyme. Again using in vitro mutagenesis according to methods previously cited, a Nco I site was introduced at about position 12264 of plasmid pARC376, using the primer, 5'              3'
CAT GGC GAA ATA GAA GCC ATG GGA CAA TCC ATT GAC GAT
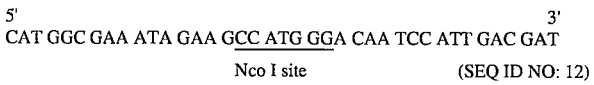

17 amino acids downstream from the initiation codon for the GGPP synthase gene that is located at about position 124 in FIG. 2. That site was thus placed at the upstream side of the Met whose ATG codon begins at about position 175 of the sequence of FIG. 2. The natural DNA sequence AAG TAATGA GAC (SEQ ID NO:13) was changed to

AAG CCATGG GAC (SEQ ID NO:14).

This modified GGPP synthase gene coding for seventeen fewer amino-terminal amino acid residues was inserted into plasmid pARC306A at the Nco I site of that plasmid to generate plasmid pARC418BH.

When GGPP synthase assays were performed on cells transformed with plasmid pARC418BH, no enzyme activity was detected. In addition, when this modified GGPP synthase was added to *E. coli* cells containing the plasmid having the rest of the genes for the enzymes required for carotenoid synthesis, plasmid pARC808 described above, no carotenoids were synthesized. This demonstrated that deletion of the 17 N-terminal amino acids of the GGPP synthase resulted in a non-functional enzyme.

Plasmid pARC306A was digested with Eco RI. The Eco RI ends were converted to blunt ends using the Klenow fragment of DNA Pol I according to the usual techniques described by Maniatis. The GGPP synthase gene was cleaved with Nru I and Sac I to provide a Nru I-Sac I restriction fragment that extended from about position 12187 to about position 11776 of FIG. 5. After further digestion of the cleaved, blunt-ended plasmid pARC306A with Sac I, the Nru I-Sac I fragment was ligated therein to form plasmid pARC488A.

Plasmid pARC282 was digested with Sac I and Hind III, and the Sac I-Hind III fragment was isolated. Plasmid pARC488A was digested with Sac I and Hind III, and the Sac I-Hind III fragment from pARC282 was ligated therein to form plasmid pARC489B. The above digestions and blunt end formation removed the polylinker region shown in FIG. 6 from the Eco RI site to the Hind III site.

Positive clones were identified by plasmid DNA isolation (Maniatis), and by restriction enzyme analysis on the plasmid DNA.

In plasmid pARC489B, DNA coding for the first 13 amino acid residues of the GGPP gene was deleted. The first four amino acid residues encoded downstream from the Rec 7 promoter in plasmid pARC306A and the newly generated Eco RI blunt end were placed upstream from the former Nru I site of GGPP synthase. This altered the N-terminal amino acid sequence of GGPP synthase in the following manner. The difference in amino acid sequence became:

Original Amino Acid Sequence of Native Erwinia Herbicola GGPP Synthase.
MET VAL SER GLY SER LYS ALA GLY VAL SER PRO HIS ARG GLU ILE...
(SEQ ID NO: 15)

Amino Acid Sequence of modified GGPP Synthase Gene in Plasmid pARC489B
MET ALA GLU PHE GLU ILE... (SEQ ID NO: 16)

in which altered bases are shown in bold face. The DNA sequence for this heterologous gene is illustrated in FIG. 3, with the coding region beginning at about position 150 and extending through to about position 1153.

*E. coli* cells transformed with the plasmid pARC489B were assayed for GGPP synthase activity. The level of activity was found to be 12.15 nmol/min/mg protein.

When the plasmid pARC489B was transferred to *E. coli* cells that contained a plasmid containing the rest of the genes coding for enzymes required for carotenoid production, plasmid pARC808, the cells produced carotenoids. Therefore, this construction coded for an active enzyme even though the heterologous gene portion from plasmid pARC306A encoded the first four amino acid residues, and the first 13 amino acid residues encoded by the gene for GGPP synthase were deleted.

The above described DNA segment of plasmid pARC489B overlaps bases encoding four amino acids adjacent to the Rec 7 promoter at its 5' end and extends to the blunted, former Eco RI site in the polylinker region of the plasmid. This DNA segment can be excised by reaction with Nco I at its 5' end and the Hind III or Pvu II sites as are illustrated for plasmid pARC306A in FIG. 6.

The desired GGPP synthase gene does not contain a Pvu II or a Hind III restriction site. The region between the Hind III and Pvu II sites of plasmid pARC489B contains stop codons in all three reading frames. It is preferred to utilize the Pvu II site for cleavage of the 3' end of the DNA. Thus, the desired GGPP synthase DNA segment can be referred to as lying within the approximately 1150 bp sequence between the Nco I and Pvu II restriction sites of plasmid pARC489B.

Next, the 3' end of the gene for GGPP synthase was modified. This construction was made in the following manner.

Plasmid pARC489B was digested with Bal I and Hind III. (This Bal I site is at about position 11347 of FIG. 5.) The Hind III site of the resulting large restriction fragment was filled in using the Klenow fragment of DNA polymerase 1. The resulting double blunt ended fragment was religated together to form plasmid pARC489D.

The GGPP synthase gene-containing portion of the resulting plasmid pARC489D has the same 5' end as does plasmid pARC489B, but the 3' end is about 151 bp shorter than the GGPP synthase gene in plasmid pARC489B. The sequence of the heterologous GGPP synthase structural gene of plasmid pARC489D is illustrated in FIG. 3 from about position 150 to about position 1002, with the 5' end of this DNA being the same as that of the GGPP synthase gene present in plasmid pARC489B.

Downstream about 70 bp from the Hind III site of the multiple cloning region in plasmid pARC306A is a Pvu II site. There are no Pvu II sites in the GGPP synthase gene. Therefore, the GGPP synthase structural gene can be transferred from a pARC306A-derived plasmid such as plasmid pARC489D to other plasmids as an approximately 1000 bp Nco I-Pvu II fragment.

Plasmid pARC489D was transformed into *E. coli*. Very surprisingly, this construction gave the highest enzyme activity of all the different versions of the GGPP synthase gene. This activity was an unexpectedly high 23.28 nmol/min/mg protein.

When the plasmid pARC489D was introduced into *E. coli* cells containing the plasmid pARC808, carotenoids were synthesized.

A comparison of the activities of several of the previously described GGPP synthase gene constructs is shown in Table 2 below, including the activity of a related gene present inherently in *R. sphaeroides* 2.4.1. Those results indicate an enhancement of about 35 to about 130 times the activity of the original plasmid pARC376.

TABLE 2

GGPP Synthase Activity of Various Gene Constructs As Compared to *R. sphaeroides*

| Constructs | Activity (nmol/min/mg protein) |
| --- | --- |
| *R. sphaeroides* 2.4.1 | 0.20 |
| pARC376 | 0.18 |
| pARC491 | 7.91 |
| pARC417BH | 6.35 |
| pARC418BH | 0 |
| pARC489B | 12.15 |
| pARC489D | 23.28 | h. GGPP synthase characterization

The plasmids pARC489B and pARC489D were introduced into the *E. coli* Strain JM101 (BRL). These cells were treated with nalidixic acid to induce the Rec 7 promoter, which caused production of large amounts of the GGPP synthase enzyme. The protein extract from these cells was separated on SDS-polyacrylamide gel electrophoresis (PAGE). Because of the very large amount of GGPP synthase produced under these conditions, it is readily identifiable by staining with Coomassie Brilliant Blue on the SDS-PAGE system. The isolated and substantially purified GGPP synthase can then be recovered from the gels by standard procedures.

The *Erwinia herbicola* GGPP synthase that was produced in cells containing plasmid pARC489B was a protein of the size of about 35 kilodaltons, and is thought to be the complete, native molecule, whereas the GGPP synthase that was produced in cells with plasmid pARC489D was about 33 kilodaltons. Thus, the 5' deletion of thirteen amino acid residues and then replacement with non-*Erwinia herbicola* sequence of four residues, coupled with the 3' deletion of the approximately 151 bp between the Bal I site and the Eco RV site produced a protein that was about 2 kilodaltons smaller, but far more active than the native molecule. The GGPP synthase structural gene present in plasmid pARC489D is the gene most preferably used for GGPP synthase in *E. coli*, *S. cerevisiae*, and higher plants.

i. Induction of Rec 7 driven protein production

The previously discussed production of GGPP synthase in *E. coli* using plasmids pARC417BH, pARC489B and pARC489D was carried out using the Rec 7 promoter. Phytoene synthase production in *E. coli* using the plasmid pARC140N discussed below was also carried out using the Rec 7 promoter. Culture conditions for growth of the transformed *E. coli* cells are as follows.

A single colony from a plate containing freshly (<2 days old) transformed cells was picked, grown overnight (e.g. about 15–18 hours) in M9+CAGM medium (see Table 3B hereinafter for media formulations)+ 50 µg/ml ampicillin at 30° C. Cultures of cells were grown at various temperatures from 27°–37° C. by diluting the cells 1:100 into fresh M9+CAGM medium and maintaining the culture at the desired temperature. Each culture was grown until it was roughly one-half of the final desired density (150–180 Klett units in a shaken culture). The culture was then induced by addition of nalidixic acid to a final concentration of 50 µg/ml. Five µl of a stock solution of freshly prepared 10 mg/ml nalidixic acid in 0.1N NaOH per ml of culture to be induced was used. Induction was permitted to proceed for 2–4 hours after addition of nalidixic acid.

TABLE 3

A. M9 + CAGM MEDIUM COMPOSITION

| Component | grams/liter |
| --- | --- |
| $Na_2HPO_4 \cdot 7H_2O$ | 13.2 |
| $KH_2PO_4$ | 3.0 |
| NaCl | 0.5 |
| $NH_4Cl$ | 1.0 |
| Casamino Acids (Difco) | 10.0 |
| $MgSO_4$ | 0.3 |
| $CaCl_2 \cdot 2H_2O$ | 0.004 |
| Glucose (Shake Flask) | 3.0 |
| Thiamine-HCl | 0.025 |
| $FeCl_3$ | 0.0054 |
| $ZnSO_4$ | 0.0004 |
| $COCl_2$ | 0.0007 |
| $Na_2MoO_4$ | 0.0007 |
| $CuSO_4$ | 0.0008 |

TABLE 3-continued

| $H_2BO_3$ | 0.0002 |
| --- | --- |
| $MnSO_4$ | 0.0005 |

B. MEDIUM FORMULATIONS
M9 + CAGM Medium for Shake Flasks (1 Liter)

| 900 ml | distilled $H_2$ | Autoclaved |
| --- | --- | --- |
| 40 ml | 25X M9 Salts | Autoclaved |
| 50 ml | 20% (w/v) Casamino Acids | Filtered |
| 6.4 ml | 40% (w/v) Glucose | Autoclaved |
| 1.2 ml | 1M $MgSO_4$ | Autoclaved |
| 0.25 ml | 0.1M $CaCl_2$ | Autoclaved |
| 0.25 ml | 0.1% (w/v) Thiamine-HCl | Filtered |
| 0.1 ml | 10,000X Trace Minerals | Filtered |
| 0.1 ml | 10,000X Iron Supplement | Filtered |

All components should be sterilized separately, cooled to room temperature and then combined.

| Component | grams |
| --- | --- |
| C. 25X M9 Salts (1 liter) | |
| $Na_2HPO_4 \cdot 7H_2O$ | 330 |
| $KH_2PO_4$ | 75 |
| $NH_4Cl$ | 25 | distilled $H_2O$ to 1 Liter

| D. 10,000X Trace Minerals (200 ml) | |
| --- | --- |
| $ZnSO_4$ | 0.8 |
| $COCl_2$ | 1.4 |
| $Na_2MoO_4$ | 1.4 |
| $CuSO_4$ | 1.6 |
| $H_2BO_3$ | 0.4 |
| $MnSO_4$ | 1.0 |

Dissolve in 200 ml of $H_2O$, add 1 drop HCl (fuming), filter sterilize.

| E. 10,000X Iron Supplement (200 ml) | |
| --- | --- |
| $FeCl_3$ | 10.8 |

Dissolve in 200 ml of $H_2O$, add 1 drop HCl (fuming), filter sterilize.

Each culture was highly aerated at all times. Fifteen ml in a 250 ml sidearm flask for analytical runs were routinely used, and 330 ml in a Fernbach (2.8 l) flask for semi-preparative runs were routinely used.

Production of all proteins examined so far has been quite dependent on strong aeration during the induction period.

j. Enzyme assay

GGPP synthase was prepared in the cell cytosol as described below.

(1) Cytosol preparation

The growing cells were centrifuged to form a cell pellet. The cell pellet was resuspended in 50 mM potassium phosphate buffer, pH 7.0, containing 10 percent glycerol, 0.1 mM EDTA in a 15 ml plastic conical tube and vortexed with acid washed glass beads (425–600 micron for yeast cells and 75–150 micron for bacteria are typically used) for 1 minute and allowed to cool in ice for 1 minute. This was repeated three times after which the homogenate was transferred to another tube and centrifuged at 17,000× g for 60 minutes at 4° C. The supernatant was next centrifuged at 150,000× g for 60 minutes at 4° C. The supernatant thus obtained was the cell cytosol.

(2) Assay for GGPP synthase

Cell cytosol was preincubated for 20 minutes at 4° C. with 10 µM epoxy-isopentenyl pyrophosphate (IPP) in order to inhibit IPP-isomerase activity. The assay mixture, containing 40 µM farnesyl pyrophosphate (FPP) and 40 µM 14C-IPP (250,000 dpm) in 10 mM Hepes buffer (pH 7.0, 1 mM MgCl$_2$, 1 mM DTT) in a 1 ml total volume of preincubated cytosol, was incubated at 37° C. for 30 minutes.

The reaction was terminated by transferring the assay mixture to a pre-cooled (in dry ice) tube and lyophilizing for 8 hours. The dry residue was resuspended in 0.5 ml of 0.1M glycine buffer (pH 10.4, 1 mM MgCl$_2$, 1 mM ZnCl$_2$) and treated with 25 units of alkaline phosphatase for 3 hours at 37° C. The alkaline phosphatase reaction converted the pyrophosphates to their corresponding alcohols, which were extracted with hexane, evaporated to dryness under a stream of nitrogen and redissolved in 150 μl of methanol.

Seventy-five μl of this methanol solution were injected into an HPLC connected with a C-18 econosphere Altech analytical column (4.6×250 nm, 5 micron particle size) equilibrated with 85 percent methanol:water (4:1) and 15 percent THF:CH$_3$CN (1:1). A linear gradient to 80 percent methanol:water (4:1) and 20 percent THF:CH$_3$CN (1:1) in 20 minutes at 1.5 ml/min resolved the alcohols. The HPLC was connected in series with a Radiomatic flow detector, which integrated the radioactive peaks, e.g. geranylgeraniol (GGOH) peak. Specific activity was expressed in nmol GGOH formed/min/mg of protein under the given assay conditions. Protein was determined by the Bradford method using BSA as the standard.

Example 3. GGPP Synthase Production in Higher Plants a. Construction of the plasmid pARC498

The most active form of the GGPP synthase gene is found on plasmid pARC489D, described above. The GGPP synthase structural gene of this plasmid was modified to introduce the restriction site Sph I at the initiation methionine codon and another Sph I site at the 3' end of the gene following the stop codons present in plasmid pARC489D.

To accomplish these modifications, an about 1,100 bp Hpa I to Pvu II (present in the vector) fragment was excised from plasmid pARC489D. This fragment was isolated on agarose gel electrophoresis and used as the template for polymerase chain reaction (PCR). The following oligonucleotide probe was used to create the Sph I site at the ATG start codon of the GGPP synthase gene:

5' TAA GCA TGC TCG AAT TCG AAA TAG AAG TAA TG 3'    (SEQ ID NO: 17),
      Sph I (SEQ ID NO:17), in which bold-faced letters indicate altered bases.

This PCR technique changed the second residue of GGPP synthase from an alanine to a leucine.

The following oligonucleotide probe was used to create the Sph I site after the stop codon in the plasmid pARC489D following the GGPP synthase gene:

5' CCG CGC ATG CGA CCC TTG TGT ATC AAA CAA G 3'
      Sph I                             (SEQ ID NO: 18)

The probes were resuspended in a volume of sterile water such that final concentration of each probe was 10 pmoles/μl.

The introduction of an Sph I site at the 3' end of the GGPP synthase gene changed the DNA sequence as indicated below:

Original Sequence:
5' CTT GTT TGA TAC ACA AGG GTC GCA TCT CGC G 3'
                                                  (SEQ ID NO: 19)

New Sequence:
5' CTT GTT TGA TAC ACA AGG GTC GCA TGC GCG G 3',
                                                  (SEQ ID NO: 20)

in which a bold-faced letter in the new sequence indicates an altered base.

b. PCR Reaction

The GeneAmp DNA Amplification Reagent Kit (Perkin Elmer Cetus) was used to perform the reaction. The following components were mixed in the quantity and order specified according to the manufacturers instructions.

| Component | Order of Addition | Volume | Final Concentration |
|---|---|---|---|
| Sterile Water | 1 | 43.5 μl | |
| 10 X Rxn. Buffer | 2 | 10 μl | 1 X |
| 1.25 mM dNTP Mix | 3 | 16 μl | 200 μM each |
| Primer 1 (10 pMole/μl) | 4 | 10 μl | 1 μM |
| Primer 2 (10 pMole/μl) | 5 | 10 μl | 1 μM |
| Template DNA | 6 | 10 μl | 100 ng |
| Taq Polymerase | 7 | 0.5 μl | 2.5 Units |

Mineral oil (100 μl) was layered on top of the reaction mixture, and the reaction was performed using the Perkin Elmer Cetus DNA Thermal Cycler (Perkin Elmer, Prairie Cloud, Minn.). The method consisted of 25 cycles of amplification. One cycle included the following:

1) 1 minute denaturation at 92° C.;
2) 2 minute template priming at 37° C.;
3) 3 minute polymerization at 72° C.;

At the end of 25 cycles, one final 7 minute polymerization at 72° C. was carried out.

After the reaction was completed the mineral oil was removed, the reaction mixture was extracted twice with ether, and the DNA was precipitated with ethanol.

c. Cloning of the PCR produced DNA fragment

The DNA produced by the PCR reaction was digested with Sph I. This about 936 bp Sph I PCR-generated fragment was isolated and recovered from an agarose gel, and cloned into the unique Sph I site of plasmid pUC18 (Pharmacia Piscataway, N.J.). This resulting plasmid was named pARC498.

d. Proof of Functional Genetically Engineered GGPP Synthase Gene

The proper functioning of the GGPP synthase gene of plasmid pARC498 was tested by cloning the PCR modified gene into an *E. coli* expression vector. This was done by first digesting plasmid pARC498 with Hind III and Sma I, these sites being on either side of the Sph I site. The resulting Hind III-Sma I fragment was isolated and recovered from an agarose gel, and treated with the Klenow fragment of DNA Polymerase I to create blunt ends. This blunt ended fragment was then cloned into plasmid pKK223-3 (Pharmacia, Piscataway, N.J.), as follows.

Plasmid pKK223-3 contains the TAC promoter active in *E. coli*. Plasmid pKK223-3 was digested with Hind III and similarly treated with the Klenow fragment to form blunt ends. The Hind III-Sma I blunt ended fragment, excised from plasmid pARC498, was ligated to the blunt ended plasmid pKK223-3. The resulting plasmid was named pARC1504.

When plasmid pARC1504 was introduced into *E. coli* cells containing plasmid pARC808, carotenoids were produced. This demonstrated that the modified GGPP synthase gene encoded a functional GGPP synthase enzyme.

e. Construction of plasmid pATC225

The PCR modified GGPP synthase structural gene was removed as an Sph I fragment from plasmid pARC498. This Sph I fragment was cloned into the Sph I site of plasmid pATC212, which construction is discussed below. The resulting plasmid was named pATC216. This plasmid contains a GGPP synthase gene construct with a CaMV 35S plant promoter and transit peptide sequence at the 5' end of the gene, and a NOS polyadenylatien sequence at the 3' end.

This GGPP synthase gene construct was inserted into the plasmid pGA482 (Pharmacia) in convenient restriction sites within the multiple cloning linker region to form plasmid pATC225. The relevant features of plasmid pGA482 include (i) an origin of replication that permits maintenance of the plasmid in *Agrobacterium tumefaciens*, (ii) the left and right border sequences from the T-DNA region that direct the integration of the DNA segment between the borders into the plant genome, and (iii) the NOS promoter adjacent to the kanamycin resistance gene that permits plant cells to survive in the presence of kanamycin.

This GGPP synthase gene construct was transformed into *Agrobacterium tumefaciens* LBA4404 (Clontech, Inc.) according to standard protocols. Agrobacterium cells containing the plasmid with the GGPP synthase gene construct were transferred by infection of tobacco leaf discs using the method of Horsch et al., *Science*, 227:1229–1231 (1985). During the infection process, the entire DNA segment between the left and right borders of the pGA482 plasmid is transfected into the plant cells. Transfected plant cells are selected for kanamycin resistance.

Western blots of extracts from transfected plant chloroplasts showed the presence of GGPP synthase. No enhancement of carotenoid production was observed.

The specific DNA segments, recombinant molecules and techniques utilized in the preparation of the above tobacco plants are discussed below.

i. Transit Peptide

The sequence of the transit peptide DNA is basically that of Mazur et al., *Nucl. Acids Res.*, 13:2343–2386 (1985) for the ribulose bis-phosphate carboxylase-oxygenase signal peptide of *Nicotiana tabacum*. Two changes were made to the disclosed 177 bp sequence.

In the first change, two cytidine residues were added at the 5' end to create a Nco I restriction site. The second change introduced an Nat I site that cleaves between bases at positive 73 and 74. This change was a G for T replacement at position 69 and a G for A replacement at position 72, both of which changes left the encoded amino acid residue sequence unchanged. The final two residues at the 3' end were deleted to provide the natural Sph I restriction site sticky end.

The synthetic transit peptide-encoding DNA also therefore contained 177 bp. The complete double stranded sequence, showing the 5' Nco I and 3' Sph I sticky ends, is illustrated in FIG. 11.

The DNA encoding the transit peptide was synthesized synthetically from eight fragments that were annealed together in pairs by heating at 90 degrees C. for five minutes and then slowly cooling to room temperature. Fifty picomoles of each fragment were utilized.

Those eight fragments were:

1. 5' CAT GGC TTC CTC AGT TCT TTC CTC TGC AGC
   AGT TGC C 3'   (SEQ ID NO: 21)

2. 5' GGG TGG CAA CTG CTG CAG AGG AAA GAA CTG
   AGG AGG C 3'   (SEQ ID NO: 22)

3. 5' ACC CGC AGC AAT GTT GCT CAA GCT AAC ATG
   GTG G 3'   (SEQ ID NO: 23)

4. 5' CGC CAC CAT GTT AGC TTG AGC AAC ATT GCT
   GC 3'   (SEQ ID NO: 24)

5. 5' CGC CTT TCA CTG GCC TTA AGT GAG CTG CCT
   CAT TCC CTG TTT CAA GGA AG 3'
   (SEQ ID NO: 25)

6. 5' TTT GCT TCC TTG AAA CAG GGA ATG AGG CAG
   CGA ATG AGG CAG CGA ATG AGG CAG CTG
   ACT TAA GGC CAG TCA AAG G 3'
   (SEQ ID NO: 26)

7. 5' CAA AAC CTT CAG ATC ACT TCC ATT GCC AGC
   AAC GGC GGA AGA GTG CAA TGC ATG 3'
   (SEQ ID NO: 27)

8. 5' CAT TGC ACT CTT CCG CCG TTG CTG GCA ATG
   GAA GTG ATG TCA AGG T 3'   (SEQ ID NO: 28)

The pairs utilized for annealing were 1 and 2, 3 and 4, 5 and 6, and 7 and 8 to form sticky ended annealed pairs 1–2, 3–4, 5–6 and 7–8 that are shown below.

1-2   (SEQ ID NO:21)

5' CATGGCTTCCTCAGTTCTTTCCTCTGCAGCAGCAGTTGCC 3'
3' CGAAGGAGTCAAGAAAGGAGACGTCGTCGTCAACGGTGGG 5'
(SEQ ID NO:22)

3-4   (SEQ ID NO:23)

5' ACCCGCAGCAATGTTGCTCAAGCTAACATGGTGG 3'
3' CGTCGTTACAACGAGTTCGATTGTACCACCGA 5'
(SEQ ID NO:24)

5-6

5' CGCCTTTCACTGGCCTTAAGTCAGCTGCCTCATTCCCTGTTTCA
3' GGAAAGTGACCGGAATTCAGTCGACGGAGTAAGGGACAAAGT

AGGAAG 3'   (SEQ ID NO:25)
TCCTTCGTTT 5'   (SEQ ID NO:26)

7-8
```
5' CAAAACCTTGACATCACTTCCATTGCCAGCAACGGCGGAAGAGT
3' TGGAACTGTAGTGTGAAGGTAACGGTCGTTGCCGCCTTCTCA

GCAATGCATG 3'                    (SEQ ID NO:27)
   CGTTAC 5'                        (SEQ ID NO:28)
```

Fragment 1-2 was ligated with fragment 3-4 to
form fragment 1-4 whose sequence is shown below.

```
5' CATGGCTTCCTCAGTTCTTTCCTCTGCAGCAGTTGCCACCCGCAGCAA
3' CGAAGGAGTCAAGAAAGGAGACGTCGTCAACGGTGGGCGTCGTT

TGTTGCTCAAGCTAACATGGTGG 3'       (SEQ ID NO:29)
   ACAACGAGTTCGATTGTACCACCGC 5'     (SEQ ID NO:30)
```

Fragment 5-6 was ligated with fragment 7-8 to
form fragment 5-8 whose sequence is shown below.

```
5' CGCCTTTCACTGGCCTTAAGTCAGCTGCCTCATTCCCTGTTTCAAGGA
3' GGAAAGTGACCGGAATTCAGTCGACGGAGTAAGGGACAAAGTTCCT

AGCAAAACCTTGACATCACTTCCATTGCCAGCAACGGCGGAAG
   TCGTTTTGGAACTGTAGTGAAGGTAACGGTCGTTGCCGCCTTC

AGTGCAATGCATG 3'                 (SEQ ID NO:31)
5' TCACGTTAC                        (SEQ ID NO:32)
```

The 1-2 and 3-4 pairs (fragments 1-4) were ligated together over a two hour time period, as were pairs 5-6 and 7-8 to form two double-stranded sequences. The ligation product of fragments 1-4 was digested with Nco I and Nar I, whereas the product of fragments 5-8 was digested with Nar I and Sph I. These digestions separated any concatamers formed during ligation and provided the necessary sticky ends for further ligation.

The digested mixes were run on 6 percent acrylamide gels. The bands of correct size were excised from the gels, and the DNA was eluted from the gel matrix.

The DNA fragments of (1-4) and (5-6) were ligated together to form a 177 base pair molecule. As above, the ligation was digested with restriction enzymes to create the necessary ends for subsequent cloning of the molecule. In this case, the ligation of fragments (1-4) and (5-8) was digested with Nco I and Sph I. The digested ligation product DNA segment was run on a 6 percent polyacrylamide gel. The band of 177 base pairs was excised and eluted from the gel.

The 177 base pair fragment was cloned into plasmid pARC466. Plasmid pARC466 is a plasmid identical to M13mp19 except that an Nco I site has replaced the native Hind III site. This plasmid contains a polylinker region including a Sma I site that is downstream from the Sph I site.

The Nco I site in plasmid pARC466 was created by replacing the originally present Hind III site using in vitro mutagenesis as discussed previously. The primer used was:

```
                    Nco I
5' CCT GCA GGC ATC CAA CCA TGG CGT AAT CAT GGT CAT 3'
                         (SEQ ID NO: 33)
```

Plasmid pARC466 was digested with Nco I and Sph I. The 177 bp transit peptide DNA fragment ends were designed to clone into these sites. The ligation of the 177 base pair fragment into plasmid pARC466 resulted in plasmid pARC480. Plasmid pARC480 was sequenced by M13 protocol to check the sequence of the designed peptide, which sequence was found to be correct.

ii. Plasmid pATC212

The transit peptide was moved into a plasmid that contained a plant promoter and termination sequence. pCaMVCN is a plasmid supplied by Pharmacia that contains the cauliflower mosaic virus 35S promoter and a NOS polyadenylation sequence. The transit peptide was cloned next to the 35S promoter as follows:

a) Plasmid pCaMVCN was digested with the restriction enzyme Sal I. Linker #1104 from New England Biolabs d(TCGACCCGGG) was digested with Sal I and then ligated with the digested pCaMVCN to create plasmid pATC209.

b) Plasmid pATC209 was digested with Sma I. Plasmid pARC480 was digested with Nco I and Sma I to remove the transit peptide. The Nco I site of the transit peptide DNA was treated with the Klenow fragment of E. coli DNA polymerase to create a blunt end to make that fragment compatible with the Sma I site of plasmid pATC209. The double blunt-ended fragment was cloned into the Sma I-digested plasmid pATC209 to create plasmid pATC212.

iii. Plasmid pATC255

Plasmid pATC255 is a derivative of plasmid pGA482 that contains the gene for GGPP synthase with the transit peptide sequence in frame with the coding sequence of the GGPP synthase gene. This gene construct is driven by the CaMV 35S promoter and contains the NOS polyadenylation site downstream of the structural gene. The plasmid was made in the following way.

The plasmid pARC498 contains a version of the GGPP synthase gene with a Sph I site at the initiation methionine codon and a Sph I site after the stop codon following the GGPP synthase structural gene sequence. Plasmid pARC498 was digested with Sph I.

Plasmid pATC212 was also digested with Sph I. The Sph I site is at the 3' end of the transit peptide sequence. The above Sph I GGPP synthase gene fragment was cloned into the Sph I site of the pATC212 plasmid, resulting in plasmid pATC216.

Plasmid pATC216 contains the CaMV 35S promoter, the transit peptide sequence, the GGPP synthase structural gene, and the NOS polyadenylation sequence. This whole region of plasmid pATC216 can be moved as a Hind III-Bgl II fragment, since there is a Hind III site upstream from the CaMV 35S promoter and a Bgl II site downstream from the NOS polyadenylation sequence.

Plasmid pATC216 was digested with Hind III and Bgl II and the Hind III-Bgl II fragment was cloned into the Hind III and Bgl II sites of plasmid pGA225. The resulting plasmid is pATC255.

f. Production in the Plant Cytoplasm

To prepare GGPP synthase in the cytoplasm, the carotenoid genes described before are introduced into appropriate vector(s), as also described above for chloroplasts, using identical techniques, except that the transit peptide is eliminated. Because they are not targeted to the chloroplast, the enzymes remain in the cytoplasm, and can be isolated from the cytosol.

Example 4. Phytoene Synthase Gene a. Digestion of pARC376 with Pst I

The plasmid pARC376-Pst 122 was created by deletion of an approximately 592 bp Pst I *Erwinia herbicola* DNA fragment from Pst I sites at about 5807 to about 5215 of plasmid pARC376 (FIG. 5), followed by religation of the larger of the two fragments. The Eco RI (about 3370) to Hind III (about 13463) fragment from plasmid pARC376-Pst 122, which contains the desired *Erwinia herbicola* DNA fragment, was cloned into the plasmid pARC305A, resulting in plasmid pARC139.

The plasmid pARC305A contains the polycloning linker from pUC18, the chloramphenicol acetyltransferase gene (CAT) that confers chloramphenicol resistance in *E. coli* and the pMB1 origin of replication. The plasmid pARC305A is an analogous plasmid to plasmid pUC18 except plasmid pARC305A contains the CAT selectable marker whereas pUC18 contains the ampicillin selectable marker.

When the resulting *Erwinia herbicola* DNA was inserted into the plasmid pARC305A to create the plasmid pARC139 and introduced into *E. coli* cells, no carotenoids were made, as expected.

An impairment of the gene for phytoene synthase would cause the *E. coli* cells not to produce any colored carotenoids. Therefore, the deletion of this 592 bp region could have deleted part of the gene for phytoene synthase.

b. Construction of Plasmid pARC285

The construction of plasmid pARC285 used the approximately 1112 bp Nco I to Eco RI fragment from the plasmid pARC376-Bam 100. The plasmid pARC376-Bam 100 is a derivative of the pARC376 plasmid in which the approximately 1045 bp Bam HI fragment from about position 3442 to about position 4487 (FIG. 5) and the approximately 815 bp Bam HI fragment from about position 4487 to about 5302 (FIG. 5) were deleted. A total of about 1860 nucleotides was deleted from the pARC376 plasmid. As a result of the deletions of the Bam HI fragments from plasmid pARC376, the Bam HI site at about 5302 at the 3' end was brought within about 72 nucleotides of the Eco RI site originally at about position 3370 of plasmid pARC376. The resulting restriction fragment therefore contained about 1112 bp and was bounded by Nco I and Eco RI restriction sites at its 5' and 3' ends, respectively.

The phytoene synthase gene is contained on an approximately 1040 bp Nco I to Bam HI restriction fragment (corresponding approximately to positions 6342 and 5302 of FIG. 5, respectively), but it can be cloned into other plasmids as an approximately 1112 bp Nco I to Eco RI fragment. The approximately 1112 bp Nco I to Eco RI fragment was excised from the plasmid pARC376-Bam 100 and cloned into the Nco I to Eco RI sites of plasmid pARC306A to generate plasmid pARC285. The relevant portion of the phytoene synthase gene can thus be excised from plasmid pARC285 as an approximately 1112 bp Nco I to Eco RI fragment.

c. Construction of Plasmid pARC140N

Analysis of the region surrounding the Nco I (about position 6342) site revealed that the methionine codon internal to the Nco I site was in an open reading frame that had another methionine codon 13 amino acid residues upstream. Immediately upstream from this methionine codon, was a consensus sequence for the ribosome binding site (AGGA) that is often found in procaryotic organisms upstream from the initiation codon of a gene.

To determine if the upstream methionine was in fact the initiation codon, a Bgl II site was introduced immediately upstream from the methionine codon of the Nco I site, using in vitro mutagenesis, as described before. Two complementary polynucleotide sequences were made that contained a Nco I overhang on one end and on the other end a Bgl II overhang. The sequences were as follows:

```
              Bgl II                                               Nco I
              5'                                                   3'
              GATCTAAAATGAGCCAACCGCCGCTGCTTGACCACGCCACGCAGAC
                                     (SEQ ID NO:34)

ATTTTACTCGGTTGGCGGCGACGAACTGGTGCGGTGCGTCTGGTAC
              3'                                                   5'
                                     (SEQ ID NO:35)
```

The two complementary single stranded polynucleotide sequences were hybridized together, ligated to an approximately 1112 bp Nco I-Eco RI fragment from plasmid pARC285 containing the approximately 1040 bp Nco I to Bam HI phytoene synthase gene region and cloned into plasmid pARC135.

The plasmid pARC135 (shown in FIG. 7) is composed of the pUC18 vector containing the yeast PGK promoter and terminator sequences separated by a unique Bgl II site.

First, the approximately 3.1 kb Hind III fragment of yeast (*S. cerevisiae*) containing the PGK gene was cloned into the Hind III site of pUC18 to create plasmid pSOC117 (also referred to herein as plasmid pARC117). Next, a Bgl II site was introduced by oligonucleotide mutagenesis upstream of the initiating ATG codon of the PGK gene contained within a mp19M13 clone, producing the change shown below in bold.

Native PGK Sequence:      Met Ser Leu
....ACAACAAAATATAAAAACA ATG TCT TTA
                              (SEQ ID NO:36)

New PGK Sequence:
....ACAACAAGATCTAAAAACA ATG TCT TTA
     Bgl II Site              (SEQ ID NO:37)

Then, an approximately 1.1 kb Bst XI fragment, carrying the introduced Bgl II PGK site, was excised from the mp19 clone and used to replace the homologous Bst XI fragment within plasmid pSOC117. Finally, the Bgl II fragment, containing the majority of the PGK structural gene, was removed by Bgl II digestion, and the plasmid was religated to yield plasmid pARC135. Plasmid pARC135 was digested with Nco I and Eco RI, the resulting gene was thereafter manipulated, as discussed below, to generate the plasmid pARC140R, which contains the *S. cerevisiae* phosphoglyceric acid kinase (PGK) promoter at the Bgl II site.

The experimental protocol for the construction of pARC140R is described below.

A. Hybridization/Annealing of the two oligonucleotide probes (oligonucleotide probes were not phosphorylated at the 5' end).

1) The two complementary oligonucleotide probes were annealed in 25 μl of solution containing:
   10 μl of oligonucleotide #1 (about 1 μg)
   10 μl of oligonucleotide #2 (about 1 μg)
   1.65 μl of 1M Tris-Cl$_2$ (pH 8.0)
   2.5 μl of 100 mM MgCl$_2$
   0.45 μl water 2) The probe solution was incubated at 65° C. for 10 minutes. Then it was cooled according to the following regime:
   20 minutes at 55° C.
   20 minutes at 42° C.
   20 minutes at 37° C.
   30 minutes at room temperature (24° C.)

B. An approximately 1112 bp fragment from Nco I to Eco RI in plasmid pARC285, containing an approximately 1040 bp (Nco I to Bam HI) sequence was excised and isolated from the gel. This approximately 1112 bp fragment contained the shortened version of the gene for phytoene synthase.

C. The annealed oligonucleotide probes were ligated overnight (15 hours at 15° C.) to the approximately 1112 bp (Nco I to Eco RI) fragment according to the following protocol:

| Annealed oligos | 25 μl |
| Nco I-Eco RI fragment | 20 μl (about 1 μg) |
| 10 X Legation Buffer | 5 μl (IBI, Corp.) |
| T4 Ligase (Boerhinger-Mannheim) | |

The result from the ligation was the following:

| Bgl II | Nco I | Bam HI | Eco RI |
| I------ | I---------------------- | I------ | I |

D. The mixture was subsequently phenol extracted, chloroform:isoamyl alcohol (24:1) extracted and then ethanol precipitated. The DNA pellet was resuspended in 27 μl water.

E. The DNA pellet was then digested for 30 minutes at 37° C. with Eco RI to remove any dimers that may have formed during the ligations.

| DNA fragment | 27 μl |
| Eco RI digestion buffer (BRL) | 3 μl |
| Eco RI enzyme (BRL) | 3 μl (30 U) |

F. The products of the Eco RI digestion were separated by electrophoresis on a 0.7 percent agarose gel. The fragment (about 1158 bp) was isolated from the gel.

G. This Bgl II to Eco RI fragment was cloned into the Bgl II and Eco RI sites of the plasmid pARC135 as follows. About 5 μg of plasmid pARC135 was digested with Bgl II and Eco RI and then separated on a 0.7 percent agarose gel. A DNA fragment (about 4 kb) was isolated. The approximately 1158 bp Bgl II to Eco RI fragment containing the full length phytoene synthase gene was cloned into the approximately 4 kb vector in the Bgl II and Eco RI sites according to the following protocol:

| pARC135 Bgl II/Eco RI digested | 10 μl (about 0.2 μg) |
| Bgl II to Eco RI fragment | 20 μl (about 0.5 μg) |
| 10 X legation buffer | 3 μl |
| T4 ligase | 2 μl (4 Units) |

The reaction was incubated overnight (about 15–18 hours) at 15° C.

H. The ligated DNA was cloned into DH5-alpha *E. coli* cells obtained from BRL.

I. Transformants were grown in the presence of 100 μg/ml of ampicillin. Colonies containing the cloned DNA fragment were identified by growing prospective clones in the presence of ampicillin, isolating plasmid DNA by the alkali lysis procedure and performing restriction enzyme analysis on the clones. The result of this cloning procedure was a plasmid named pARC140R that contained the desired genes.

Upstream from the ATG methionine codon, three adenine residues were introduced. Presence of adenine residues adjacent to the initiation codon has been correlated with genes that are highly expressed in *S. cerevisiae*. These residues had been inserted in the sequence to cause high level expression of a gene in *S. cerevisiae* (Hamilton et al., *Nucleic Acids Research*, 15:3581 1987). The plasmid pARC140R contains the *S. cerevisiae* promoter from the gene for phosphoglyceric acid kinase (PGK) adjacent to the gene for phytoene synthase.

The modified phytoene synthase structural gene was excised from plasmid pARC140R as an approximately 1158 bp Bgl II-Eco RI fragment, engineered and cloned into plasmid pARC306N to generate plasmid pARC140N. The plasmid pARC306N is similar to plasmid pARC306A except that instead of an Nco I site adjacent to the *E. coli* Rec 7 promoter, there is an Nde I site.

More specifically, plasmid pARC306N was digested with Nde I and then digested with S1 nuclease to blunt the ends of the former Nde I sites. The plasmid was thereafter digested with Eco RI to remove one of the blunt ends and provide an Eco RI sticky end.

Plasmid pARC140R was digested with Bgl II and then with S1 nuclease to blunt the resulting ends. The digested and blunt-ended plasmid was then further digested with Eco RI to remove one of the blunt ends and provide an Eco RI sticky end for the DNA containing the phytoene synthase structural gene. That structural gene was therefore in a fragment of about 1164 bp with a blunt end at one end and an Eco RI site at the other end.

The above phytoene synthase structural gene-containing DNA segment was ligated into the blunt end and to Eco RI portions of the above-digested plasmid pARC306N to operatively link the two DNA segments together and form plasmid pARC140N. The phytoene synthase structural gene-containing DNA segment can be excised from plasmid pARC140N as an approximately 1176 bp Hpa I-Eco RI fragment, an approximately 1238 bp Pvu II-Eco RI fragment or as a still larger fragment using one of the restriction sites in the polylinker region downstream from the Eco RI site (see, FIG. 6).

The plasmid pARC140N, was transferred into E. coli cells that contained the plasmid pARC139, in which part of the gene for phytoene synthase was deleted and, those E. coli cells were therefore incapable of producing any colored carotenoids. When plasmid pARC140N was added to those E. coli cells containing plasmid pARC139, the cells produced colored carotenoids. This demonstrated that the modified gene for phytoene synthase coded for a functional enzyme.

E. coli cells containing plasmid pARC140N were induced with nalidixic acid to produce large amounts of the phytoene synthase protein according to the protocol discussed hereinbefore. The protein fraction was isolated and analyzed by SDS-PAGE and revealed that the size of phytoene synthase protein is 38 kilodaltons.

Example 5. Phytoene Production in E. coli a. Method One—Plasmid containing the engineered genes for GGPP synthase and phytoene synthase A plasmid containing genes for both GGPP synthase and phytoene synthase, as well as an associated promoter regulatory region adjacent to a structural gene causes E. coli cells containing this plasmid to produce phytoene. An example of such a plasmid construct is the use of the structural gene for GGPP synthase from the plasmid pARC489D with a promoter that functions in E. coli adjacent to the 5' end of the structural gene for GGPP synthase. This construct is introduced into a common cloning vector such as pUC18. Where the structural genes are linked together, a single promoter can function in E. coli to express both gene products.

A before-described structural gene for phytoene synthase excised from the plasmid pARC140R is cloned adjacent to a promoter that functions in E. coli, such as Rec 7. This Rec 7 promoter-phytoene synthase heterologous gene is then introduced into a plasmid containing the gene for GGPP synthase. The plasmid containing both of these genes directs phytoene synthesis in E. coli. The two genes can also be placed end-to-end in E. coli under the control of a single promoter.

b. Method Two—Plasmid pARC376 with a defective gene for phytoene dehydrogenase-4H Phytoene production can occur with the native pARC376 plasmid in which the genes for GGPP synthase and phytoene synthase are functional and produce functional proteins, but in which the gene for phytoene dehydrogenase-4H is impaired, thereby impairing the production of lycopene from phytoene. A plasmid pARC376 derivative in which the gene for phytoene dehydrogenase-4H is deleted or in some other way impaired could not further metabolize the phytoene being produced in the E. coli cells due to the action of the genes for GGPP synthase and phytoene synthase. Under this condition, phytoene accumulates. The gene for phytoene dehydrogenase-4H is located approximately between the positions 7849 to 6380 of plasmid pARC376 as shown in FIG. 5.

By example, two different pARC376 derivative plasmids that contain deletions at the beginning of the gene for phytoene dehydrogenase-4H have been made as described before. One plasmid is pARC376-Bam 127, in which the approximately 2749 bp Bam HI fragment from about position 7775 to about 10524 (FIG. 5) was deleted. The other was plasmid pARC376-Pst 110 missing a Pst fragment at 7792-10791 (FIG. 5). These plasmids were constructed by partially digesting plasmid pARC376 with either Bam HI or Pst I, and ligating the respective DNA fragments together.

These deletions caused the gene for phytoene dehydrogenase-4H to be non-functional, since the beginning part of the gene was deleted. E. coli cells that contained either plasmid pARC376-Bam 127 or plasmid pARC376-Pst 110 produce phytoene. Phytoene is colorless and cells that produce phytoene have the same colorless character as normal E. coli cells. The ligation mixture was transformed into E. coli and any resulting colorless colonies were analyzed for the presence of phytoene. The presence of phytoene was confirmed by growing E. coli cells containing the plasmid, performing an extraction according to the following protocol, and identifying phytoene by HPLC analysis in the extract.

c. Identification of Phytoene Produced by Transformed E. coli i. Extraction from cells One hundred to 500 mg of lyophilized E. coli cells containing an above-described plasmid were resuspended in 3 ml of 7:2 acetone:methanol in 15 ml conical glass tube with teflon seal cap. 450–600 Micron glass beads (1:1 ratio with the cells) were added to the tube, which was covered with foil and vortexed for 2 minutes. After 5 minutes, the tube was spun in a table top centrifuge and the supernatant transferred to a foil covered glass vial. This extraction was repeated multiple times.

The entire pool of the extract was filtered through a 0.2 micron Acrodisc CR filter in a glass syringe, and the filtrate was dried under nitrogen. Utmost care was taken to protect the carotenoids/xanthophylls from light and heat.

ii. Identification

The presence of phytoene was monitored by thin layer chromatography (TLC) analysis in three different solvent systems using authentic phytoene as a reference.

The carotenoids/xanthophylls were separated by high pressure liquid chromatography (HPLC) with the aid of a Hewlett Packard C-18 Vydac analytical column (4.6×250 mm, 5 micron particle size). A linear gradient from 30 percent isopropanol and 70 percent acetonitrile:water (9:1) to 55 percent isopropanol and 45 percent acetonitrile:water (9:1) in 30 minutes (min) at 1 ml/min resolved most of the compounds of interest with the following retention times—zeaxanthin 8.7 min, lycopene 16.2 min, beta-carotene 18.1 min, phytofluene 19.9 min, phytoene 21.8 min, and the zeaxanthin diglucosides were clustered between 6 and 8 min.

The amount of phytoene produced in these cells averaged about 0.01 percent (dry weight).

Example 6. Phytoene Production in S. cerevisiae

S. cerevisiae does not normally produce carotenoids since it does not have the necessary functional genes for phytoene production. S. cerevisiae does, however, produce farnesyl pyrophosphate (FPP). For phytoene production to occur in S. cerevisiae, the genes for GGPP synthase and phytoene synthase need to be transferred into the S. cerevisiae cells in the proper orientation to permit the expression of functional enzymes.

Promoter sequences that function in S. cerevisiae need to be placed adjacent to the 5' end of the structural genes for GGPP synthase and phytoene synthase and termination sequences can also be placed at the 3' ends of the genes. The genes for GGPP synthase and phytoene synthase that contain the proper regulatory sequences for expression in *S. cerevisiae* then are transferred to the *S. cerevisiae* cells.

a. Construction of Plasmid pARC145B

The vector pSOC713 (FIG. 8), was made by first using Klenow polymerase to make blunt ends on the Eco RI fragment of the yeast B-form 2-micron circle that contains the 2-micron origin of replication. Thus, the blunt-ended fragment was cloned into the Sma I site of pUC8. The 2-micron fragment was removed from the pUC8 construct by cleavage with Eco RI and Bam HI. This Eco RI-Bam HI fragment was ligated to the Eco RI-Bgl II fragment of yeast DNA which contains the TRP 1 gene. The DNA containing the fused TRP 1 to 2-micron fragment was ligated as an Eco RI fragment into the Eco RI site of pUC18. Finally, a region of the yeast genome, containing the divergently-facing GAL 10 and GAL 1 promoters was ligated as an Eco RI to Bam HI fragment into the above TRP 1/2-micron/pUC18 plasmid, which had been cleaved with Eco RI and Bam HI. The restriction map of plasmid pSOC713 is shown in FIG. 8.

Three modifications were made to plasmid pSOC713 to yield plasmid pARC145B (FIG. 9). First, plasmid pSOC713 was partially digested with Eco RI and the ends were made blunt with Klenow polymerase and self-ligated. The resultant plasmid contained a unique Eco RI site adjacent to the GAL 1 promoter region. This plasmid was cleaved with Eco RI and the synthetic oligonucleotide shown below,

```
5'  AATTCCCGGGCCATGGC  3'       (SEQ ID NO:38)
3'      GGGCCCGGTACCGTTAA  5'   (SEQ ID NO:39)
``` was ligated into the Eco RI site. This regenerated one Eco RI site followed by Sma I and Nco I sites. Finally, the single Bam HI site was cut, filled in with Klenow polymerase, and the Bgl II synthetic linker oligonucleotide

```
CAGATCTG

GTCTACTG
``` was ligated, cut with Bgl II, and then self-ligated to make a Bgl II site flanked by two Bam HI sites. The restriction map of plasmid pARC145B is shown in FIG. 9.

b. Construction of Plasmid pARC145G

The engineered gene for GGPP synthase contained in plasmid pARC489D, which encoded the most active version of the enzyme in *E. coli* above, was transferred to the *S. cerevisiae* vector pARC145B to generate plasmid pARC145F. This was accomplished by digestion of plasmid pARC489D with Nco I and Pvu II to obtain the approximately 1000 bp Nco I-Pvu II restriction fragment that contained the GGPP synthase structural gene. An Nco I linker was added to the Pvu II site of the restriction fragment to make that fragment an Nco I-Nco I fragment containing about 1010 bp. The GGPP synthase gene was cloned adjacent to the *S. cerevisiae* divergent promoter region GAL 10 and GAL 1 so that the GGPP synthase gene would be expressed in *S. cerevisiae* using the GAL 10 promoter.

The gene for phytoene synthase from plasmid pARC140R (Example 2) was excised and placed adjacent to the other side of the GAL 1 promoter of plasmid pARC145F so that the phytoene synthase gene would also be expressed using the GAL 1 promoter. Thus, the transcription termination sequence from the *S. cerevisiae* gene PGK was cloned at the 3' end of the gene for phytoene synthase.

More specifically, plasmid pARC145F was digested with Bgl II and Sph I, whose restriction sites are illustrated in FIG. 9 for precursor plasmid pARC145B. The phytoene synthase structural gene was excised from plasmid pARC140R as an approximately 1158 Bgl II-Eco RI fragment; the same structural gene is present in the approximately 1176 bp Hpa I-Eco RI fragment of plasmid pARC140N. The approximately 500 bp PGK termination sequence from another plasmid, pARC117, was excised as an Eco RI-Sph I fragment such as the same fragment shown in plasmid pARC135 of FIG. 7. The Bgl II-Sph I digested plasmid pARC145F, the Bgl II-Eco RI about 1158 bp plasmid pARC140R fragment and the about 500 bp Eco RI-Sph I PGK termination sequence were triligated to operatively link the three sequences together.

This ligation placed the phytoene synthase structural gene adjacent to and under the control of the GAL 1 promoter at the 5' end of the structural gene. The PGK termination sequence was placed at the 3' end of the phytoene synthase structural gene. The resulting plasmid, now containing both of the genes required for phytoene production under control of the GAL 10 and GAL 1 divergent promoters, was named plasmid pARC145G, and is shown in FIG. 10. Other relevant features of plasmid pARC145G include the 2 micron origin of replication of *S. cerevisiae* and the TRP 1 gene of *S. cerevisiae* as a selectable marker.

The plasmid pARC145G was transferred into the *S. cerevisiae* strain YPH499 (provided by Dr. Phillip Heiter, Johns Hopkins University) that lacked a functional TRP 1 gene. This strain was able to utilize galactose as a carbon source. Transformants were isolated, and the cells were grown in the presence of galactose to induce the GAL 10 and GAL 1 promoters to express the genes for phytoene production.

The *S. cerevisiae* cells were grown on the media described below to produce phytoene. YPH499 is a strain of yeast that contains an impaired TRP 1 gene and an impaired URA 3 gene, and is able to utilize galactose as carbon and energy sources. This strain requires tryptophan and uracil in the growth medium in order to grow. Alternatively, these strains can be grown if they are transformed with a plasmid (or plasmids) containing a normal copy of either the TRP 1 gene, but not a normal copy of the URA 3 gene, in which case the cells require uracil to be added to the growth medium, or the URA 3 gene, but not a normal copy of the TRP 1 gene, in which case the cells need to have tryptophan added to the growth medium.

There are four different media used to grow this strain of Saccharomyces:

Medium 1 is used if the cells contain no further URA 3 or TRP 1 genes.

Medium 2 is used if the cells contain a plasmid(s) with only the TRP 1 gene.

Medium 3 is used if the cells contain a plasmid(s) with only the URA 3 gene.

Medium 4 is used if the cells contain a plasmid(s) with both the TRP 1 and the URA 3 genes.

The media constituents are as follows:

Basic Constituents:
  0.67% Yeast Nitrogen Base without Amino Acids (Source Difco, #0919-15);
  2% Galactose; and
  720 mg/l Dropout Mixture, \* Dropout Mixtures

| For Medium 1 (Complete) | |
|---|---|
| Constituent | Amount (mg) |
| adenine | 400 |
| uracil | 400 |
| tryptophan | 400 |
| histidine | 400 |
| arginine | 400 |
| methionine | 400 |
| tyrosine | 600 |
| leucine | 1200 |
| lysine | 600 |
| phenylalanine | 1000 |
| threonine | 4000 |
| aspartic acid | 2000 |
| For Medium 2, without the tryptophan. | |
| For Medium 3, without the uracil. | |
| For Medium 4, without both tryptophan and uracil. | |

To prepare a dropout mixture all of the desired constituents were added to a mortar and ground thoroughly with a pestle. The constituents were thoroughly mixed and 720 mg of the dropout mixture were added for each liter of medium.

The plasmid pARC145G contains both the GGPP synthase and phytoene synthase genes and a normal copy of the TRP 1 gene. Saccharomyces cells containing plasmid pARC145G were grown in Medium 2 with 2 percent galactose.

The S. cerevisiae cells were analyzed for the presence of phytoene. A total of 0.12 percent (dry weight) phytoene and related compounds having superimposable UV-Vis spectra as phytoene was found in the cells.

Example 7. Phytoene Production in *Pichia pastoris*

The above method is also extendable to other yeasts. One yeast system that serves as an example is the methylotrophic yeast, *Pichia pastoris*.

To produce phytoene in *P. pastoris*, structural genes for both GGPP synthase and phytoene synthase are placed under the control of regulatory sequences that direct expression of structural genes in Pichia. The resultant expression-competent forms of those genes are introduced into Pichia cells.

For example, the transformation and expression system described by Cregg et al., *Biotechnology* 5:479–485 (1987); *Molecular and Cellular Biology* 12:3376–3385 (1987) can be used. A structural gene for GGPP synthase such as that from plasmid p489D is placed downstream from the alcohol oxidase gene (AOX1) promoter and upstream from the transcription terminator sequence of the same AOX1 gene. Similarly, a structural gene for phytoene synthase such as that from plasmid 140N is placed between an AOX1 promoter and terminator. Both of these genes and their flanking regulatory regions are then introduced into a plasmid that carries both the *P. pastoris* HIS4 gene and a *P. pastoris* ARS sequence (Autonomously Replicating Sequence), which permit plasmid replication within *P. pastoris* cells [Cregg et al., *Molecular and Cellular Biology*, 12:3376–3385 (1987)].

The vector also contains appropriate portions of a plasmid such as pBR322 to permit growth of the plasmid in *E. coli* cells. The final resultant plasmid carrying GGPP synthase and phytoene synthase genes, as well as the various additional elements described above, is illustratively transformed into a his4 mutant of *P. pastoris*, i.e. cells of a strain lacking a functional histidinol dehydrogenase gene.

After selecting transformant colonies on media lacking histidine, cells are grown on media lacking histidine, but containing methanol as described Cregg et al., *Molecular and Cellular Biology*, 12:3376–3385 (1987), to induce the AOX1 promoters. The induced AOX1 promoters cause expression of the enzymes GGPP synthase and phytoene synthase and the production of phytoene in *P. pastoris*.

Both GGPP synthase and phytoene synthase genes can also be introduced by integrative transformation, which does not require the use of an ARS sequence, as described by Cregg et al., *Molecular and Cellular Biology*, 12:3376–3385 (1987).

Example 8. Phytoene Production in *A. nidulans*

The genes encoding GGPP synthase and phytoene synthase as discussed before can be used to synthesize and accumulate phytoene in fungi such as *Aspergillus nidulans*. Genes are transferred to Aspergillus by integration.

For example, the structural gene for GGPP synthase is introduced into the *E. coli* plasmid pBR322. The promoter from a cloned Aspergillus gene such as argB [Upshall et al., *Mol. Gen. Genet.* 204:349–354 (1986)] is placed into the plasmid adjacent to the GGPP synthase structural gene. Thus, the GGPP synthase gene is now under the control of the Aspergillus argB promoter.

Next, the entire cloned amds gene [Corrick et al., *Gene* 53:63–71 (1987)] is introduced into the plasmid. The presence of the amds gene permits acetamide to be used as a sole carbon or nitrogen source, thus providing a means for selecting those Aspergillus cells that have become stably transformed with the amds-containing plasmid.

Thus, the plasmid so prepared contains the Aspergillus argB promoter fused to the GGPP synthase gene and the amds gene present for selection of Aspergillus transformants. Aspergillus is then transformed with this plasmid according to the method of Ballance et al., *Biochem. Biophys. Res. Commun.* 112:284–289 (1983).

The phytoene synthase structural gene is similarly introduced into the *E. coli* plasmid pBR322. The promoter for the cloned Aspergillus argB gene [Upshall et al., *Mol. Gen. Genet*, 204:349–354 (1986)] is placed immediately adjacent to the phytoene synthase structural gene. Thus, the phytoene synthase structural gene is controlled by the Aspergillus argB promoter.

The entire, cloned Aspergillus trpC gene [Hamer and Timberlake, *Mol. Cell. Biol.*, 7:2352–2359 (1987)] is introduced into the plasmid. The trpC gene permits selection of the integrated plasmid by virtue of permitting transformed trpC mutant Aspergillus cells to now grow in the absence of tryptophan. The Aspergillus strain, already transformed with the plasmid containing the GGPP synthase gene, is now capable of synthesizing phytoene.

Example 9 Phytoene Synthase Production in Higher Plants a. Construction of the plasmid pATC1615

Plasmid pARC283 was first constructed in order to provide an appropriate template for the polymerase chain reaction (PCR), below. The construction of plasmid pARC283 used the approximately 1534 bp Bgl II to Bam HI fragment of plasmid pARC376 (from about position 6836 to about position 5302 of FIG. 5). Polylinker fragments, which contain multiple unique restriction sites, were ligated to the ends of this Bgl II-Bam HI fragment. The resulting fragment was digested with Eco RI and cloned into the Eco RI site of plasmid pBR322. The resulting plasmid was named pARC283.

The phytoene synthase structural gene of this plasmid was modified to introduce the restriction site Sph I at the initiation methionine codon and a Sal I restriction site at the 3' end of the gene. To accomplish these modifications, the Eco RI-Eco RI fragment was excised from plasmid pARC283. This fragment was isolated on agarose gel electrophoresis and used as the template for PCR. The following oligonucleotide probe was used to create the Sph I site at the ATG start codon of the phytoene synthase gene:

5' TCG CAT GCG CCA ACG CCG CTG CTT GAC CAC GC 3',
        Sph I              (SEQ ID NO:40)

in which bold letters indicate changed nucleotides. This modification changed the second residue from the serine shown in FIG. 4 to an arginine. The following oligonucleotide probe was used to create the Sal I site at the 3' end of the gene:

5' CTG TCG ACG GCT ACT GAG CGG CTC TAC GTC 3'
       Sal I              (SEQ ID NO:41)

The introduction of a Sal I site at the 3' end of the phytoene synthase gene changed the DNA sequence as indicated below:

Original Sequence:
5' GAC GTA GAG CCG CTT CAG GTAGCC CCG GCG 3'
                                    (SEQ ID NO:42)

New Sequence:
5' CAC GTA GAG CCG CTC AGT AGC CGT CGA CAG 3'
                                    (SEQ ID NO:43)     , in a which bold-faced letter in the new sequence indicates an altered base.

Although there are only 15 nucleotides of the PCR probe that hybridize exactly to the original 3' sequence, the hybridization conditions under which the PCR was performed makes this amount of hybridization sufficient for the PCR to function appropriately to introduce the alterations noted in the sequence.

The probes were resuspended in a volume of sterile water such that the final concentration of each probe was 10 pmoles/μl. The PCR reaction was conducted as described in Example 3, part b.

b. Cloning of the PCR Produced DNA Fragment

The DNA produced by the PCR reaction was digested with Sph I and Sal I. This about 1065 bp Sph I-Sal I PCR generated fragment was isolated and recovered from an agarose gel. Plasmid pUC18 (Pharmacia) was likewise digested with Sph I and Sal I. The Sph I-Sal I PCR fragment was cloned into the Sph I-Sal I sites of plasmid pUC18. The resulting plasmid was named pATC1611.

c. Proof of Functional Genetically Engineered Phytoene Synthase Gene

The proper functioning of the phytoene synthase gene of plasmid pATC1611 was assayed by cloning the PCR modified gene into an *E. coli* expression vector. This was done by first digesting plasmid pATC1611 with Hind III and Eco-RI. The resulting Hind III-Eco RI fragment was isolated and recovered from an agarose gel, and treated with the Klenow fragment of DNA polymerase I to fill in the fragment termini to create blunt ends.

This blunt ended fragment was then cloned into plasmid pDR540 (Pharmacia), A plasmid that contains the TAC promoter active in *E. coli*. Thus, plasmid pDR540 was cut with Bam HI and the Klenow fragment was used to fill in the ends, as above. The now blunt ended originally Hind III-Eco RI fragment containing the phytoene synthase gene was ligated to the blunt ended Bam HI-treated pDR540. This plasmid construct was cut with Hind III to provide a Hind III-Hind III fragment that contained the phytoene synthase gene and the TAC promoter. That Hind III-Hind III fragment was then ligated into the Hind III site of plasmid pARC139.

Plasmid pARC139, discussed in Example 3, carries a deletion in the phytoene synthase gene. Addition of a functional copy of the phytoene synthase gene to plasmid pARC139 restores the ability of *E. coli* cells transformed with such a construct to produce colored carotenoids. The PCR modified phytoene synthase gene led to the production of colored carotenoids in *E. coli*, indicating that the modifications introduced into the gene via the PCR process did not affect the production of phytoene synthase from the modified gene.

d. Construction of Plasmid pATC1615

Plasmid pATC1611 was digested with Sph I and Hinc II. The resulting Sph I-Hind II fragment was cloned into the Sph I and Hinc II sites of plasmid pATC212, discussed in Example 3, to produce plasmid pATC1614.

Plasmid pATC1614 was digested with Xba I, generating a Xba I fragment which contained the 35S promoter, the transit peptide sequence, the phytoene synthase gene, and the NOS polyadenylation sequence. This Xba I fragment was cloned into the Xba I site of plasmid pGA482 (Pharmacia). The resulting plasmid was named pATC1615.

e. Construction of Plasmid pATC1620

Plasmid pATC1614, described above, was digested with Sal I. This generated a Sal I fragment containing the transit peptide sequence fused to the 5' end of the phytoene synthase gene. This Sal I fragment was treated with the Klenow fragment of DNA polymerase I to generate blunt ends.

Likewise, plasmid pNCN (Pharmacia) was digested with Bam HI and Sal I and treated with the Klenow fragment. The blunt ended Sal I fragment was ligated to the blunt ended plasmid pNCN to create plasmid pATC1618. This plasmid contains the NOS promoter sequence of *Agrobacterium tumefaciens* fused to the 5' end of the transit peptide sequence-phytoene synthase construct, and the NOS polyadenylation sequence fused to the 3' end of the gene.

This entire gene construct, namely, the NOS promoter sequence, the transit peptide sequence, the phytoene synthase structural gene, and the NOS polyadenylation sequence was removed from plasmid pATC1618 as a Hind III fragment. This Hind III fragment was cloned into the Hind III site of plasmid pGA482, to generate the plasmid pATC1620.

f. Production of Lutein in Plants

Plasmids pATC1615 and pATC1620 were transformed into *Agrobacterium tumefaciens* LBA4404 (Clontech, Inc.) according to standard protocols. Agrobacterium cells containing the plasmids with the phytoene synthase gene constructs were transferred by infection of tobacco leaf discs using the method of Horsch et al., *Science*, 227:1229–1231 (1985). During the infection process, the entire DNA segment between the left and right borders of the pGA482 plasmid is transfected into the plant cells. Transfected plant cells are selected for kanamycin resistance.

Western blot analyses of transformed tobacco plant chloroplasts indicated the presence of enhanced amounts of phytoene synthase.

The level of lutein in these transgenic plants was examined. Lutein, or xanthophyll, is one of the most widespread carotenoids in nature. Lutein is usually isolated by chromatography from nettles, algae, and the petals of many yellow flowers. Wildtype, untransformed tobacco plants average 0.13% of dry weight lutein. Viable transgenic tobacco plants transformed with plasmid pATC1615 contained an average of 0.16 percent of dryweight lutein, whereas tobacco plants transformed with pATC1620 contained an average of 0.21 percent of dryweight lutein, an average of over 1.6 times the wildtype levels. Some transformed tobacco plants had lutein levels 2 to 3 times higher than wildtype plants, with the highest level being 0.37% of dryweight lutein. These transgenic tobacco plants provide a new high level source of lutein. Several of the transgenic plants had orange patches or were themselves orange and were not viable.

Unexpectedly, transformed tobacco plants that exhibited high levels of lutein also exhibited high levels of chlorophyll that were on the order of 2 to 3 times higher than untransformed tobacco plants. The reason for the elevated chlorophyll levels is unclear, but it appears that an increase in the levels of the phytoene leads to an increase in the carotenoid and chlorophyll contents in the transformed plants.

g. Production in the Plant Cytoplasm

To prepare phytoene synthase in the cytoplasm, the carotenoid genes described before are introduced into appropriate vector(s), as also described above for chloroplasts, using identical techniques, except that the transit peptide is eliminated. Because they are not targeted to the chloroplast, the enzymes remain in the cytoplasm, and can be isolated from the cytosol.

Although the present invention has now been described in terms of certain preferred embodiments, and exemplified with respect thereto, one skilled in the art will readily appreciate that various modifications, changes, omissions and substitutions may be made without departing from the spirit thereof.

What is claimed is:

1. A purified and isolated DNA segment comprising a nucleotide sequence that contains at least 850 base pairs that define the structural gene for the *Erwinia herbicola* enzyme geranylgeranyl pyrophosphate synthase that is present in a restriction endonuclease fragment selected from the group consisting of the approximately 1029 base pair Nco I-Eco RV restriction fragment of plasmid pARC417BH having ATCC Accession No. 40755, the approximately 1000 base pair Nco I-Pvu II restriction fragment of plasmid pARC498D having ATCC Accession No. 40757 and the approximately 1150 base pair Nco I-Pvu II restriction fragment of plasmid pARC489B having ATCC Accession No. 40758, said geranylgeranyl pyrophosphate synthase converting isopentyl pyrophosphate and farnesyl pyrophosphate into geranylgeranyl pyrophosphate.

2. A purified and isolated DNA segment comprising a nucleotide sequence that contains at least 850 base pairs that define a structural gene for the *Erwinia herbicola* enzyme geranylgeranyl pyrophosphate synthase (E.C.2.5.1.29) that is present in a plasmid selected from the group consisting of pARC417BH having ATCC Accession No. 40755, pARC489B having ATCC Accession No. 40758 and pARC489D having ATCC Accession No. 40757 or a DNA variant that has at least 80 percent identity to said gene and hybridizes with said gene under high stringency conditions comprising hybridization at a temperature of 68° C. in 6XSSC and a final wash at a temperature of 68° C. in 0.1XSSC, said nucleotide sequence encoding an enzyme that converts isopentyl pyrophosphate and farnesyl pyrophosphate into geranylgeranyl pyrophosphate.

3. A recombinant DNA molecule comprising a vector operatively linked to an exogenous DNA segment that contains at least about 850 base pairs defining a structural gene for the *Erwinia herbicola* enzyme geranylgeranyl pyrophosphate synthase (E.C.2.5.1.29) that is present in a plasmid selected from the group consisting of pARC417BH having ATCC Accession No. 40755, pARC489B having ATCC Accession No. 4075 and pARC489D having ATCC Accession No. 40757 or a DNA variant that has at least 80 percent identity to said gene and hybridizes with said gene under high stringency conditions comprising hybridization with said gene under high stringency conditions comprising hybridization at a temperature of 68° C. in 6XSSC and a final wash at a temperature of 68° C. in 0.1XSSC, said nucleotide sequence encoding an enzyme that converts isopentyl pyrophosphate and farnesyl pyrophosphate into geranylgeranyl pyrophosphate, and a promoter for driving the expression of said enzyme in a higher plant.

4. A transformed higher plant whose genome contains
   (i) a nucleotide sequence that encodes the structural gene for the *Erwinia herbicola* enzyme geranylgeranyl pyrophosphate synthase (E.C.2.5.1.29) present in a plasmid selected from the group consisting of pARC417BH having ATCC Accession No. 40755, pARC489B having ATCC Accession No. 40758 and pARC489D having ATCC Accession No. 40757 or a DNA variant that has at least 80 percent identity to said gene and hybridizes with said gene under high stringency conditions comprising hybridization at a temperature of 68° C. in 6XSSC and a final wash at a temperature of 68° C. in 0.1XSSC, said nucleotide sequence encoding an enzyme that converts isopentyl pyrophosphate and farnesyl pyrophosphate into geranylgeranyl pyrophosphate, and
   (ii) a promoter that expresses said gene in said transformed plant.

5. The transformed plant according to claim 4 that is selected from the group consisting of alfalfa and tobacco.

6. A purified and isolated DNA segment comprising a nucleotide sequence that contains at least 1000 base pairs that define the structural gene for the *Erwinia herbicola* enzyme phytoene synthase present in a restriction endonuclease fragment that is the approximately 1040 base pair NcoI-Bam HI restriction fragment of plasmid pARC285 having ATCC Accession No. 40756 or the approximately 1176 base pair Hpa I-Eco RI restriction fragment of plasmid pARC140N having Accession No. 40754, said enzyme converting geranylgeranyl pyrophosphate into phytoene.

7. A purified and isolated DNA segment comprising a nucleotide sequence that contains at least 1000 base pairs that define a structural gene for the *Erwinia herbicola* enzyme phytoene synthase present in plasmid pARC285 having ATCC Accession No. 40756 or plasmid pARC140N having Accession No. 40754, or a DNA variant that has at least 80 percent identity to said gene and hybridizes with said gene under high stringency conditions comprising hybridization at a temperature of 68° C. in 6XSSC and a final wash at a temperature of 68° C. in 0.1XSSC, said nucleotide sequence encoding an enzyme that converts geranylgeranyl pyrophosphate into phytoene.

8. A recombinant DNA molecule comprising a vector operatively linked to an exogenous DNA segment that contains at least about 1000 base pairs defining a structural gene for the *Erwinia herbicola* enzyme phytoene synthase that is present in plasmid pARC285 having ATCC Accession No. 40756 or plasmid pARC140N having ATCC Accession No. 40754, or a DNA variant that has at least 80 percent identity to said gene and hybridizes with said gene under high stringency conditions comprising hybridization at a temperature of 68° C. in 6XSSC and a final wash at a temperature of 68° C. in 0.1XSSC, said nucleotide sequence encoding an enzyme that converts geranylgeranyl pyrophosphate into phytoene, and a promoter for driving the expression of said gene in a higher plant.

9. A transformed higher plant whose genome contains
   (i) a nucleotide sequence that encodes the structural gene for the *Erwinia herbicola* enzyme phytoene synthase present in plasmid pARC285 having ATCC Accession No. 40756 or plasmid pARC140N having ATCC Accession No. 40754, or a DNA variant that has at least 80 percent identity to said gene and hybridizes with said gene under high stringency conditions comprising hybridization at a temperature of about 68° C. in 6XSSC and a final wash at a temperature of 68° C. in 0.1XSSC, said nucleotide sequence encoding an enzyme that converts geranylgeranyl pyrophosphate into phytoene, and
   (ii) a promoter that expresses said gene in said transformed plant.

10. The transformed plant according to claim 9 that is selected from the group consisting of alfalfa and tobacco.

11. Plasmid pARC417BH having ATCC accession number 40755.

12. Plasmid pARC489B having ATCC accession number 40758.

13. Plasmid pARC489D having ATCC accession number 40757.

14. Plasmid pARC140N having ATCC accession number 40754.

15. Plasmid pARC285 having ATCC accession number 40756.

* * * * *

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
    ( A ) LENGTH: 1157 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

```
                                                                              A G A        3
T C T A A A G G C A   C A G C G T C T C A   T G C T T C G C A C   A A T G T A A A A C   T G C T T C A G A A   C C T G G C G A G A     6 3
G C T A T C C G C G   C G G T C T A C G G   T T A A C T G A T A   C T A A A A G A C A   A T T C A G C G G G   T A A C C T T G C A    1 2 3
A T G G T G A G T G   G C A G T A A A G C   G G G C G T T T C G   C C T C A T C G C G   A A A T A G A G G T   A A T G A G A C A A    1 8 3
T C C A T T G A C G   A T C A C C T G G C   T G G C C T G T T A   C C T G A A A C C G   A C A G C C A G G A   T A T C G T C A G C    2 4 3
C T T G C G A T G C   G T G A A G G C G T   C A T G G C A C C C   G G T A A A C G G A   T C C G T C C G C T   G C T G A T G C T G    3 0 3
C T G G C C G C C C   G C G A C C T C C G   C T A C C A G G G C   A G T A T G C C T A   C G C T G C T C G A   T C T C G C C T G C    3 6 3
G C C G T T G A A C   T G A C C C A T A C   C G C G T C G C T G   A T G C T C G A C G   A C A T G C C C T G   C A T G G A C A C C    4 2 3
G C C G A G C T G C   G C C G C G G T C A   G C C C A C T A C C   C A C A A A A A A T   T T G G T G A G A G   C G T G G C G A T C    4 8 3
C T T G C C T C C G   T T G G G C T G C T   C T C T A A A G C C   T T T G G T C T G A   T C G C C G C C A C   C G G C G A T C T G    5 4 3
C C G G G G G A G A   G G C G T G C C C A   G G C G G T C A A C   G A G C T C T C T A   C C G C C G T G G G   G C T G C A G G G C    6 0 3
C T G G T A C T G G   G G C A G T T T C G   C G A T C T T A A C   G A T G C C G C C C   T C G A C C G T A C   C C C T G A C G C T    6 6 3
A T C C T C A G C A   C C A A C C A C C T   C A A G A C C G G C   A T T C T G T T C A   G C G C G A T G C T   G C A G A T C G T C    7 2 3
G C C A T T G C T T   C C G C C T C G T C   G C C G A G C A C G   C G A G A G A C G C   T G C A C G C C T T   C G C C C T C G A C    7 8 3
T T C G G C C A G G   C G T T T C A A C T   G C T G G A C G A T   C T G C G T G A C G   A T C A C C C G G A   A A C C G G T A A A    8 4 3
G A T C G C A A T A   A G G A C G C G G G   A A A A T C G A C G   C T G G T C A A C C   G G C T G G G C G C   A G A C G C G G C C    9 0 3
C G G C A A A A G C   T G C G C G A G C A   T A T T G A T T C C   G C C G A C A A A C   A C C T C A C T T T   T G C C T G T C C G    9 6 3
C A G G G C G G C G   C C A T C C G A C A   G T T T A T G C A T   C T G T G G T T T G   G C C A T C A C C T   T G C C G A C T G G   1 0 2 3
T C A C C G G T C A   T G A A A A T C G C   C T G A T A C C G C   C C T T T T G G G T   T C A A G C A G T A   C A T A A C G A T G   1 0 8 3
```

GAACCACATT ACAGGAGTAG TGATGAATGA AGGACGAGCG CCTTGTTCAG CGTAAGAACG 1143

ATCATCTGGA TATC 1157

( 2 ) INFORMATION FOR SEQ ID NO:2:

( i ) SEQUENCE CHARACTERISTICS:
( A ) LENGTH: 307 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Val | Ser | Gly | Ser | Lys | Ala | Gly | Val | Ser | Pro | His | Arg | Glu | Ile | Glu |
|---|---|---|---|---|---|---|---|---|---|---|---|---|---|---|---|
| 1 | | | | 5 | | | | | 10 | | | | | 15 | |
| Val | Met | Arg | Gln | Ser | Ile | Asp | Asp | His | Leu | Ala | Gly | Leu | Leu | Pro | Glu |
| | | | 20 | | | | | 25 | | | | | 30 | | |
| Thr | Asp | Ser | Gln | Asp | Ile | Val | Ser | Leu | Ala | Met | Arg | Glu | Gly | Val | Met |
| | | 35 | | | | | 40 | | | | | 45 | | | |
| Ala | Pro | Gly | Lys | Arg | Ile | Arg | Pro | Leu | Leu | Met | Leu | Leu | Ala | Ala | Arg |
| | 50 | | | | | 55 | | | | | 60 | | | | |
| Asp | Leu | Arg | Tyr | Gln | Gly | Ser | Met | Pro | Thr | Leu | Leu | Asp | Leu | Ala | Cys |
| 65 | | | | | 70 | | | | | 75 | | | | | 80 |
| Ala | Val | Glu | Leu | Thr | His | Thr | Ala | Ser | Leu | Met | Leu | Asp | Asp | Met | Pro |
| | | | | 85 | | | | | 90 | | | | | 95 | |
| Cys | Met | Asp | Asn | Ala | Glu | Leu | Arg | Arg | Gly | Gln | Pro | Thr | Thr | His | Lys |
| | | | | 100 | | | | | 105 | | | | | 110 | |
| Lys | Phe | Gly | Glu | Ser | Val | Ala | Ile | Leu | Ala | Ser | Val | Gly | Leu | Leu | Ser |
| | | | 115 | | | | | 120 | | | | | 125 | | |
| Lys | Ala | Phe | Gly | Leu | Ile | Ala | Ala | Thr | Gly | Asp | Leu | Pro | Gly | Glu | Arg |
| | 130 | | | | | 135 | | | | | 140 | | | | |
| Arg | Ala | Gln | Ala | Val | Asn | Glu | Leu | Ser | Thr | Ala | Val | Gly | Leu | Gln | Gly |
| 145 | | | | | 150 | | | | | 155 | | | | | 160 |
| Leu | Val | Leu | Gly | Gln | Phe | Arg | Asp | Leu | Asn | Asp | Ala | Ala | Leu | Asp | Arg |
| | | | | 165 | | | | | 170 | | | | | 175 | |
| Thr | Pro | Asp | Ala | Ile | Leu | Ser | Thr | Asn | His | Leu | Lys | Thr | Gly | Ile | Leu |
| | | | 180 | | | | | 185 | | | | | 190 | | |
| Phe | Ser | Ala | Met | Leu | Gln | Ile | Val | Ala | Ile | Ala | Ser | Ala | Ser | Ser | Pro |
| | | 195 | | | | | 200 | | | | | 205 | | | |
| Ser | Thr | Arg | Glu | Thr | Leu | His | Ala | Phe | Ala | Leu | Asp | Phe | Gly | Gln | Ala |
| | 210 | | | | | 215 | | | | | 220 | | | | |
| Phe | Gln | Leu | Leu | Asp | Asp | Leu | Arg | Asp | Asp | His | Pro | Glu | Thr | Gly | Lys |
| 225 | | | | | 230 | | | | | 235 | | | | | 240 |
| Asp | Arg | Asn | Lys | Asp | Ala | Gly | Lys | Ser | Thr | Leu | Val | Asn | Arg | Leu | Gly |
| | | | | 245 | | | | | 250 | | | | | 255 | |
| Ala | Asp | Ala | Ala | Arg | Gln | Lys | Leu | Arg | Glu | His | Ile | Asp | Ser | Ala | Asp |
| | | | 260 | | | | | 265 | | | | | 270 | | |
| Lys | His | Leu | Thr | Phe | Ala | Cys | Pro | Gln | Gly | Gly | Ala | Ile | Arg | Gln | Phe |
| | | 275 | | | | | 280 | | | | | 285 | | | |
| Met | His | Leu | Trp | Phe | Gly | His | His | Leu | Ala | Asp | Trp | Ser | Pro | Val | Met |
| | 290 | | | | | 295 | | | | | 300 | | | | |
| Lys | Ile | Ala | | | | | | | | | | | | | |
| 305 | | | | | | | | | | | | | | | |

( 2 ) INFORMATION FOR SEQ ID NO:3:

(i) SEQUENCE CHARACTERISTICS:
     (A) LENGTH: 1157 base pairs
     (B) TYPE: nucleic acid
     (C) STRANDEDNESS: single
     (D) TOPOLOGY: linear (ii) MOLECULE TYPE: DNA (genomic)

(xi) SEQUENCE DESCRIPTION: SEQ ID NO:3:

```
                                        AGATCTAAAG GCACAGCGTC TCATGCTTCG     30
CACAATGTAA AACTGCTTCA GAACCTGGCG AGAGCTATCC GCGCGGTCTA CGGTTAACTG     90
ATACTAAAAG ACAATTCAGC GGGTAACCTT GCAATGGTGA GTGGCAGTAA AGCGGGCGTC    150
ATGGCCGAAT TCGAAATAGA GGTAATGAGA CAATCCATTG ACGATCACCT GGCTGGCCTG    210
TTACCTGAAA CCGACAGCCA GGATATCGTC AGCCTTGCGA TGCGTGAAGG CGTCATGGCA    270
CCCGGTAAAC GGATCCGTCC GCTGCTGATG CTGCTGGCCG CCCGCGACCT CCGCTACCAG    330
GGCAGTATGC CTACGCTGCT CGATCTCGCC TGCGCCGTTG AACTGACCCA TACCGCGTCG    390
CTGATGCTCG ACGACATGCC CTGCATGGAC ACCGCCGAGC TGCGCCGCGG TCAGCCCACT    450
ACCCACAAAA AATTTGGTGA GAGCGTGGCG ATCCTTGCCT CCGTTGGGCT GCTCTCTAAA    510
GCCTTTGGTC TGATCGCCGC CACCGGCGAT CTGCCGGGGG AGAGGCGTGC CCAGGCGGTC    570
AACGAGCTCT CTACCGCCGT GGGGCTGCAG GGCCTGGTAC TGGGGCAGTT CGCGATCTT     630
AACGATGCCG CCCTCGACCG TACCCCTGAC GCTATCCTCA GCACCAACCA CCTCAAGACC    690
GGCATTCTGT TCAGCGCGAT GCTGCAGATC GTCGCCATTG CTTCCGCCTC GTCGCCGAGC    750
ACGCGAGAGA CGCTGCACGC CTTCGCCCTC GACTTCGGCC AGGCGTTTCA ACTGCTGGAC    810
GATCTGCGTG ACGATCACCC GGAAACCGGT AAAGATCGCA ATAAGGACGC GGGAAAATCG    870
ACGCTGGTCA ACCGGCTGGG CGCAGACGCG GCCCGGCAAA AGCTGCGCGA GCATATTGAT    930
TCCGCCGACA AACACCTCAC TTTTGCCTGT CCGCAGGGCG GCGCCATCCG ACAGTTTATG    990
CATCTGTGGT TTGGCCATCA CCTTGCCGAC TGGTCACCGG TCATGAAAAT CGCCTGATAC   1050
CGCCCTTTTG GGTTCAAGCA GTACATAACG ATGGAACCAC ATTACAGGAG TAGTGATGAA   1110
TGAAGGACGA GCGCCTTGTT CAGCGTAAGA ACGATCATCT GGATATC                 1157
```

(2) INFORMATION FOR SEQ ID NO:4:

(i) SEQUENCE CHARACTERISTICS:
     (A) LENGTH: 298 amino acids
     (B) TYPE: amino acid
     (D) TOPOLOGY: linear (ii) MOLECULE TYPE: protein (xi) SEQUENCE DESCRIPTION: SEQ ID NO:4:

```
Met  Ala  Glu  Phe  Glu  Ile  Glu  Val  Met  Arg  Gln  Ser  Ile  Asp  Asp  His
 1              5                        10                       15

Leu  Ala  Gly  Leu  Leu  Pro  Glu  Thr  Asp  Ser  Gln  Asp  Ile  Val  Ser  Leu
              20                       25                       30

Ala  Met  Arg  Glu  Gly  Val  Met  Ala  Pro  Gly  Lys  Arg  Ile  Arg  Pro  Leu
              35                       40                       45

Leu  Met  Leu  Leu  Ala  Ala  Arg  Asp  Leu  Arg  Tyr  Gln  Gly  Ser  Met  Pro
              50                       55                       60

Thr  Leu  Leu  Asp  Leu  Ala  Cys  Ala  Val  Glu  Leu  Thr  His  Thr  Ala  Ser
 65                        70                       75                       80

Leu  Met  Leu  Asp  Asp  Met  Pro  Cys  Met  Asp  Asn  Ala  Glu  Leu  Arg  Arg
                     85                       90                       95
```

| | | | | | | | | | | | | | | |
|---|---|---|---|---|---|---|---|---|---|---|---|---|---|---|
| Gly | Gln | Pro | Thr 100 | Thr | His | Lys | Lys | Phe 105 | Gly | Glu | Ser | Val | Ala 110 | Ile | Leu |
| Ala | Ser | Val 115 | Gly | Leu | Leu | Ser | Lys 120 | Ala | Phe | Gly | Leu | Ile 125 | Ala | Ala | Thr |
| Gly | Asp 130 | Leu | Pro | Gly | Glu | Arg 135 | Arg | Ala | Gln | Ala | Val 140 | Asn | Glu | Leu | Ser |
| Thr 145 | Ala | Val | Gly | Leu | Gln 150 | Gly | Leu | Val | Leu | Gly 155 | Gln | Phe | Arg | Asp | Leu 160 |
| Asn | Asp | Ala | Ala | Leu 165 | Asp | Arg | Thr | Pro | Asp 170 | Ala | Ile | Leu | Ser | Thr 175 | Asn |
| His | Leu | Lys | Thr 180 | Gly | Ile | Leu | Phe | Ser 185 | Ala | Met | Leu | Gln | Ile 190 | Val | Ala |
| Ile | Ala | Ser 195 | Ala | Ser | Ser | Pro | Ser 200 | Thr | Arg | Glu | Thr | Leu 205 | His | Ala | Phe |
| Ala | Leu 210 | Asp | Phe | Gly | Gln | Ala 215 | Phe | Gln | Leu | Leu | Asp 220 | Asp | Leu | Arg | Asp |
| Asp 225 | His | Pro | Glu | Thr | Gly 230 | Lys | Asp | Arg | Asn | Lys 235 | Asp | Ala | Gly | Lys | Ser 240 |
| Thr | Leu | Val | Asn | Arg 245 | Leu | Gly | Ala | Asp | Ala 250 | Ala | Arg | Gln | Lys | Leu 255 | Arg |
| Glu | His | Ile | Asp 260 | Ser | Ala | Asp | Lys | His 265 | Leu | Thr | Phe | Ala | Cys 270 | Pro | Gln |
| Gly | Gly | Ala 275 | Ile | Arg | Gln | Phe | Met 280 | His | Leu | Trp | Phe | Gly 285 | His | His | Leu |
| Ala | Asp 290 | Trp | Ser | Pro | Val | Met 295 | Lys | Ile | Ala | | | | | | |

(2) INFORMATION FOR SEQ ID NO:5:

(i) SEQUENCE CHARACTERISTICS:
    (A) LENGTH: 1198 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

```
                                                            GATTG AGGATCTGCA    15
ATGAGCCAAC CGCCGCTGCT TGACCACGCC ACGCAGACCA TGGCCAACGG CTCGAAAAGT    75
TTTGCCACCG CTGCGAAGCT GTTCGACCCG GCCACCCGCC GTAGCGTGCT GATGCTCTAC   135
ACCTGGTGCC GCCACTGCGA TGACGTCATT GACGACCAGA CCCACGGCTT CGCCAGCGAG   195
GCCGCGGCGG AGGAGGAGGC CACCCAGCGC CTGGCCCGGC TGCGCACGCT GACCCTGGCG   255
GCGTTTGAAG GGGCCGAGAT GCAGGATCCG GCCTTCGCTG CCTTTCAGGA GGTGGCGCTG   315
ACCCACGGTA TTACGCCCCG CATGGCGCTC GATCACCTCG ACGGCTTTGC GATGGACGTG   375
GCTCAGACCC GGTATGTCAC CTTTGAGGAT ACGCTGCGCT ACTGCTATCA CGTGGCGGGC   435
GTGGTGGGTC TGATGATGGC CAGGGTGATG GGCGTGCGGG ATGAGCGGGT GCTGGATCGC   495
GCCTGCGATC TGGGGCTGGC CTTCCAGCTG ACGAATATGG CCCGGGATAT TATTGACGAT   555
GCGGCTATTG ACCGCTGCTA TCTGCCCGCC GAGTGGCTGC AGGATGCCGG GCTGGCCCCG   615
GAGAACTATG CCGCGCGGGA GAATCGCCCC GCGCTGGCGC GGTGGCGGAG CTTATTGAT   675
GCCGCAGAGC CGTACTACAT CTCCTCCCAG GCCGGGCTAC ACGATCTGCG GCGGCGCTCC   735
GCGTGGGCGA TCGCCACCGC CCGCAGCGTC TACCGGGAGA TCGGTATTAA GGTAAAAGCG   795
```

```
GCGGGAGGCA GCGCCTGGGA TCGCCGCCAG CACACCAGCA AAGGTGAAAA AATTGCCATG    855

CTGATGGCGG CACCGGGGCA GGTTATTCGG GCGAAGACGA CGAGGGTGAC GCCGCGTCCG    915

GCCGGTCTTT GGCAGCGTCC CGTTTAGGCG GGCGGCCATG ACGTTCACGC AGGATCGCCT    975

GTAGGTCGGC AGGCTTGCGG GCGTAAATAA AACCGAAGGA GACGCAGCCC TCCCGGCCGC   1035

GCACCGCGTG GTGCAGGCGG TGGGCGACGT AGAGCCGCTT CAGGTAGCCC CGGCGCGGGA   1095

TCCAGTGGAA GGGCCAGCGC TGATGCACCA GACCGTCGTG CACCAGGAAG TAGAGCAGGC   1155

CATAGACCGT CATGCCGCAG CCAATCCACT GCAGGGGCCA AAC                    1198
```

( 2 ) INFORMATION FOR SEQ ID NO:6:

( i ) SEQUENCE CHARACTERISTICS:
        ( A ) LENGTH: 308 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Gln Pro Pro Leu Leu Asp His Ala Thr Gln Thr Met Ala Asn
 1               5                  10                  15

Gly Ser Lys Ser Phe Ala Thr Ala Ala Lys Leu Phe Asp Pro Ala Thr
                20                  25                  30

Arg Arg Ser Val Leu Met Leu Tyr Thr Trp Cys Arg His Cys Asp Asp
            35                  40                  45

Val Ile Asp Asp Gln Thr His Gly Phe Ala Ser Glu Ala Ala Ala Glu
        50                  55                  60

Glu Glu Ala Thr Gln Arg Leu Ala Arg Leu Arg Thr Leu Thr Leu Ala
 65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
                100                 105                 110

Leu Asp Gly Phe Ala Met Asp Val Ala Gln Thr Arg Tyr Val Thr Phe
            115                 120                 125

Glu Asp Thr Leu Arg Tyr Cys Tyr His Val Ala Gly Val Val Gly Leu
        130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Met Ala Arg Asp
                165                 170                 175

Ile Ile Asp Asp Ala Ala Ile Asp Arg Cys Tyr Leu Pro Ala Glu Trp
                180                 185                 190

Leu Gln Asp Ala Gly Leu Ala Pro Glu Asn Tyr Ala Ala Arg Glu Asn
            195                 200                 205

Arg Pro Ala Leu Ala Arg Trp Arg Arg Leu Ile Asp Ala Ala Glu Pro
        210                 215                 220

Tyr Tyr Ile Ser Ser Gln Ala Gly Leu His Asp Leu Arg Arg Arg Ser
225                 230                 235                 240

Ala Trp Ala Ile Ala Thr Ala Arg Ser Val Tyr Arg Glu Ile Gly Ile
                245                 250                 255

Lys Val Lys Ala Ala Gly Gly Ser Ala Trp Asp Arg Arg Gln His Thr
                260                 265                 270

Ser Lys Gly Glu Lys Ile Ala Met Leu Met Ala Ala Pro Gly Gln Val
            275                 280                 285
```

Ile Arg Ala Lys Thr Thr Arg Val Thr Pro Arg Pro Ala Gly Leu Trp
290                     295                 300

Gln Arg Pro Val
305

( 2 ) INFORMATION FOR SEQ ID NO:7:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
                20                  25                  30

Ala Ser Phe Pro Val Ser Arg Lys Gln Asn Leu Asp Ile Thr Ser Ile
            35                  40                  45

Ala Ser Asn Gly Gly Arg Val Gln Cys Met Gln
            50                  55

( 2 ) INFORMATION FOR SEQ ID NO:8:

( i ) SEQUENCE CHARACTERISTICS:
        ( A ) LENGTH: 177 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
ATGGCTTCCT CAGTTCTTTC CTCTGCAGCA GTTGCCACCC GCAGCAATGT TGCTCAAGCT      60
AACATGGTGG CGCCTTTCAC TGGCCTTAAG TCAGCTGCCT CATTCCCTGT TTCAAGGAAG     120
CAAAACCTTG ACATCACTTC CATTGCCAGC AACGGCGGAA GAGTGCAATG CATGCAG       177
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
TCAGCGGGTA ACCTTGCCAT GGGGAGTGGC AGTAAAGCG                             39
```

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
TTGCAATGGT GA                                                          12
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TTGCCATGGG GA                                                  12

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CATGGCGAAA TAGAAGCCAT GGGACAATCC ATTGACGAT              39

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAGTAATGAG AC                                                  12

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AAGCCATGGG AC                                                  12

( 2 ) INFORMATION FOR SEQ ID NO:15:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Met Val Ser Gly Ser Lys Ala Gly Val Ser Pro His Arg Glu Ile
    1                5                        10                     15

( 2 ) INFORMATION FOR SEQ ID NO:16:

( i ) SEQUENCE CHARACTERISTICS:
        ( A ) LENGTH: 6 amino acids
        ( B ) TYPE: amino acid ( D ) TOPOLOGY: linear ( i i ) MOLECULE TYPE: peptide ( x i ) SEQUENCE DESCRIPTION: SEQ ID NO:16:

Met Ala Glu Phe Glu Ile
1               5

( 2 ) INFORMATION FOR SEQ ID NO:17:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

TAAGCATGCT CGAATTCGAA ATAGAAGTAA TG                32

( 2 ) INFORMATION FOR SEQ ID NO:18:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

CCGCGCATGC GACCCTTGTG TATCAAACAA G                 31

( 2 ) INFORMATION FOR SEQ ID NO:19:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CTTGTTTGAT ACACAAGGGT CGCATCTGCG G                 31

( 2 ) INFORMATION FOR SEQ ID NO:20:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

CTTGTTTGAT ACACAAGGGT CGCATGCGCG G                 31

( 2 ) INFORMATION FOR SEQ ID NO:21:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CATGGCTTCC TCAGTTCTTT CCTCTGCAGC AGTTGCC 37

( 2 ) INFORMATION FOR SEQ ID NO:22:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GGGTGGCAAC TGCTGCAGAG GAAAGAACTG AGGAAGC 37

( 2 ) INFORMATION FOR SEQ ID NO:23:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

ACCCGCAGCA ATGTTGCTCA AGCTAACATG GTGG 34

( 2 ) INFORMATION FOR SEQ ID NO:24:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CGCCACCATG TTAGCTTGAG CAACATTGCT GC 32

( 2 ) INFORMATION FOR SEQ ID NO:25:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CGCCTTTCAC TGGCCTTAAG TCAGCTGCCT CATTCCCTGT TTCAAGGAAG 50

( 2 ) INFORMATION FOR SEQ ID NO:26:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TTTGCTTCCT TGAAACAGGG AATGAGGCAG CGAATGAGGC AGCTGACTTA AGGCCAGTCA 60

AAGG 64

( 2 ) INFORMATION FOR SEQ ID NO:27:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
CAAAACCTTG ACATCACTTC CATTGCCAGC AACGGCGGAA GAGTGCAATG CATG          54
```

( 2 ) INFORMATION FOR SEQ ID NO:28:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
CATTGCACTC TTCCGCCGTT GCTGGCAATG GAAGTGATGT CAAGGT                   46
```

( 2 ) INFORMATION FOR SEQ ID NO:29:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
CATGGCTTCC TCAGTTCTTT CCTCTGCAGC AGTTGCCACC CGCAGCAATG TTGCTCAAGC    60
TAACATGGTG G                                                        71
```

( 2 ) INFORMATION FOR SEQ ID NO:30:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
CGCCACCATG TTAGCTTGAG CAACATTGCT GCGGGTGGCA CTGCTGCAG AGGAAAGAAC     59
TGAGGAAGC                                                           68
```

( 2 ) INFORMATION FOR SEQ ID NO:31:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
CGCCTTTCAC TGGCCTTAAG TCAGCTGCCT CATTCCCTGT TTCAAGGAAG CAAAACCTTG    60
```

ACATCACTTC CATTGCCAGC AACGGCGGAA GAGTGCAATG CATG 104

( 2 ) INFORMATION FOR SEQ ID NO:32:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CATTGCACTC TCCGCCGTT GCTGGCAATG GAAGTGATGT CAAGGTTTTG CTTCCTTGAA 59

ACAGGGAATG AGGCAGCTGA CTTAAGGCCA GTGAAAGG 97

( 2 ) INFORMATION FOR SEQ ID NO:33:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CCTGCAGGCA TCCAACCATG GCGTAATCAT GGTCAT 36

( 2 ) INFORMATION FOR SEQ ID NO:34:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GATCTAAAAT GAGCCAACCG CCGCTGCTTG ACCACGCCAC GCAGAC 46

( 2 ) INFORMATION FOR SEQ ID NO:35:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CATGGTCTGC GTGGCGTGGT CAAGCAGCGG CGGTTGGCTC ATTTTA 46

( 2 ) INFORMATION FOR SEQ ID NO:36:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

ACAACAAAAT ATAAAAACAA TGTCTTTA 28

( 2 ) INFORMATION FOR SEQ ID NO:37:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:37:

ACAACAAGAT CTAAAAACAA TGTCTTTA      28

( 2 ) INFORMATION FOR SEQ ID NO:38:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

AATTCCCGGG CCATGGC      17

( 2 ) INFORMATION FOR SEQ ID NO:39:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

AATTGCCATG GCCCGGG      17

( 2 ) INFORMATION FOR SEQ ID NO:40:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

TCGCATGCGC CAACGCCGCT GCTTGACCAC GC      32

( 2 ) INFORMATION FOR SEQ ID NO:41:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

CTGTCGACGG CTACTGAGCG GCTCTACGTC      30

( 2 ) INFORMATION FOR SEQ ID NO:42:

( i ) SEQUENCE CHARACTERISTICS:
    ( A ) LENGTH: 30 base pairs
    ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:42:

GACGTAGAGC CGCTTCAGGT AGCCCCGGCG                     30

(2) INFORMATION FOR SEQ ID NO:43:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:43:

CACGTAGAGC CGCTCAGTAG CCGTCGACAG                     30